US011834497B2

(12) United States Patent
Tucker et al.

(10) Patent No.: US 11,834,497 B2
(45) Date of Patent: Dec. 5, 2023

(54) GLUCOSE TRANSPORTER 4 ANTIBODIES, METHODS OF MAKING THE SAME, AND USES THEREOF

(71) Applicant: INTEGRAL MOLECULAR, INC., Philadelphia, PA (US)

(72) Inventors: David F. Tucker, Medford, MA (US); Kimberly-Anne Mattia, Plymouth Meeting, PA (US); Christine R. Fisher, Sommerville, MA (US); Benjamin J. Doranz, Philadelphia, PA (US); Joseph B. Rucker, Philadelphia, PA (US)

(73) Assignee: INTEGRAL MOLECULAR, INC., Philadelphia, PA (US)

( * ) Notice: Subject to any disclaimer, the term of this patent is extended or adjusted under 35 U.S.C. 154(b) by 235 days.

(21) Appl. No.: 17/051,241

(22) PCT Filed: Apr. 30, 2019

(86) PCT No.: PCT/US2019/029809
§ 371 (c)(1),
(2) Date: Oct. 28, 2020

(87) PCT Pub. No.: WO2019/213024
PCT Pub. Date: Nov. 7, 2019

(65) Prior Publication Data
US 2021/0238276 A1    Aug. 5, 2021

Related U.S. Application Data

(60) Provisional application No. 62/664,470, filed on Apr. 30, 2018.

(51) Int. Cl.
| C07K 16/28 | (2006.01) |
| A61P 3/10 | (2006.01) |
| C07K 14/705 | (2006.01) |
| G01N 33/68 | (2006.01) |

(52) U.S. Cl.
CPC ........... *C07K 16/28* (2013.01); *A61P 3/10* (2018.01); *C07K 14/705* (2013.01); *G01N 33/6893* (2013.01); *C07K 2317/565* (2013.01); *C07K 2317/77* (2013.01); *C07K 2317/92* (2013.01)

(58) Field of Classification Search
CPC ... C07K 16/28; C07K 2317/92; C07K 14/705
See application file for complete search history.

(56) References Cited

U.S. PATENT DOCUMENTS

| 5,580,561 A * | 12/1996 | Cercek ............. C07K 14/585 |
| | | 424/139.1 |
| 7,449,556 B2 | 11/2008 | Ignjatovic et al. |
| 9,074,002 B2 | 7/2015 | Tonks et al. |
| 2004/0123343 A1 | 6/2004 | La Rosa et al. |
| 2011/0182907 A1 | 7/2011 | Leu et al. |
| 2017/0035917 A1 | 2/2017 | Bradley et al. |
| 2017/0088620 A1 | 3/2017 | Nioi et al. |

FOREIGN PATENT DOCUMENTS

| EP | 1420800 | * | 9/2011 |
| WO | 1996009317 A1 | | 3/1996 |
| WO | 2013138518 A1 | | 9/2013 |
| WO | 2017192567 A1 | | 11/2017 |

OTHER PUBLICATIONS

Rudikoff et al., Proc. Natl. Acad. Sci. 79: 1979-1983, (1982).*
Chamow and Ashkenazi, Ibtech 14: 52-60, (1996).*
Armoni, et al: "Transcriptional Regulation of the GLUT4 Gene: from PPAR-@c and FOX01 to FFA and Inflamation," Trends in Endocrinology and Metabolism, Elsevier Science Publishing, New York, NY, US, vol. 18, No. 3, Mar. 24, 2007, pp. 100-107, XP0220000504, ISSN: 1043-2760, DOI: 10.1016/J.TEM.2007.02.001.
Extended European Search Report dated Mar. 17, 2022, from Corresponding Europeon Patent Application EP19796828.
Hresko, et al., "Isoform-Selective Ingibition of Facilitative Glucose Transporters: Elucidation of the Moleculare Mechanism of HIV Protease Inhibitor Binding", J Biol Chem., vol. 289, No. 23 (2014) pp. 16100-16113.
International Search Report and Written Opinion dated Sep. 17, 2019 from Corresponding International Applciation No. PCT/US2019/029809, International Filing Date Apr. 30, 2019.
Kim et al. "The First Luminal Loop Confers Insulin Responsiveness to Glucose Transporter 4" Mol Biol Cell, Mar. 1, 2012, vol. 23 No. 5, pp. 910-917.
Kobashi H. et al: "Expression fo Glucose Transporter 4 in the Human Pancreatic Islet of Langerhans," Biochemical and Biophysical Research Communications, Elsevier, Amsterdam NL, vol. 314, No. 4, Feb. 20, 2004, pp. 1121-1125, XP004486127, ISSN: 0006-291X, DOI: 10.1016/J.BBRC.2004.01.010.
Nishimura et al "Monoclonal Antibodies Possibly Recognize Conformational Changes in the Human Erythrocye Glucose Transporter" Biochem J., Jan. 1, 1992, vol. 281, No. 1, pp. 103, 106.
Poojari et al. "Molecular Basis of GLUT4 in Glucose Transport: Atomistic Molecular Dynamics Study" Biophysical Journal, Feb. 2017, vol. 112, No. 3, pp. 139a.
Sano et al: "A Potential Link Between Insulin Signaling and GLUT4 Translocation: Association of Rab10-GTP with the Exocyst Subunit Exoc6/6b," Biochemical and Biophysical Research Communications, Elsevier, Amsterdam, NL, vol. 465, No. 3, Aug. 20, 2015, pp. 601-605, XP029274999, ISSN: 0006-291X, DOI: 10.1016/J.BBRC.2015.08.069.
Stafford et al. "Discovery of New Therapeutic Monoclonal Antibodies to Challenging GPCRs, Ion Channels and Transporters" Cancer Res., 2017, Vo. 77, No. 13, p. 1.

(Continued)

*Primary Examiner* — Gyan Chandra
(74) *Attorney, Agent, or Firm* — Goodwin Procter LLP

(57) ABSTRACT

Antibodies and compositions against GLUT4 and uses thereof are provided herein.

10 Claims, 6 Drawing Sheets
Specification includes a Sequence Listing.

(56) References Cited

OTHER PUBLICATIONS

Tucker David F. et al: "Isolation of State-Dependent Monoclonal Antibodies Against the 12-Transmembrane Domain Glucose Transporter 4 Using Virus-Like Particles," Proceedings of The National Academy of Sciences, vol. 115, No. 22, 29, May 29, 2018, pp. E4990-E4999, XP055806882, ISSN: 0027-8424, DOI: 10.1073/pnas.1716788115, https://www.ncbi.nlm.nih.gov/pmc/articles/PMC5984492/pdf/pnas.201716788.pdf.

* cited by examiner

|  | AB102 | AB105 | AB108 | AB111 |
|---|---|---|---|---|
| Apparent affinity | ND | 1.0E-12M | 1.8E-9M | 5.6E-10M |
| VH CDR3 length | 18aa | 26aa | 16aa | 16aa |
| hsGLUT4 | Yes | Yes | Yes | Yes |
| mmGLUT4 | Yes | Yes | Yes | Yes |
| hsGLUT1 | Yes | No | No | No |
| Topology | Cytoplasmic | Extracellular | Extracellular | Extracellular |
| Conformation | Inward-open | Outward-open | All | All |
| Domain | ICL3, ICL5 | ECL4, ECL6 | ECL1 | ECL1 |
| Critical residues | R265, G414 | E315, G446 | L61, G65, P66 | G65 |

Summary of GLUT MAb Characteristics. ND: Not determined.

FIG. 5

GLUCOSE TRANSPORTER 4 ANTIBODIES, METHODS OF MAKING THE SAME, AND USES THEREOF

CROSS-REFERENCE TO RELATED APPLICATIONS

This application is a U.S. National Phase application under 35 U.S.C. § 371 of International Application No. PCT/US2019/029809, filed Apr. 30, 2019, which claims priority to U.S. Provisional Application No. 62/664,470, filed Apr. 30, 2018, both of which are hereby incorporated by reference in their entirety.

GOVERNMENT LICENSE RIGHTS

This invention was made with government support under grants DC010105 and GM113556 awarded by the National Institutes of Health. The government has certain rights in the invention.

BACKGROUND

GLUT (SLC2A) proteins are a large family of glucose transporters, with fourteen unique members identified in humans. GLUT proteins are highly conserved, structurally complex molecules of ~500 amino acids, each possessing twelve transmembrane (TM) domains, a large intracellular loop between helices VI and VII, and six small extracellular loops. The well-characterized glucose transporter isoforms GLUT1-4 have distinct regulatory and kinetic properties that reflect their specific roles in cellular and physiological glucose homeostasis. GLUT4 is one of the best studied proteins of the GLUT family, reflecting its vital role in glucose metabolism, its complex mechanism of regulation by the hormone insulin, and the established links between disruption of GLUT4 regulation and prevalent human diseases including diabetes and obesity (2).

GLUT4 is primarily expressed in adipose and muscle tissues. A complex network of signaling pathways and membrane trafficking events downstream of the insulin receptor is responsible for the temporal regulation of GLUT4 expression at the plasma membrane. Under basal conditions, less than 1% of total GLUT4 is present at the plasma membrane, with the remainder localizing to intracellular organelles and GLUT4 storage vesicles. In response to insulin, GLUT4 is rapidly mobilized to the cell surface, where it increases the rate of glucose uptake into the cell, thereby contributing to the maintenance of acceptable glucose levels (3). Type 2 diabetes is, in part, defined by the inability of insulin to stimulate GLUT4 mobilization (insulin resistance).

Studying GLUT4 trafficking to the cell surface remains difficult, in part because of the scarcity of tools available to measure wild type GLUT4 protein (3, 4). Translocation of GLUT4 to the plasma membrane has been studied primarily using fluorescently tagged GLUT4. For example, using a hemagglutinin (HA) epitope tag inserted into the first external loop of GLUT4 and a green fluorescent protein tag at the C-terminus, the amount of HA tag exposed on the surface can be used to measure GLUT4 surface translocation (5, 6). Such approaches, although valuable, are limited to monitoring tagged exogenous proteins expressed in vitro. Antibodies that recognize endogenous GLUT4 have proven valuable as research tools (7-10), but all of these antibodies recognize intracellular domains and linear epitopes of the protein (7), limiting their utility for studying GLUT4 on the cell surface.

Complicating its detection further, GLUT4 is known to cycle between several different conformational states that together facilitate glucose transit, including an inward-open state and an outward-open state (11). Pharmacological compounds such as cytochalasin B and phloretin can lock GLUT4 in each of these states, as can select point mutations such as E345Q and Y3091 (12, 13). MAbs that can differentiate these states are not yet available for GLUT4—or for most other transporters—but for other membrane proteins, such as GPCRs and ion channels, state-specific MAbs have led to unprecedented insight into their structure, function, and signaling mechanisms (14-16).

A key challenge in creating antibodies against the native extracellular regions of GLUT4 is maintenance of the native structure of the antigen for immunization and MAb isolation. Multispanning membrane proteins such as GLUT4 require the lipid membrane to maintain their structure, making antigen preparation difficult. Current commercial antibodies against GLUT4 all recognize short peptide epitopes that are useful for applications such as Western blotting, but are ineffective for applications that rely on native folded epitopes, such as flow cytometry (17). Most successful approaches to raising MAbs that bind extracellular regions of multispanning membrane proteins have used the full length protein in a membrane context by using whole cells, liposome-reconstituted protein, or DNA (18). Even then, however, the relatively small extracellular loops of GLUT4 (five of the six loops are 8 to 12 amino acids) form a small target antigen for immune reactivity. Compounding the difficulty of isolating MAbs, GLUT4 is highly conserved among mammals (95-97% homology), making traditional animal hosts poor candidates for immunization.

Thus, there is a need for antibodies that can bind to conformationally relevant forms of GLUT4 and antibodies that can modulate the activity of GLUT4. The present disclosure provides for these needs as well as others.

SUMMARY

In some embodiments, isolated antibodies are provided that bind to GLUT4 or a nucleic acid molecule encoding the same.

In some embodiments, pharmaceutical composition are provided comprising one or more antibodies described herein or a nucleic acid molecule encoding the same.

In some embodiments, recombinant antibodies that binds to a GLUT4 protein in its native conformation are provided. In some embodiments, the GLUT4 protein is human GLUT4 protein. In some embodiments, the antibody is an antibody that is generated by inducing an immune response against GLUT4 in a chicken. In some embodiments, the antibody is a scFv antibody.

In some embodiments, GLUT4 specific antibodies that bind to residues R265 and G414 of GLUT4 are provided.

In some embodiments, GLUT4 specific antibodies that binds to an inward-open GLUT4 protein in a native environment are provided.

In some embodiments, antibodies that binds to an epitope of GLUT4 comprising residues E315 and G446 are provided.

In some embodiments, antibodies that specifically bind to an outward-open form of GLUT4 in a native environment are provided.

In some embodiments, antibodies to an epitope of GLUT4 comprising the residues of L61, G65, and P66 are provided.

In some embodiments, antibodies that binds to an epitope of GLUT4 comprising the residue G65.

In some embodiments, nucleic acid molecules encoding an antibody, or antigen binding fragment thereof described herein are provided.

In some embodiments, vectors comprising the nucleic acid molecules are provided.

In some embodiments, cells comprising the nucleic acid molecules or the vectors are provided.

In some embodiments, pharmaceutical composition comprising the nucleic acid molecules, cells, vectors, proteins, antibodies, or antigen binding fragments thereof, are provided.

In some embodiments, methods of modulating GLUT4 internalization are provided. In some embodiments, the methods comprise contacting a cell expressing GLUT4 with a GLUT4 antibody or a pharmaceutical composition comprising the same that binds to GLUT4 on the cell surface. The antibody, or antigen binding fragment thereof, can be as provided for herein. In some embodiments, the method comprises administering to a subject the antibodies as provided for herein, or a pharmaceutical composition comprising the same, to modulate GLUT4 internalization in the subject.

In some embodiments, methods of inhibiting the function of GLUT4 are provided. In some embodiments, the method comprises contacting a cell expressing GLUT4 with an antibody as provided for herein, or a pharmaceutical composition comprising the same, to inhibit the function of GLUT4. In some embodiments, the method comprises administering to a subject the antibodies as provided for herein, or a pharmaceutical composition comprising the same, to inhibit the function of GLUT4 in the subject.

In some embodiments, methods of treating a subject with a GLUT4 mediated disorder are provided. In some embodiments, the methods comprise administering a pharmaceutical composition comprising an antibody as provided for herein.

In some embodiments, methods of treating insulin resistance, obesity, diabetes or cancer are provided. In some embodiments, the methods comprise administering a pharmaceutical composition comprising an antibody as provided for herein.

In some embodiments, GLUT4 mutant proteins are provided.

BRIEF DESCRIPTION OF DRAWINGS

FIG. 5 illustrates some characteristics of antibodies provided herein.

DETAILED DESCRIPTION

Figure 1:
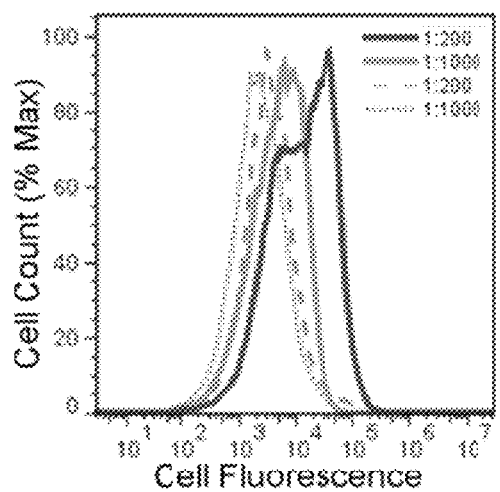
FIG. 1, panels A, B, C, and D illustrates, for example, GLUT4 VLPs enable immunization and phage display for GLUT4-reactive MAbs. (A) Screening of serum from a GLUT4 VLP-immunized chicken for reactivity. QT6 cells expressing GLUT4 or a negative control were treated with serum samples followed by biotinylated bovine anti-IgY antibody and Streptavidin PerCP, and analyzed by flow cytometry. Serum reactivity fluorescence profiles against hsGLUT4-expressing cells are indicated in red and blue at 1:200 and 1:1000 serum dilutions, respectively. Serum reactivity fluorescence profiles against negative control-expressing cells are shown as dashed lines at 1:200 and 1:1000 serum dilutions, respectively. (B) A phage scFv library was created using B cells from a chicken with the highest reactive serum. The resulting phage library was used to pan against VLPs displaying the native form of hsGLUT4 on their surface. (C) scFvs isolated from the phage clones were tested for hsGLUT4 target selectivity in 384-well ELISA plates coated with hsGLUT4 VLPs or with null VLPs (VLPs produced without a specific receptor) as a negative control. Individual clones displaying more than a 5:1 signal-to-noise ratio for hsGLUT4 are shown as red bars, while the clones with a<5:1 ratio are shown as grey bars. Twenty-nine of these positive clones represented unique H-CDR3 sequences. (D) The distribution of murine, human, and chicken H-CDR3 length is shown. The six families of Glut4 MAbs isolated here are plotted by their H-CDR3 length (bars). Numbers above each bar indicate the number of MAb families represented.
Figure 1:
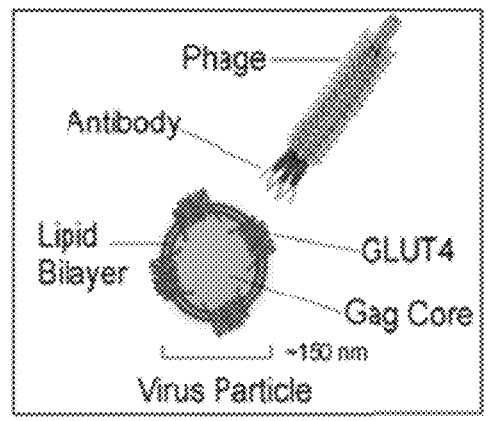
Figure 1:
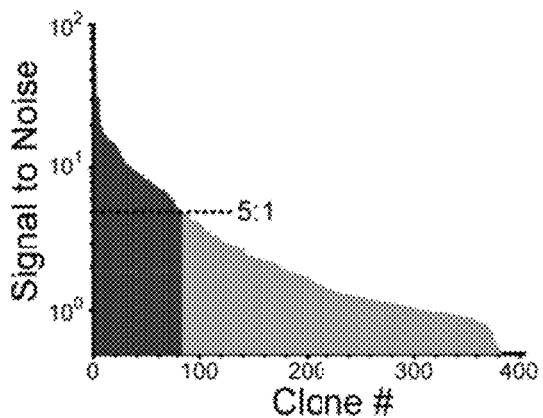
Figure 1:
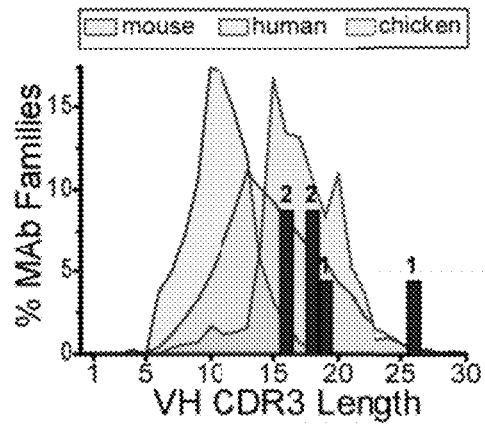

Provided herein are antibodies, such as conformational MAbs (monoclonal antibodies), that recognize the extracellular and intracellular domains of GLUT4, including MAbs that are specific for both the inward-open and outward-open states of GLUT4. MAbs against the native structure of GLUT4 have never before been described, and no inhibitory MAbs of GLUT4 have been reported, despite work on this protein for several decades. Accordingly, the present disclosure provides surprising and unexpected results, which is, in part, antibodies that can bind to GLUT4 in its native structure and/or its native environment. Additionally, it is surprising and unexpected to make antibodies that inhibit GLUT4. Without being bound to any particular theory, an antibody that binds to GLUT4 protein that is said to be in its native environment or native structure refers to a GLUT4 protein that is in a plasma membrane (cell membrane) or a bi-layer structure. An antibody that inhibits GLUT4 protein activity that is said to be in its native environment or native structure refers to an antibody that inhibits GLUT4 protein that is in a plasma membrane (cell membrane) or a bi-layer structure.

In some embodiments, antibodies against GLUT4 bind to GLUT4 in a conformationally independent or state-specific manner. In some embodiments, the antibody binds specifically to an inward-open, outward open, or an intermediate state form of GLUT4. For example, the antibodies bind to GLUT4 in a conformation inducible by cytochalasin A or the E345Q mutation for the inward-open state or a conformation inducible by phloretin or the Y3091 mutation for the outward open state.

In some embodiments, MAbs against GLUT4 were generated using virus-like particles (VLPs) to present this multispanning membrane protein in its native conformation, and a divergent host species (chickens) was chosen for immunization to overcome immune tolerance. In some embodiments, the MAbs isolated and characterized (AB102, AB105, AB108, and AB111) recognize conformational epitopes on native GLUT4 within intact human cells, and demonstrate remarkable specificity within the GLUT family, reacting with a mouse ortholog but not most other members of the human membrane proteome. Biosensor analysis using intact GLUT4 demonstrated the high affinity of the MAbs, with the strongest apparent affinity displayed by AB105 (<1 pM), which also inhibited the function of GLUT4 and stained endogenous GLUT4 on 3T3-L1 adipocytes Surprisingly, binding of MAbs AB102 and AB105 was dependent on the inward-open and outward-open conformational states of GLUT4, respectively. Epitope mapping of the MAbs, performed using shotgun mutagenesis alanine scanning across the 509 amino acids of GLUT4, identified distinct sets of GLUT4 residues critical for binding by each MAb. Also comprehensively identified were residues buried in the TMs that control the GLUT4 inward-open and outward-open states. To the best of our knowledge, AB102 and AB105 are the only state-specific MAbs ever isolated against a glucose transporter, and most of the residues that functionally control GLUT4 conformational states have not been previously identified.

In some embodiments, GLUT4 comprises an amino acid sequence comprising:

GLUT4 (human)
(SEQ ID NO: 1)
MPSGFQQIGSEDGEPPQQRVTGTLVLAVFSAVLGSLQFGYNIGVINAPQK

VIEQSYNETWLGRQGPEGPSSIPPGTLTTLWALSVAIFSVGGMISSFLIG

IISQWLGRKRAMLVNNVLAVLGGSLMGLANAAASYEMLILGRFLIGAYSG

-continued

LTSGLVPMYVGEIAPTHLRGALGTLNQLAIVIGILIAQVLGLESLLGTAS

LWPLLLGLTVLPALLQLVLLPFCPESPRYLYIIQNLEGPARKSLKRLTGW

ADVSGVLAELKDEKRKLERERPLSLLQLLGSRTHRQPLIIAVVLQLSQQL

SGINAVFYYSTSIFETAGVGQPAYATIGAGVVNTVFTLVSVLLVERAGRR

TLHLLGLAGMCGCAILMTVALLLLERVPAMSYVSIVAIFGFVAFFEIGPG

PIPWFIVAELFSQGPRPAAMAVAGFSNWTSNFIIGMGFQYVAEAMGPYVF

LLFAVLLLGFFIFTFLRVPETRGRTFDQISAAFHRTPSLLEQEVKPSTEL

EYLGPDEND

As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies and camelized single domain antibodies. "Parental antibodies" are antibodies obtained by exposure of an immune system to an antigen prior to modification of the antibodies for an intended use, such as humanization of an antibody for use as a human therapeutic antibody.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

A "Fab fragment" is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab') 2 molecule.

A "F(ab')$_2$ fragment" contains two light chains and two heavy chains containing a portion of the constant region between the $C_H1$ and $C_H^2$ domains, such that an interchain disulfide bond is formed between the two heavy chains. A F(ab') 2 fragment thus is composed of two Fab' fragments that are held together by a disulfide bond between the two heavy chains.

The "Fv region" comprises the variable regions from both the heavy and light chains, but lacks the constant regions.

The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

In certain embodiments, monoclonal antibodies herein also include camelized single domain antibodies. See, e.g., Muyldermans et al. (2001) Trends Biochem. Sci. 26:230; Reichmann et al. (1999) J. Immunol. Methods 231:25; WO 94/04678; WO 94/25591; U.S. Pat. No. 6,005,079). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$—$V_L$ or $V_L$—$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) Proc. Natl. Acad. Sci. USA 90: 6444-6448. For a review of engineered antibody variants generally see Holliger and Hudson (2005) Nat. Biotechnol. 23:1126-1136.

Typically, a variant antibody or antigen binding fragment of the antibodies provided herein retain at least 10% of its GLUT4 binding activity (when compared to a parental antibody that is modified) when that activity is expressed on a molar basis. In some embodiments, a variant antibody (or antigen fragment thereof), or antigen binding fragment of an antibody provided herein, retains at least 20%, 50%, 70%, 80%, 90%, 95% or 100% or more of the GLUT4 binding affinity as the parental antibody. As described herein, it is also intended that an antibody or antigen binding fragment of the invention can include conservative or non-conservative amino acid substitutions, which can also be referred to as "conservative variants" or "function conserved variants" of the antibody, that do not substantially alter its biologic activity.

"Isolated antibody" refers to the purification status of a binding compound and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

The term "monoclonal antibody", as used herein, refers to population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example. See also Presta (2005) J. Allergy Clin. Immunol. 116:731.

As used herein, a "chimeric antibody" is an antibody having the variable domain from a first antibody and constant domain from a second antibody, where the first and second antibodies are from different species. (U.S. Pat. No. 4,816,567; and Morrison et al., (1984) Proc. Natl. Acad. Sci. USA 81: 6851-6855). Typically the variable domains are obtained from an antibody from an experimental animal (the "parental antibody"), such as a rodent, and the constant domain sequences are obtained from human antibodies, so that the resulting chimeric antibody will be less likely to elicit an adverse immune response in a human subject than the parental (e.g. rodent) antibody.

As used herein, the term "humanized antibody" refers to forms of antibodies that contain sequences from both human and non-human (e.g., murine, rat) antibodies. In general, the humanized antibody will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully human antibody may contain rat carbohydrate chains if produced in a rat, in a rat cell, or in a hybridoma derived from a rat cell. Similarly, "rat antibody" refers to an antibody that comprises rat immunoglobulin sequences only.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, the term "hypervariable region" refers to the amino acid residues of an antibody that are responsible for antigen-binding. The hypervariable region comprises amino acid residues from a "complementarity determining region" or "CDR" (i.e. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain; Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (CDRL1), 50-52 (CDRL2) and 91-96 (CDRL3) in the light chain variable domain and 26-32 (CDRH1), 53-55 (CDRH2) and 96-101 (CDRH3) in the heavy chain variable domain; Chothia and Lesk (1987) *J. Mol. Biol.* 196: 901-917). As used herein, the term "framework" or "FR" residues refers to those variable domain residues other than the hypervariable region residues defined herein as CDR residues. CDRs provide the majority of contact residues for the binding of the antibody to the antigen or epitope. CDRs of interest can be derived from donor antibody variable heavy and light chain sequences, and include analogs of the naturally occurring CDRs, which analogs also share or retain the same antigen binding specificity and/or neutralizing ability as the donor antibody from which they were derived.

The term "chicken antibody" refers to an antibody that was raised in a chicken. For example, a protein of interest can be introduced into a chicken, such as in a VLP as provided for herein, to stimulate an immune response against the protein of interest to produce antibodies in the chicken. The antibody can then be humanized or otherwise modified as desired.

Additionally, in some embodiments, the antibodies can take the form of a full length antibody, single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; a Transbody; an Anticalin; an AdNectin; an Affilin; a Microbody; a peptide aptamer; an alterase; a plastic antibody; a phylomer; a stradobody; a maxibody; an evibody; a fynomer, an armadillo repeat protein, a Kunitz domain, an avimer, an atrimer, a probody, an immunobody, a triomab, a troybody; a pepbody; a vaccibody, a UniBody; Affimers, a DuoBody, a Fv, a Fab, a Fab', a F(ab')2, a peptide mimetic molecule, or a synthetic molecule, as described in US patent Nos. or Patent Publication Nos. U.S. Pat. No. 7,417,130, US 2004/ 132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004,746, 5,475,096, US 2004/ 146938, US 2004/157209, U.S. Pat. Nos. 6,994,982, 6,794, 144, US 2010/239633, U.S. Pat. No. 7,803,907, US 2010/ 119446, and/or U.S. Pat. No. 7,166,697, the contents of each of which are hereby incorporated by reference in their entireties. See also, Storz MAbs. 2011 May-June; 3(3): 310-317, which is hereby incorporated by reference.

The term "antigen" as used herein means any molecule that has the ability to generate antibodies either directly or indirectly. Included within the definition of "antigen" is a protein-encoding nucleic acid. An "antigen" can also refer to the binding partner of an antibody. In some embodiments, the antigen is the GLUT4 protein expressed on the surface of a cell or particle, such a virus-like particle. In some embodiments, the cell is an intact cell. An intact cell is a cell that has not been lysed or broken open with the use of detergents or other reagents. A cell that has been treated with detergents or other reagents that breaks up the cellular membrane or punches holes in a cellular membrane is not an intact cell. By expressing the receptor on the surface of the cell or particle, e.g. lipoparticle, the receptor can present conformational epitopes that may otherwise not be present if purified protein is used. An example is provided herein. In some embodiments, an adjuvant is not used, but an adjuvant can be used. In some embodiments, the particles are injected into a bird (e.g. chicken) to stimulate an immune response and generate antibodies against the protein present on the surface of the particle. Particles suitable for the generation of antibodies, and methods of making the same, are described in U.S. Pat. Nos. 8,377,691, 7,763,258, 8,158,130 and U.S. Patent Application Publication Nos. 20050123563 and 20120195882, each of which is hereby incorporated by reference. These publications and patents describe the generation of various particles, including lipoparticles, that can be used to express membrane spanning proteins (e.g. multiple-membrane spanning proteins, ion channels, and the like). GLUT4 can, in some embodiments, be incorporated, into the lipoparticles according to these methods or as provided for herein.

For example, methods are provided herein for generating an antibody that binds to a GLUT4 protein, the method comprising administering a virus-like particle comprising the GLUT4 protein on its surface to a subject under conditions to induce an immune response against the GLUT 4 protein to generate the antibody that binds to the GLUT4 protein. In some embodiments, the GLUT4 protein is a mutant GLUT4 protein. In some embodiments, the GLUT4 mutant protein is locked in conformational state. In some embodiments, the conformational state is outward-open or inward open. In some embodiments, the protein comprises a sequence of SEQ ID NO: 1, and a mutation at positions E345 or Y309. In some embodiments, the protein comprises a sequence of SEQ ID NO:1 with a E345Q and/or Y3091 mutation. In some embodiments, the protein comprises a E345A or Y309A mutation. In some embodiments, the mutation is at a position of: M112, M158, Y159, E162, I163, R169, L247, R265, Q295, L296, Q298, N304, V306, F307, Y309, S310, I313, F314, E315, E345, G348, F405, R416, or G446. In some embodiments, the residue at a position of M112, M158, Y159, E162, I163, R169, L247, R265, Q295, L296, Q298, N304, V306, F307, Y309, S310, I313, F314, E315, E345, G348, F405, R416, or G446 is substituted with an alanine. In some embodiments, the GLUT4 protein comprises 1, 2, 3, 4, or 5 of these substitutions. In some embodiments, the protein comprises a mutation selected from the group consisting of M112A, M158A, Y159A, E162A, I163A, R169A, L247A, R265A, Q295A, L296A, Q298A, N304A, V306A, F307A, Y309A, S310A I313A, F314A, E315A, E345A, G348A, F405A, R416A, or G446A. In some embodiments, a nucleic acid molecule encoding the various GLUT4 proteins is provided. In some embodiments, the nucleic acid molecule encodes a GLUT4 protein comprising a substitution at a position of: M112, M158, Y159, E162, I163, R169, L247, R265, Q295, L296, Q298, N304, V306, F307, Y309, S310, I313, F314, E315, E345, G348, F405, R416, or G446. In some embodiments, the nucleic acid molecule encodes a GLUT4 protein comprising a substitution at a position of: M112, M158, Y159, E162, I163, R169, L247, R265, Q295, L296, Q298, N304, V306, F307, Y309, S310, I313, F314, E315, E345, G348, F405, R416, or G446, wherein the substitution is an alanine.

In some embodiments, the methods further comprising isolating the antibody that binds to the GLUT4 protein. In some embodiments, the subject is a human, a mouse, sheep, a rat, a rabbit, a shark, a llama, or a chicken. In some embodiments, the antibody that is generated binds to GLUT 4 in a non-conformation dependent manner, inward-open GLUT4 protein, or outward-open GLUT4 protein. In some embodiments, the antibody that is generated binds to an extracellular domain of the GLUT4 protein. In some embodiments, the antibody that is generated binds to an intracellular domain of the GLUT4 protein. In some embodiments, the method comprises generating a virus-like particle comprising the GLUT4 protein, the method comprising transfecting or transducing a cell with GLUT4 protein and a gag protein under conditions sufficient to produce the virus-like particle comprising the GLUT4 protein. The VLPs can be generated as described and references above. In some embodiments, the cell is a HEK-293T cell. In some embodiments, the gag protein is a retroviral gag protein. In some embodiments, the retroviral gag protein is Murine Leukemia Virus (MLV) gag protein. In some embodiments, the Gag is HIV. In some embodiments, the Gag is rous sarcoma virus Gag.

As used herein, "specific binding" or "immunospecific binding" or "binds immunospecifically" refer to antibody binding to a predetermined antigen (e.g. GLUT4) or epitope present on the antigen. In some embodiments, the antibody binds with a dissociation constant ($K_D$) of $10^{-7}$ M or less, and binds to the predetermined antigen with a $K_D$ that is at least two-fold less than its $K_D$ for binding to a non-specific antigen (e.g., BSA, casein, or another non-specific polypeptide) other than the predetermined antigen. The phrases "an antibody recognizing GLUT4" and "an antibody specific for GLUT4" are used interchangeably herein with the term "an antibody which binds immunospecifically to GLUT4." Reference in the present disclosure may be made to GLUT4. In some embodiments, the antibody binds specifically to GLUT4 over other proteins. The degree of specificity necessary for an anti-GLUT4 antibody may depend on the intended use of the antibody, and at any rate is defined by its suitability for use for an intended purpose. In some embodiments, the antibody, or binding compound derived from the antigen-binding site of an antibody, of the contemplated method binds to its antigen (GLUT4), with an affinity that is at least two fold greater, at least ten times greater, at least 20-times greater, or at least 100-times greater than the affinity with any other antigen.

Methods for determining mAb specificity and affinity by competitive inhibition can be found in Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), and Muller, Meth. Enzymol. 92:589 601 (1983), which references are entirely incorporated herein by reference.

The term "homolog" means protein sequences having between 40% and 100% sequence homology or identity to a reference sequence. Percent identity between two peptide chains can be determined by pair wise alignment using the default settings of the AlignX module of Vector NTI v.9.0.0 (Invitrogen Corp., Carslbad, Calif.). In some embodiments, the antibody, or antigenic binding fragment thereof has, at least 50, 60, 70, 80, 90, 91, 92, 93, 94, 95, 96, 97, 98, or 99% homology or identity to a sequence described herein. In some embodiments, the antibody has conservative substitutions as compared to a sequence described herein. Exemplary conservative substitutions are illustrated in Table 1 and are encompassed within the scope of the disclosed subject matter. The conservative substitution may reside in the framework regions, or in antigen-binding sites, as long they do not adversely affect the properties of the antibody. Substitutions may be made to improve antibody properties, for example stability or affinity. Conservative substitutions will produce molecules having functional and chemical characteristics similar to those molecules into which such modifications are made. Exemplary amino acid substitutions are shown in the table below.

TABLE

Exemplary Conservative Substitutions:

| Original Residue | Exemplary Conservative Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Gly | Pro, Ala |
| His | Asn, Gln, Lys, Arg |
| Ile | Leu, Val, Met, Ala, Phe |
| Leu | Ile, Val, Met, Ala, Phe |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

In some embodiments, variants of the proteins and peptides provided herein are provided. In some embodiments, a variant comprises a substitution, deletions, or insertion. In some embodiments, the variant comprises 1, 2, 3, 4, 5, 6, 7, 8, 9, or 10 (e.g., 1-10) substitutions. As described herein, the substitutions can be conservative substitutions. In some embodiments, the substitution is non-conservative. In some embodiments, the variant comprises 1, 2, 3, 4, 5, 6, 7, 8, 9, or 10 (e.g., 1-10) deletions. In some embodiments, the variant comprises 1, 2, 3, 4, 5, 6, 7, 8, 9, or 10 (e.g., 1-10) insertions. In some embodiments, the substitutions, deletions, or insertions are present in the CDRs provided for herein. In some embodiments, the substitutions, deletions, or insertions are not present in the CDRs provided for herein.

The term "in combination with" as used herein means that the described agents can be administered to an animal or subject together in a mixture, concurrently as single agents or sequentially as single agents in any order.

The techniques to raise antibodies to small peptide sequences that recognize and bind to those sequences in the free or conjugated form or when presented as a native sequence in the context of a large protein are well known in the art. Such antibodies include murine, murine-human and human-human antibodies produced by hybridoma or recombinant techniques known in the art. Antibodies can also be produced in human, a mouse, sheep, a rat, a rabbit, a shark, a llama, or a chicken. In some embodiments, the antibody is produced in a chicken. The antibodies can also be produced in or other small animals.

The term "epitope" is meant to refer to that portion of any molecule capable of being recognized by and bound by an antibody at one or more of the Ab's antigen binding regions. Epitopes usually consist of chemically active surface groupings of molecules such as amino acids or sugar side chains and have specific three dimensional structural characteristics as well as specific charge characteristics. Example of epitopes include, but are not limited to, the residues described herein that form GLUT4 epitopes. In some embodiments, the epitope is only present in a non-denatured protein. In some embodiments, the epitope is only present in a denatured protein.

In some embodiments, the source for the DNA encoding a non-human antibody include cell lines which produce antibody, such as hybrid cell lines commonly known as hybridomas.

The hybrid cells are formed by the fusion of a non-human antibody-producing cell, typically a spleen cell of an animal immunized against either natural or recombinant antigen, or a peptide fragment of the antigen protein sequence. Alternatively, the non-human antibody-producing cell can be a B lymphocyte obtained from the blood, spleen, lymph nodes or other tissue of an animal immunized with the antigen.

The second fusion partner, which provides the immortalizing function, can be a lymphoblastoid cell or a plasmacytoma or myeloma cell, which is not itself an antibody producing cell, but is malignant. Fusion partner cells include, but are not limited to, the hybridoma SP2/0-Ag14, abbreviated as SP2/0 (ATCC CRL1581) and the myeloma P3X63Ag8 (ATCC TIB9), or its derivatives. See, e.g., Ausubel infra, Harlow infra, and Colligan infra, the contents of which references are incorporated entirely herein by reference.

The antibodies can be generated according the examples provided herein. Once the sequences are known, the antibodies can also be generated according to known methods. The antibodies can also be converted to different types, such as being converted to Human IgGs and the like. By converting the antibodies to a human antibody, a human subject should not identify the antibodies as foreign. The conversion of a non-human IgG antibody to a human IgG antibody is well known and can routinely be done once the native sequence is known. As discussed herein, the antibodies can be modified according to known methods. Such methods are described in, for example, Riechmann L, Clark M, Waldmann H, Winter G (1988). Reshaping human antibodies for therapy". Nature 332 (6162): 332-323; Tsurushita N, Park M, Pakabunto K, Ong K, Avdalovic A, Fu H, Jia A, Vasquez M, Kumar S. (2004); and "Humanization of a chicken anti-IL-12 monoclonal antibody" Immunol Methods 295 (1-2): 9-19; Nishibori N, Horiuchi H, Furusawa S, Matsuda H. (2006) "Humanization of chicken monoclonal antibody using phage display system" Mol Immunol. 43 (6): 634-42, each of which is incorporated by reference in its entirety.

The antibody-producing cell contributing the nucleotide sequences encoding the antigen-binding region of the chimeric antibody can also be produced by transformation of a non-human, such as a primate, or a human cell. For example, a B lymphocyte which produces the antibody can be infected and transformed with a virus such as Epstein-Barr virus to yield an immortal antibody producing cell (Kozbor et al., Immunol. Today 4:72 79 (1983)). Alternatively, the B lymphocyte can be transformed by providing a transforming gene or transforming gene product, as is well-known in the art. See, e.g, Ausubel infra, Harlow infra, and Colligan infra, the contents of which references are incorporated entirely herein by reference. The cell fusions are accomplished by standard procedures well known to those skilled in the field of immunology. Fusion partner cell lines and methods for fusing and selecting hybridomas and screening for mAbs are well known in the art. See, e.g, Ausubel infra, Harlow infra, and Colligan infra, the contents of which references are incorporated entirely herein by reference.

In some embodiments, the antibody is a MAb which binds to GLUT4. In some embodiments, the antibody binds to amino acids of an epitope of the GLUT4. The epitopes are described herein, such as in the Tables provided in the figures and described in the Examples. In some embodiments, the antibody binds specifically to the proteins and antigens described herein.

In some embodiments, the antibody comprises a sequence as provided for herein.

The sequences of the antibodies can be modified to yield human IgG antibodies. The conversion of the sequences provided herein can be modified to yield other types of antibodies. The CDRs can also be linked to other antibodies, proteins, or molecules to create antibody fragments that bind to GLUT4. The CDRs and antibody sequences provided herein also be humanized or made fully human according to known methods. The sequences can also be made into chimeric antibodies as described herein.

In some embodiments, the antibody comprises an amino acid sequence comprising a sequence provided for herein or a fragment thereof. In some embodiments, the antibody comprises one or more amino acid sequences as provided herein, an antigen binding fragments, thereof, or a human IgG variant thereof. "A human IgG variant thereof" refers to an antibody that has been modified to be a human IgG when the starting antibody is not a human IgG antibody.

As described herein the production of antibodies with a known sequence is routine and can be done by any method. Accordingly, in some embodiments, a nucleic acid encoding an antibody or fragment thereof is provided. In some embodiments, the nucleic acid encodes a sequence provided for herein. The antibodies can also be modified to be chimeric antibodies or human antibodies. The antibodies can also be used in injectable pharmaceutical compositions. As also described herein, the antibodies can be isolated antibodies or engineered antibodies.

In some embodiments, "derivatives" of the antibodies, fragments, regions or derivatives thereof, which term includes those proteins encoded by truncated or modified genes to yield molecular species functionally resembling the immunoglobulin fragments are provided. The modifications include, but are not limited to, addition of genetic sequences coding for cytotoxic proteins such as plant and bacterial toxins. The modification can also include a reporter protein, such as a fluorescent or chemiluminescent tag. The fragments and derivatives can be produced in any manner.

The identification of these antigen binding region and/or epitopes recognized by Abs described herein provide the information necessary to generate additional monoclonal antibodies with similar binding characteristics and therapeutic or diagnostic utility that parallel the embodiments of this application.

The nucleic acid sequence encoding an antibody described herein can be genomic DNA or cDNA, or RNA (e.g. mRNA) which encodes at least one of the variable regions described herein. A convenient alternative to the use of chromosomal gene fragments as the source of DNA encoding the V region antigen-binding segment is the use of cDNA for the construction of chimeric immunoglobulin genes, e.g., as reported by Liu et al. (Proc. Natl. Acad. Sci., USA 84:3439 (1987) and J. Immunology 139:3521 (1987), which references are hereby entirely incorporated herein by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

For example, a cDNA encoding a V region antigen-binding segment able to detect, bind, to or neutralize a GLUT4 antigen can be provided using known methods based on the use of the amino acid sequences provided herein. Because the genetic code is degenerate, more than one codon can be used to encode a particular amino acid (Watson, et al., infra). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic or prokaryotic cells expressing an antibody or fragment. Such "codon usage rules" are disclosed by Lathe, et al., J. Molec. Biol. 183:1 12 (1985). Using the "codon usage rules" of Lathe, a single oligonucleotide, or a set of oligonucleotides, that contains a theoretical "most probable" nucleotide sequence capable of encoding an antibody variable or constant region sequences is identified.

The variable regions described herein can be combined with any type of constant region including a human constant region or murine constant region. Human genes which encode the constant (C) regions of the antibodies, fragments and regions can be derived from a human fetal liver library, by known methods. Human C regions genes can be derived from any human cell including those which express and produce human immunoglobulins. The human $C_H$ region can be derived from any of the known classes or isotypes of human H chains, including gamma, μ, α, δ or ε, and subtypes thereof, such as G1, G2, G3 and G4. Since the H chain isotype is responsible for the various effector functions of an antibody, the choice of $C_H$ region will be guided by the desired effector functions, such as complement fixation, or activity in antibody-dependent cellular cytotoxicity (ADCC). Preferably, the $C_H$ region is derived from gamma 1 (IgG1), gamma 3 (IgG3), gamma 4 (IgG4), or μ (IgM). The human $C_L$ region can be derived from either human L chain isotype, kappa or lambda. In some embodiments, the antibody comprises a Fc domain. In some embodiments, the Fc domain comprises a mutation to extend the half-life of the antibody. In some embodiments, the Fc domain comprises a mutation such as those described in U.S. Pat. No. 7,670,600, which is hereby incorporated by reference in its entirety. In some embodiment, the constant region comprises a mutation at position at amino acid residue 428 relative to a wild-type human IgG constant domain, numbered according to the EU numbering index of Kabat. Without being bound to any particular theory, an antibody comprising a mutation that corresponds to residue 428 can have an increased half-life compared to the half-life of an IgG having the wild-type human IgG constant domain. In some embodiments, the mutation is a substitution of the native residue with a threonine, leucine, phenylalanine or serine. In some embodiments, the antibody further comprises one or more amino acid substitutions relative to the corresponding wild-type human IgG constant domain at one or more of amino acid residues 251-256, 285-290, 308-314, 385-389, and 429-436, numbered according to the Kabat EU numbering index. The specific mutations or substitutions at these positions are described in U.S. Pat. No. 7,670,600, which is hereby incorporated by reference in its entirety.

Genes encoding human immunoglobulin C regions can be obtained from human cells by standard cloning techniques (Sambrook, et al. (Molecular Cloning: A Laboratory Manual, 2nd Edition, Cold Spring Harbor Press, Cold Spring Harbor, N.Y. (1989) and Ausubel et al., eds. Current Protocols in Molecular Biology (1987 1993)). Human C region genes are readily available from known clones containing genes representing the two classes of L chains, the five classes of H chains and subclasses thereof. Chimeric antibody fragments, such as F(ab')$_2$ and Fab, can be prepared by designing a chimeric H chain gene which is appropriately truncated. For example, a chimeric gene encoding an H chain portion of an F(ab')$_2$ fragment would include DNA sequences encoding the CH$_1$ domain and hinge region of the H chain, followed by a translational stop codon to yield the truncated molecule.

In some embodiments, the antibodies, murine, human, humanized, or chimeric antibodies, fragments and regions of the antibodies described herein are produced by cloning DNA segments encoding the H and L chain antigen-binding regions of a GLUT4 antigen specific antibody, and joining these DNA segments to DNA segments encoding $C_H$ and $C_L$ regions, respectively, to produce murine, human or chimeric immunoglobulin-encoding genes.

Thus, in some embodiments, a fused chimeric gene is created which comprises a first DNA segment that encodes at least the antigen-binding region of non-human origin, such as a functionally rearranged V region with joining (J) segment, linked to a second DNA segment encoding at least a part of a human C region.

Therefore, cDNA encoding the antibody V and C regions, the method of producing the antibody according to some of the embodiments described herein involve several steps, as exemplified below: 1. isolation of messenger RNA (mRNA) from the cell line producing an anti-GLUT4 antigen antibody and from optional additional antibodies supplying heavy and light constant regions; cloning and cDNA production therefrom; 2. preparation of a full length cDNA library from purified mRNA from which the appropriate V and/or C region gene segments of the L and H chain genes can be: (i) identified with appropriate probes, (ii) sequenced, and (iii) made compatible with a C or V gene segment from another antibody for a chimeric antibody; 3. Construction of complete H or L chain coding sequences by linkage of the cloned specific V region gene segments to cloned C region gene, as described above; 4. Expression and production of L and H chains in selected hosts, including prokaryotic and eukaryotic cells to provide murine-murine, human-murine, human-human or human murine antibodies.

Two coding DNA sequences are said to be "operably linked" if the linkage results in a continuously translatable sequence without alteration or interruption of the triplet reading frame. A DNA coding sequence is operably linked to a gene expression element if the linkage results in the proper function of that gene expression element to result in expression of the coding sequence.

As used herein and unless otherwise indicated, the term "about" is intended to mean±5% of the value it modifies. Thus, about 100 means 95 to 105.

In some embodiments, the antibodies described herein are used to detect the presence of the antigen. The present antibody can be used in any device or method to detect the presence of the antigen.

The term "purified" with referenced to an antibody refers to an antibody that is substantially free of other material that associates with the molecule in its natural environment. For instance, a purified protein is substantially free of the cellular material or other proteins from the cell or tissue from which it is derived. The term refers to preparations where the isolated protein is sufficiently pure to be analyzed, or at least 70% to 80% (w/w) pure, at least 80%-90% (w/w) pure, 90-95% pure; and, at least 95%, 96%, 97%, 98%, 99%, or 100% (w/w) pure. In some embodiments, the antibody is purified.

As an alternative to preparing monoclonal antibody-secreting hybridomas, a monoclonal antibody to a polypeptide may be identified and isolated by screening a recombinant combinatorial immunoglobulin library (e.g., an antibody phage display library) with a polypeptide described herein to thereby isolate immunoglobulin library members that bind to the polypeptide. Techniques and commercially available kits for generating and screening phage display libraries are well known to those skilled in the art. Additionally, examples of methods and reagents particularly amenable for use in generating and screening antibody or antigen binding protein display libraries can be found in the literature. Thus, the epitopes described herein can be used to screen for other antibodies that can be used therapeutically, diagnostically, or as research tools.

Antibody Conjugates

The antibodies provided for herein may also be conjugated to a chemical moiety. The chemical moiety may be, inter alia, a polymer, a radionuclide or a cytotoxic factor. In particular embodiments, the chemical moiety is a polymer which increases the half-life of the antibody molecule in the body of a subject. Suitable polymers include, but are not limited to, polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (Bioconj. Chem. 10:973-981) discloses PEG conjugated single-chain antibodies. Wen, et al., (2001) (Bioconj. Chem. 12:545-553) disclose conjugating antibodies with PEG which is attached to a radiometal chelator (diethylenetriaminpentaacetic acid (DTPA)).

The antibodies and antibody fragments of the invention may also be conjugated with labels such as $^{99}$Tc, $^{90}$Y, $^{111}$In, $^{32}$P, $^{14}$C, $^{125}$I, $^{3}$H $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr and $^{56}$Fe.

The antibodies and antibody fragments of the invention may also be conjugated with fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibody molecules may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *Momordica charantia* inhibitor, curcin, crotin, *Saponaria officinalis* inhibitor, mitogellin, restrictocin, phenomycin, and enomycin.

Any method known in the art for conjugating the antibody molecules of the invention to the various moieties may be employed, including those methods described by Hunter, et al., (1962) Nature 144:945; David, et al., (1974) Biochemistry 13:1014; Pain, et al., (1981) J. Immunol. Meth. 40:219; and Nygren, J., (1982) Histochem. and Cytochem. 30:407. Methods for conjugating antibodies are conventional and very well known in the art.

In some embodiments, antibodies (e.g. an anti-GLUT4 antibody) are provided herein. In some embodiments, the antibody is a recombinant antibody that binds to a GLUT4 protein. In some embodiments, the GLUT4 protein is a human GLUT4 protein. In some embodiments, the GLUT4 protein that is recognized by the antibodies is in its native conformation (non-denatured) conformation. In some embodiments, the antibody does not specifically binds to a denatured GLUT4 protein. As used herein, the term "recombinant antibody" refers to an antibody that is not naturally occurring. In some embodiments, the term "recombinant antibody" refers to an antibody that is not isolated from a human subject.

In some embodiments, the antibody comprises one or more peptides having the following sequences, or a variant thereof:

| SEQ ID NO: | AB ID NO. | Sequence |
|---|---|---|
| 2 | AB101 | ALTQPSSVSANPGETVKITCSGSSNSYGWYQQKSP GSAPVTVIYYNDKRPSDIPSRFSGSKSDSTHTLTIT GVRAEDEAVYFCGSYDSTYVGIFGAGTTLTVLGQ SSRSSGGGGSSGGGGSAVTLDESGGGLQTPGGTLS LVCKASGFTFSSNAMGWVRQAPGKGLEWVAGIS SDGRYTKYGSAVKGRATISRDNGQSTVRLQLNNL RAEDTGTYFCAKAFGNNYRRIYAGQIDAWGHGT EVIVSS |
| 3 | AB102 | ALTQPSSVSANLGGTVKITCSGGGSYGYGWYQQK SPGSAPVTVIYSNDQRPSDIPSRFSGSKSGSTATLTI |

-continued

| SEQ ID NO: | AB ID NO. | Sequence |
|---|---|---|
| | | TGVRAEDEAIYYCGSTDSDYVGIFGAGTTLTVLG QSSRSSGGGGSSGGGGSAVTLDESGGGLQTPGGT LSLVCKASGFDFSSYATIWVRQAPGKGLEWVAGI SGTGTGSSTGYAPAVKGRATISRDNGQSTVRLQL NNLRAEDTGSYFCAKSTGYGDSWIYPDSIDAWGH GTEVIVSS |
| 4 | AB105 | ALTQPSSVSANPGETVEITCSGDSSYYGWYQQKSP GSAPVTVIYANTNRPSDIPSRFSGSASGSTATLTIT GVQAEDEAVYYCGSADSTYAGIFGAGTTLTVLGQ SSRSSGGGGSSGGGGSAVTLDESGGGLQTPGGAL SLICKASGFTFSSYTMNWVRQAPGKGLEWVGVIS NSGRTTNYGAAVQGRATISRDNGQSTVRLQLNNL RAEDTGTYYCAKSSASASCAWWAGRSYPCSANRI DAWGHGTEVIVSS |
| 5 | AB108 | ALTQPSSVSANLGGTVKITCSGSSGSYGWYQQKA PGSAPVTLIYRNDKRPSDIPSRFSGSESGSTGTLTIT GVQAEDEAVYFCGGYDSSAGYAAFGAGTTLTVL GQSSRSSGGGGSSGGGGSAVTLDESGGGLQTPGG ALSLVCKASGFTFSSHGMGWVRQAPGKGLEWVG SISTGRYTFYAPAVKGRATISRDNGQSTLRLQLNN LRAEDTGTYYCTKCAGLNGCGGGEIDAWGHGTE VIVSS |
| 6 | AB111 | ALTQPSSVSANPGETVKITCSGSGSWYGWFQQKS PGSAPVTVIYSNDKRPSDIPSRFSGSKSGSTSTLTIT GVQVEDEAVYYCGNWDIFGAGTTLTVLGQSSRSS GGGGSSGGGGSAVTLDESGGGLQTPGGALSLVCK ASGFTFSSHGMGWVRQAPGKGLEWVASISTGRYT FYAPAVKGRATISRDNGQSTVRLQLNNLRAEDTA TYYCTKCAGLNGCGGGEIDAWGHGTEVIVSS |

Each of the sequences provided in this table is in a scFv format where the V$_H$ and VL regions are linked with a peptide linker. The peptide linker illustrated in the table is is just one example of a linker that is capable of being used. The linker may be substituted with other peptide linkers. Examples of other peptide linkers that can be used to link various peptides provided for herein include, but are not limited to: GQSSRSSGGGGSSGGGGS (SEQ ID NO: 120); (GGGGS)$_n$ (SEQ ID NO: 121); (GGGGA)$_n$ (SEQ ID NO: 122), or any combination thereof, wherein each n is independently 1-5. The linker of GQSSRSSGGGGSSGGGGS illustrated in SEQ ID NOs: 3-6 can be substituted with any of these linkers or combinations of linkers. In some embodiments, the variable regions are not linked with a peptide linker.

In some embodiments, an antibody, or antigen binding fragment thereof is provided, wherein the antibody or antibody fragment comprises a peptide selected from the following table.

| Ab ID No | LCDR1 | LCDR2 | LCDR3 | HCDR1 | HCDR2 | HCDR3 |
|---|---|---|---|---|---|---|
| AB101 | CSGSSN SYG (SEQ ID NO: 18) | IYYNDKRP (SEQ ID NO: 19) | CGSYDSTYVG IF (SEQ ID NO: 20) | GFTFSSNA MGWV (SEQ ID NO: 21) | VAGISSDGRYTKYG (SEQ ID NO: 22) | CAKAFGNNYR RIYAGQIDA (SEQ ID NO: 23) |
| AB102 | CSGGGS YGYG (SEQ ID NO: 24) | IYSNDQRP (SEQ ID NO: 25) | CGSTDSDYVG IF (SEQ ID NO: 26) | GFDFSSYA TIWV (SEQ ID NO: 27) | VAGISGTGIGSSTG YA (SEQ ID NO: 28) | CAKSTGYGDS WIYPDSIDA (SEQ ID NO: 29) |
| AB103 | CSGSSS GYG (SEQ ID NO: 30) | IYNSNKRP (SEQ ID NO: 31) | CGNRDSTNSA GIF (SEQ ID NO: 32) | GFTFSDYG MGWV (SEQ ID NO: 33) | VAAITSSGRYTYYG (SEQ ID NO: 34) | CAKTTSTCAS CVAYSIDA (SEQ ID NO: 35) |
| AB104 | CSGGGS YYG (SEQ ID NO: 36) | IYYNDKRP (SEQ ID NO: 37) | CGSWDSSTNT AF (SEQ ID NO: 38) | GFTFSSHG MGWV (SEQ ID NO: 39) | VASISTGRYTFYA (SEQ ID NO: 40) | CTKCAGLNGC GGGEIDA (SEQ ID NO: 41) |

-continued

| Ab ID No | LCDR1 | LCDR2 | LCDR3 | HCDR1 | HCDR2 | HCDR3 |
|---|---|---|---|---|---|---|
| AB105 | CSGDSSYYG (SEQ ID NO: 42) | IYANTNRP (SEQ ID NO: 43) | CGSADSTYAGIF (SEQ ID NO: 44) | GFTFSSYTMNWV (SEQ ID NO: 45) | VGVISNSGRTTNYG (SEQ ID NO: 46) | CAKSSASASCAWWAGRSYPCSANRIDA (SEQ ID NO: 47) |
| AB106 | CSGGGSYG (SEQ ID NO: 48) | IYGNDKRP (SEQ ID NO: 49) | CGSYEDSSA (SEQ ID NO: 50) | GFTFSSHGMGWV (SEQ ID NO: 51) | VASISTGRYTFYA (SEQ ID NO: 52) | CTKCAGLNGCGGGEIDA (SEQ ID NO: 53) |
| AB107 | CSGGYSGCGYG (SEQ ID NO: 54) | IYDNTNRP (SEQ ID NO: 55) | CGSADSISYNDYVG (SEQ ID NO: 56) | GFSFSGYGMGWV (SEQ ID NO: 57) | VAGIDYSGGGTEYG (SEQ ID NO: 58) | CTKCAYSSGWCGDSIDA (SEQ ID NO: 59) |
| AB108 | CSGSSGSYG (SEQ ID NO: 60) | IYRNDKRP (SEQ ID NO: 61) | CGGYDSSAGYAAF (SEQ ID NO: 62) | GFTFSSHGMGWV (SEQ ID NO: 63) | VGSISTGRYTFYA (SEQ ID NO: 64) | CTKCAGLNGCGGGEIDA (SEQ ID NO: 65) |
| AB109 | CSGGGSWYG (SEQ ID NO: 66) | IYSNNKRP (SEQ ID NO: 67) | CGSRDSSTYVGIF (SEQ ID NO: 68) | GFTFSSYTMQWV (SEQ ID NO: 69) | VAAITSSGRYTGYG (SEQ ID NO: 70) | CARGGSVDKIDA (SEQ ID NO: 71) |
| AB110 | CSGSSSGSYG (SEQ ID NO: 72) | IYYNDKRP (SEQ ID NO: 73) | CGSYDSSAGYVGIF (SEQ ID NO: 74) | GFTFSSYTMQWV (SEQ ID NO: 75) | VAGIGSSSYTYFG (SEQ ID NO: 76) | CAKGASATWSYAYIASRIGA (SEQ ID NO: 77) |
| AB111 | CSGSGSWYG (SEQ ID NO: 78) | IYSNDKRP (SEQ ID NO: 79) | CGNWDIF (SEQ ID NO: 80) | GFTFSSHGMGWV (SEQ ID NO: 81) | VASISTGRYTFYA (SEQ ID NO: 82) | CTKCAGLNGCGGGEIDA (SEQ ID NO: 83) |
| AB112 | CSGGSNNYG (SEQ ID NO: 84) | IYRNDKRP (SEQ ID NO: 85) | CGGYDSSNYVAVF (SEQ ID NO: 86) | GFTFSSHGMGWV (SEQ ID NO: 87) | VASISTGRYTFYA (SEQ ID NO: 88) | CTKCAGLNGCGGGEIDA (SEQ ID NO: 89) |
| AB113 | CSGSSGSSYG (SEQ ID NO: 90) | IYRNTQRP (SEQ ID NO: 91) | CGAVDSTGGAF (SEQ ID NO: 92) | GFTFNDYGMAWV (SEQ ID NO: 93) | VASISTGRYTFYA (SEQ ID NO: 94) | CTKCAGLNGCGGGEIDA (SEQ ID NO: 95) |
| AB114 | CSGGSNNYG (SEQ ID NO: 96) | IYANTKRP (SEQ ID NO: 97) | CGSADSRAGIF (SEQ ID NO: 98) | GFTFSSHGMGWV (SEQ ID NO: 99) | VASISTGRYTFYA (SEQ ID NO: 100) | CTKCAGLNGCGGGEIDV (SEQ ID NO: 101) |

In some embodiments, an antibody, or antibody binding fragment thereof, comprises a light chain CDR having a sequence of SEQ ID NO: 18, 19, 20, 24, 25, 26, 30, 31, 32, 36, 37, 38, 42, 43, 44, 48, 49, 50, 54, 55, 56, 60, 61, 62, 66, 67, 68, 72, 73, 74, 78, 79, 80, 84, 85, 86, 90, 91, 92, 96, 97, or 98. In some embodiments, an antibody, or antibody binding fragment thereof, comprises a light chain CDR1 having a sequence of SEQ ID NO: 18, 24, 30, 36, 42, 48, 54, 60, 66, 72, 78, 84, 90, or 96. In some embodiments, an antibody, or antibody binding fragment thereof, comprises a light chain CDR2 having a sequence of SEQ ID NO: 19, 25, 31, 37, 43, 49, 55, 61, 67, 73, 79, 85, 91, or 97. In some embodiments, an antibody, or antibody binding fragment thereof, comprises a light chain CDR3 having a sequence of SEQ ID NO: 20, 26, 32, 38, 44, 50, 56, 62, 68, 74, 80, 86, 92, or 98.

In some embodiments, an antibody, or antibody binding fragment thereof, comprises a heavy chain CDR having a sequence of SEQ ID NO: 21, 22, 23, 27, 28, 29, 33, 34, 35, 39, 40, 41, 45, 46, 47, 51, 52, 53, 57, 58, 59, 63, 64, 65, 69, 70, 71, 75, 76, 77, 81, 82, 83, 87, 88, 89, 93, 94, 95, 99, 100, or 101. In some embodiments, an antibody, or antibody binding fragment thereof, comprises a heavy chain CDR1 having a sequence of SEQ ID NO: 21, 27, 33, 39, 45, 51, 57, 63, 69, 75, 81, 87, 93, or 99. In some embodiments, an antibody, or antibody binding fragment thereof, comprises a heavy chain CDR2 having a sequence of SEQ ID NO: 22, 28, 34, 40, 46, 52, 58, 64, 70, 76, 82, 88, 94, or 100. In some embodiments, an antibody, or antibody binding fragment thereof, comprises a light chain CDR3 having a sequence of SEQ ID NO: 23, 29, 35, 41, 47, 53, 59, 65, 71, 77, 83, 89, 95, or 101.

The different CDR proteins can be combined in any combination including those not depicted in the table above. For example In some embodiments, an antibody, or antigen binding fragment thereof, comprises:
(i) a heavy chain variable region comprising heavy chain CDR1, CDR2, and CDR3 sequences, wherein the heavy chain CDR1 sequence has the amino acid sequence of 21, 27, 33, 39, 45, 51, 57, 63, 69, 75, 81, 87, 93, or 99; the heavy chain CDR2 has the amino acid sequence of 22, 28, 34, 40, 46, 52, 58, 64, 70, 76, 82, 88, 94, or 100; and the heavy chain CDR3 sequence has the amino acid sequence of SEQ ID NO: 23, 29, 35, 41, 47, 53, 59, 65, 71, 77, 83, 89, 95, or 101; or variants of any of the foregoing; and
(ii) a light chain variable region comprising light chain CDR1, CDR2, and CDR3 sequences, wherein the light chain CDR1 sequence has the amino acid sequence 18, 24, 30, 36, 42, 48, 54, 60, 66, 72, 78, 84, 90, or 96; the light chain CDR2 sequence has the amino acid sequence of 19, 25, 31, 37, 43, 49, 55, 61, 67, 73, 79, 85, 91, or 97, and the light chain CDR3 sequence has the amino acid sequence of 20, 26, 32, 38, 44, 50, 56, 62, 68, 74, 80, 86, 92, or 98; or variants of any of the foregoing.

In some embodiments, an antibody, or antigen binding fragment thereof, comprises:
(i) a heavy chain variable region comprising heavy chain CDR1, CDR2, and CDR3 sequences, wherein the heavy chain CDR1 sequence has the amino acid sequence of SEQ ID NO: 21, the heavy chain CDR2 has the amino acid sequence of SEQ ID NO: 22; and the heavy chain CDR3 sequence has the amino acid sequence of SEQ ID NO: 23; and
(ii) a light chain variable region comprising light chain CDR1, CDR2, and CDR3 sequences, wherein the light chain CDR1 sequence has the amino acid sequence SEQ ID NO: 18; the light chain CDR2 sequence has the amino acid sequence of SEQ ID NO: 19, and the light chain CDR3 sequence has the amino acid sequence of SEQ ID NO: 20.

In some embodiments, an antibody, or antigen binding fragment thereof, comprises:
(i) a heavy chain variable region comprising heavy chain CDR1, CDR2, and CDR3 sequences, wherein the heavy chain CDR1 sequence has the amino acid sequence of SEQ ID NO: 27; the heavy chain CDR2 has the amino acid sequence of SEQ ID NO: 28; and the heavy chain CDR3 sequence has the amino acid sequence of SEQ ID NO: 29; or variants of any of the foregoing; and
(ii) a light chain variable region comprising light chain CDR1, CDR2, and CDR3 sequences, wherein the light chain CDR1 sequence has the amino acid sequence SEQ ID NO: 24; the light chain CDR2 sequence has the amino acid sequence of SEQ ID NO: 25, and the light chain CDR3 sequence has the amino acid sequence of SEQ ID NO: 26; or variants of any of the foregoing.

In some embodiments, an antibody, or antigen binding fragment thereof, comprises:
(i) a heavy chain variable region comprising heavy chain CDR1, CDR2, and CDR3 sequences, wherein the heavy chain CDR1 sequence has the amino acid sequence of SEQ ID NO: 33; the heavy chain CDR2 has the amino acid sequence of SEQ ID NO: 34; and the heavy chain CDR3 sequence has the amino acid sequence of SEQ ID NO: 35; or variants of any of the foregoing; and
(ii) a light chain variable region comprising light chain CDR1, CDR2, and CDR3 sequences, wherein the light chain CDR1 sequence has the amino acid sequence SEQ ID NO: 30; the light chain CDR2 sequence has the amino acid sequence of SEQ ID NO: 31, and the light chain CDR3 sequence has the amino acid sequence of SEQ ID NO: 32; or variants of any of the foregoing.

In some embodiments, an antibody, or antigen binding fragment thereof, comprises:
(i) a heavy chain variable region comprising heavy chain CDR1, CDR2, and CDR3 sequences, wherein the heavy chain CDR1 sequence has the amino acid sequence of SEQ ID NO: 39; the heavy chain CDR2 has the amino acid sequence of SEQ ID NO: 40; and the heavy chain CDR3 sequence has the amino acid sequence of SEQ ID NO: 41; or variants of any of the foregoing; and
(ii) a light chain variable region comprising light chain CDR1, CDR2, and CDR3 sequences, wherein the light chain CDR1 sequence has the amino acid sequence SEQ ID NO: 36; the light chain CDR2 sequence has the amino acid sequence of SEQ ID NO: 37, and the light chain CDR3 sequence has the amino acid sequence of SEQ ID NO: 38; or variants of any of the foregoing.

In some embodiments, an antibody, or antigen binding fragment thereof, comprises:
(i) a heavy chain variable region comprising heavy chain CDR1, CDR2, and CDR3 sequences, wherein the heavy chain CDR1 sequence has the amino acid sequence of SEQ ID NO: 45; the heavy chain CDR2 has the amino acid sequence of SEQ ID NO: 46; and the heavy chain CDR3 sequence has the amino acid sequence of SEQ ID NO: 47; or variants of any of the foregoing; and
(ii) a light chain variable region comprising light chain CDR1, CDR2, and CDR3 sequences, wherein the light chain CDR1 sequence has the amino acid sequence SEQ ID NO: 42; the light chain CDR2 sequence has the amino acid sequence of SEQ ID NO: 43, and the light chain CDR3 sequence has the amino acid sequence of SEQ ID NO: 44; or variants of any of the foregoing.

In some embodiments, an antibody, or antigen binding fragment thereof, comprises:
(i) a heavy chain variable region comprising heavy chain CDR1, CDR2, and CDR3 sequences, wherein the heavy chain CDR1 sequence has the amino acid sequence of SEQ ID NO: 51; the heavy chain CDR2 has the amino acid sequence of SEQ ID NO: 52; and the heavy chain CDR3 sequence has the amino acid sequence of SEQ ID NO: 53; or variants of any of the foregoing; and
(ii) a light chain variable region comprising light chain CDR1, CDR2, and CDR3 sequences, wherein the light chain CDR1 sequence has the amino acid sequence SEQ ID NO: 48; the light chain CDR2 sequence has the amino acid sequence of SEQ ID NO: 49, and the light chain CDR3 sequence has the amino acid sequence of SEQ ID NO: 50; or variants of any of the foregoing.

In some embodiments, an antibody, or antigen binding fragment thereof, comprises:
- (i) a heavy chain variable region comprising heavy chain CDR1, CDR2, and CDR3 sequences, wherein the heavy chain CDR1 sequence has the amino acid sequence of SEQ ID NO: 57; the heavy chain CDR2 has the amino acid sequence of SEQ ID NO: 58; and the heavy chain CDR3 sequence has the amino acid sequence of SEQ ID NO: 59; or variants of any of the foregoing; and
- (ii) a light chain variable region comprising light chain CDR1, CDR2, and CDR3 sequences, wherein the light chain CDR1 sequence has the amino acid sequence SEQ ID NO: 54; the light chain CDR2 sequence has the amino acid sequence of SEQ ID NO: 55, and the light chain CDR3 sequence has the amino acid sequence of SEQ ID NO: 56; or variants of any of the foregoing.

In some embodiments, an antibody, or antigen binding fragment thereof, comprises:
- (i) a heavy chain variable region comprising heavy chain CDR1, CDR2, and CDR3 sequences, wherein the heavy chain CDR1 sequence has the amino acid sequence of SEQ ID NO: 63; the heavy chain CDR2 has the amino acid sequence of SEQ ID NO: 64; and the heavy chain CDR3 sequence has the amino acid sequence of SEQ ID NO: 65; or variants of any of the foregoing; and
- (ii) a light chain variable region comprising light chain CDR1, CDR2, and CDR3 sequences, wherein the light chain CDR1 sequence has the amino acid sequence SEQ ID NO: 60; the light chain CDR2 sequence has the amino acid sequence of SEQ ID NO: 61, and the light chain CDR3 sequence has the amino acid sequence of SEQ ID NO: 62; or variants of any of the foregoing.

In some embodiments, an antibody, or antigen binding fragment thereof, comprises:
- (i) a heavy chain variable region comprising heavy chain CDR1, CDR2, and CDR3 sequences, wherein the heavy chain CDR1 sequence has the amino acid sequence of SEQ ID NO: 69; the heavy chain CDR2 has the amino acid sequence of SEQ ID NO: 70; and the heavy chain CDR3 sequence has the amino acid sequence of SEQ ID NO: 71; or variants of any of the foregoing; and
- (ii) a light chain variable region comprising light chain CDR1, CDR2, and CDR3 sequences, wherein the light chain CDR1 sequence has the amino acid sequence SEQ ID NO: 66; the light chain CDR2 sequence has the amino acid sequence of SEQ ID NO: 67, and the light chain CDR3 sequence has the amino acid sequence of SEQ ID NO: 68; or variants of any of the foregoing.

In some embodiments, an antibody, or antigen binding fragment thereof, comprises:
- (i) a heavy chain variable region comprising heavy chain CDR1, CDR2, and CDR3 sequences, wherein the heavy chain CDR1 sequence has the amino acid sequence of SEQ ID NO: 75; the heavy chain CDR2 has the amino acid sequence of SEQ ID NO: 76; and the heavy chain CDR3 sequence has the amino acid sequence of SEQ ID NO: 77; or variants of any of the foregoing; and
- (ii) a light chain variable region comprising light chain CDR1, CDR2, and CDR3 sequences, wherein the light chain CDR1 sequence has the amino acid sequence SEQ ID NO: 72; the light chain CDR2 sequence has the amino acid sequence of SEQ ID NO: 73, and the light chain CDR3 sequence has the amino acid sequence of SEQ ID NO: 74; or variants of any of the foregoing.

In some embodiments, an antibody, or antigen binding fragment thereof, comprises:
- (i) a heavy chain variable region comprising heavy chain CDR1, CDR2, and CDR3 sequences, wherein the heavy chain CDR1 sequence has the amino acid sequence SEQ ID NO: 81; the heavy chain CDR2 has the amino acid sequence of SEQ ID NO: 82; and the heavy chain CDR3 sequence has the amino acid sequence of SEQ ID NO: 83; or variants of any of the foregoing; and
- (ii) a light chain variable region comprising light chain CDR1, CDR2, and CDR3 sequences, wherein the light chain CDR1 sequence has the amino acid sequence SEQ ID NO: 78; the light chain CDR2 sequence has the amino acid sequence of SEQ ID NO: 79, and the light chain CDR3 sequence has the amino acid sequence of SEQ ID NO: 80; or variants of any of the foregoing.

In some embodiments, an antibody, or antigen binding fragment thereof, comprises:
- (i) a heavy chain variable region comprising heavy chain CDR1, CDR2, and CDR3 sequences, wherein the heavy chain CDR1 sequence has the amino acid sequence of SEQ ID NO: 87; the heavy chain CDR2 has the amino acid sequence of SEQ ID NO: 88; and the heavy chain CDR3 sequence has the amino acid sequence of SEQ ID NO: 89; or variants of any of the foregoing; and
- (ii) a light chain variable region comprising light chain CDR1, CDR2, and CDR3 sequences, wherein the light chain CDR1 sequence has the amino acid sequence SEQ ID NO: 84; the light chain CDR2 sequence has the amino acid sequence of SEQ ID NO: 85, and the light chain CDR3 sequence has the amino acid sequence of SEQ ID NO: 86; or variants of any of the foregoing.

In some embodiments, an antibody, or antigen binding fragment thereof, comprises:
- (i) a heavy chain variable region comprising heavy chain CDR1, CDR2, and CDR3 sequences, wherein the heavy chain CDR1 sequence has the amino acid sequence of SEQ ID NO: 93; the heavy chain CDR2 has the amino acid sequence of SEQ ID NO: 94; and the heavy chain CDR3 sequence has the amino acid sequence of SEQ ID NO: 95; or variants of any of the foregoing; and
- (ii) a light chain variable region comprising light chain CDR1, CDR2, and CDR3 sequences, wherein the light chain CDR1 sequence has the amino acid sequence SEQ ID NO: 90; the light chain CDR2 sequence has the amino acid sequence of SEQ ID NO: 91, and the light chain CDR3 sequence has the amino acid sequence of SEQ ID NO: 92; or variants of any of the foregoing.

In some embodiments, an antibody, or antigen binding fragment thereof, comprises:
- (i) a heavy chain variable region comprising heavy chain CDR1, CDR2, and CDR3 sequences, wherein the heavy chain CDR1 sequence has the amino acid sequence of SEQ ID NO: 99; the heavy chain CDR2 has the amino acid sequence of SEQ ID NO: 100; and the heavy chain CDR3 sequence has the amino acid sequence of SEQ ID NO: 101; or variants of any of the foregoing; and
- (ii) a light chain variable region comprising light chain CDR1, CDR2, and CDR3 sequences, wherein the light chain CDR1 sequence has the amino acid sequence of SEQ ID NO: 96; the light chain CDR2 sequence has the amino acid sequence of SEQ ID NO: 97, and the light chain CDR3 sequence has the amino acid sequence of SEQ ID NO: 98; or variants of any of the foregoing.

In some embodiments, the light chain variable region CDR1 is replaced with any of the other light chain CDR1 sequences. In some embodiments, the light chain variable region CDR2 is replaced with any of the other light chain CDR2 sequences. In some embodiments, the light chain variable region CDR3 is replaced with any of the other light chain CDR3 sequences. In some embodiments, the heavy chain variable region CDR1 is replaced with any of the other light chain CDR1 sequences. In some embodiments, the heavy chain variable region CDR2 is replaced with any of the other light chain CDR2 sequences. In some embodiments, the heavy chain variable region CDR3 is replaced with any of the other light chain CDR3 sequences.

In some embodiments, the an antibody, or antigen binding fragment thereof, or protein is provided that comprises a peptide having a sequence as set forth in any of SEQ ID NOs: 18-101.

In some embodiments, an antibody, or antigen binding fragment thereof, comprises a sequence of, or a variant of any of the following:

| Ab ID | VL Region | VH Region |
|---|---|---|
| AB101 | ALTQPSSVSANPGETVKITCSGSSNSYGWYQQKSPGSAPVTVIYYNDKRPSDIPSRFSGSKSDSTHTLTITGVRAEDEAVYFCGSYDSTYVGIFGAGTTLTVL (SEQ ID NO: 8) | AVTLDESGGGLQTPGGTLSLVCKASGFTFSSNAMGWVRQAPGKGLEWVAGISSDGRYTKYGSAVKGRATISRDNGQSTVRLQLNNLRAEDTGTYFCAKAFGNNYRRIYAGQIDAWGHGTEVIVSS (SEQ ID NO: 13) |
| AB102 | ALTQPSSVSANLGGTVKITCSGGGSYGYGWYQQKSPGSAPVTVIYSNDQRPSDIPSRFSGSKSGSTATLTITGVRAEDEAIYYCGSTDSDYVGIFGAGTTLTVL (SEQ ID NO: 9) | AVTLDESGGGLQTPGGTLSLVCKASGFDFSSYATIWVRQAPGKGLEWVAGISGTGTGSSTGYAPAVKGRATISRDNGQSTVRLQLNNLRAEDTGSYFCAKSTGYGDSWIYPDSIDAWGHGTEVIVSS (SEQ ID NO: 14) |
| AB105 | ALTQPSSVSANPGETVEITCSGDSSYYGWYQQKSPGSAPVTVIYANTNRPSDIPSRFSGSASGSTATLTITGVQAEDEAVYYCGSADSTYAGIFGAGTTLTVL (SEQ ID NO: 10) | AVTLDESGGGLQTPGGALSLICKASGFTFSSYTMNWVRQAPGKGLEWVGVISNSGRTTNYGAAVQGRATISRDNGQSTVRLQLNNLRAEDTGTYYCAKSSASASCAWWAGRSYPCSANRIDAWGHGTEVIVSS (SEQ ID NO: 15) |
| AB108 | ALTQPSSVSANLGGTVKITCSGSSGSYGWYQQKAPGSAPVTLIYRNDKRPSDIPSRFSGSESGSTGTLTITGVQAEDEAVYFCGGYDSSAGYAAFGAGTTLTVL (SEQ ID NO: 11) | AVTLDESGGGLQTPGGALSLVCKASGFTFSSHGMGWVRQAPGKGLEWVGSISTGRYTFYAPAVKGRATISRDNGQSTLRLQLNNLRAEDTGTYYCTKCAGLNGCGGGEIDAWGHGTEVIVSS (SEQ ID NO: 16) |
| AB111 | ALTQPSSVSANPGETVKITCSGSGSWYGWFQQKSPGSAPVTVIYSNDKRPSDIPSRFSGSKSGSTSTLTITGVQVEDEAVYYCGNWDIFGAGTTLTVL (SEQ ID NO: 12) | AVTLDESGGGLQTPGGALSLVCKASGFTFSSHGMGWVRQAPGKGLEWVASISTGRYTFYAPAVKGRATISRDNGQSTVRLQLNNLRAEDTATYYCTKCAGLNGCGGGEIDAWGHGTEVIVSS (SEQ ID NO: 17) |
| AB103 | ALTQPSSVSANPGETVKITCSGSSSGYGYGWYQQKSPGSAPVTVIYNSNKRPSDIPSRFSGSKSGSTGTLTITGVQAEDEAVYFCGNRDSTNSAGIFGAGTTLTVL (SEQ ID NO: 102) | AVTLDESGGGLQTPGGALSLVCKASGFTFSDYGMGWVRQAPGKGLEFVAAITSSGRYTYYGAAVKGRATISRDNGQSTVRLQLNNLRAEDTATYFCAKTTSTCASCVAYSIDAWGHGTEVIVSS (SEQ ID NO: 103) |
| AB104 | ALTQPSSVSANPGETVKITCSGGGSYYGWFQQKSPGSAPVTVIYYNDKRPSNIPSRFSGSKSGSTATLTITGVQAEDEAVYYCGSWDSSTNTAFGAGTTLTVL (SEQ ID NO: 104) | AVTLDESGGGLQTPGGGLSLVCKASGFTFSSHGMGWVRQAPGKGLEWVASISTGRYTFYAPAVKGRATISRDNGQSTVRLQLNNLRAEDTATYYCTKCAGLNGCGGGEIDAWGHGTEVIVSS (SEQ ID NO: 105) |
| AB106 | ALTQPSSVSANLGETVKITCSGGGSYGWYQQKSPGSAPVTLIYGNDKRPSNIPSRFSGSKSGSTHTLTITGVQADDEAVYFCGSYEDSSAGYVGIFGAGTTLTVL (SEQ ID NO: 106) | AVTLDESGGGLQTPGGALSLVCKASGFTFSSHGMGWVRQAPGKGLEWVASISTGRYTFYAPAVKGRATISRDNGQSTVRLQLNNLRAEDTATYYCTKCAGLNGCGGGEIDAWGHGTEVIVSS (SEQ ID NO: 107) |
| AB107 | ALTQPSSVSANPGETVEITCSGGYSGCGYGWYQQKSPGSAPVTVIYDNTNRPSNIPSRFSGSTSGSTATLTITGVQAEDEAVYYCGSADSISYNDYVGIFGAGTTLIVL (SEQ ID NO: 108) | AVTLDESGGGLQTPGGALSLVCKASGFSFSGYGMGWVRQAPGKGLEWVAGIDYSGGGTEYGPAVQGRATISRDNGQSTVRLQLNNLRAEDTAIYFCTKCAYSSGWCGDSIDAWGHGTEVIVSS (SEQ ID NO: 109) |

-continued

| Ab ID | VL Region | VH Region |
|---|---|---|
| AB109 | ALTQPSSVSANPGETVKITCSGGGSW YGWFQQKSPGSAPVTLIYSNNKRPSN IPSRFSGSTSGSTSTLTITGVQADDE AVYFCGSRDSSTYVGIFGAGTTLTVL (SEQ ID NO: 110) | AVTLDESGGGLQTPGGALSLVCKASGF TFSSYTMQWVRQAPGKGLEFVAAITSS GRYTGYGSAVKGRATISRDNGQSTVRL QLNNLRAEDTAIYYCARGGSVDKIDAW GHGTEVIVSS (SEQ ID NO: 111) |
| AB110 | ALTQPSSVSANLGGTVKITCSGSSSG SYGWYQQKSPGSAPVTVIYYNDKRPS DIPSRFSGSKSGSTGTLTITGVQVED EAVYYCGSYDSSAGYVGIFGAGTTLT VL (SEQ ID NO: 112) | AVTLDESGGGLQTPGGALSLVCKASGF TFSSYTMQWVRQAPGKGLEWVAGIGSS SYTYFGPAVKGRATISRDNGQSTVRLQ LNNLRAEDTGTYFCAKGASATWSYAYI ASRIGAWGHGTEVIVSS (SEQ ID NO: 113) |
| AB112 | ALTQPSSVSANLGGTVEITCSGGSNN YGWYQQKSPGSAPVTLIYRNDKRPSD IPSRFAGSTSGSANTLTITGVQGEDE AVYFCGGYDSSNYVAVFGAGTTLTVL (SEQ ID NO: 114) | AVTLDESGGGLQTPGGALSLVCKASGF TFSSHGMGWVRQAPGKGLEWVASISTG RYTFYAPAVKGRATISRDNGQSTVRLQ LNNLRAEDTATYYCTKCAGLNGCGGGE IDAWGHGTEVIVSS (SEQ ID NO: 115) |
| AB113 | ALTQPSSVSANPGETVEITCSGSSGS SYGWYQQKSPGSAPVTVIYRNTQRPS DIPSRFSGSKSGSTGTLTITGVQVED EAVYYCGAVDSTGGAFGAGTTLTVL (SEQ ID NO: 116) | AVTLDESGGGLQTPGGGLSLVCKASGF TFNDYGMAWVRQAPGKGLEWVASISTG RYTFYAPAVKGRATISRDNGQSTVRLQ LNNLRAEDTATYYCTKCAGLNGCGGGE IDAWGHGTEVIVSS (SEQ ID NO: 117) |
| AB114 | ALTQPSSVSANLGGTVEITCSGGSNN YGWYQQKSPGSAPVTLIYANTKRPSD IPSRFSGSKSGSTGTLTITGVQAEDE AVYFCGSADSRAGIFGAGTTLTVL (SEQ ID NO: 118) | AVTLDESGGGLQTPGGALSLVCKASGF TFSSHGMGWVRQAPGKGLEWVASISTG RYTFYAPAVKGRATISRDNGQTTVRLQ LNNLRAEDTGIYYCTKCAGLNGCGGGE IDVWGHGTEVIVSS (SEQ ID NO: 119) |

In some embodiments, the antibody, or antigen binding fragment thereof, comprises a sequence of SEQ ID NOs: 8, 9, 10, 11, 12, 102, 104, 106, 108, 110, 112, 114, 116, or 118, or a variant of any of the foregoing.

In some embodiments, the antibody, or antigen binding fragment thereof, comprises a sequence of SEQ ID NOs: 13, 14, 15, 16, 17, 103, 105, 107, 109, 111, 113, 115, 117, or 119, or a variant of any of the foregoing.

In some embodiments, the antibody, or antigen binding fragment thereof, wherein the antibody has a first sequence comprising a sequence of: SEQ ID NOs: 8, 9, 10, 11, 12, 102, 104, 106, 108, 110, 112, 114, 116, or 118 and a second sequence of SEQ ID NOs: 13, 14, 15, 16, 17, 103, 105, 107, 109, 111, 113, 115, 117, or 119.

In some embodiments, In some embodiments, an antibody, or antigen binding fragment thereof, comprises a $V_L$ sequence of SEQ ID NOs.: 8, 9, 10, 11, 12, 102, 104, 106, 108, 110, 112, 114, 116, or 118, or any combination thereof. The $V_L$ peptide can comprise a variant of any of these sequences as provided for herein.

In some embodiments, an antibody, or antigen binding fragment thereof, comprises a $V_H$ sequence of 13, 14, 15, 16, 17, 103, 105, 107, 109, 111, 113, 115, 117, or 119, or any combination thereof. The $V_H$ peptide can comprise a variant of any of these sequences as provided for herein.

In some embodiments, the antibody, or antigen binding fragment thereof, comprises a sequence of: SEQ ID NO: 8 and SEQ ID NO: 13, SEQ ID NO: 9 and SEQ ID NO: 14, SEQ ID NO: 10 and SEQ ID NO: 15, SEQ ID NO: 11 and SEQ ID NO: 16, or SEQ ID NO: 12 and SEQ ID NO: 17, SEQ ID NO: 102 and SEQ ID NO: 103, SEQ ID NO: 104 and SEQ ID NO: 105, SEQ ID NO: 106 and SEQ ID NO: 107, SEQ ID NO: 108 and SEQ ID NO: 109, SEQ ID NO: 110 and SEQ ID NO: 111, SEQ ID NO: 112 and SEQ ID NO: 113, SEQ ID NO: 114 and SEQ ID NO: 115, SEQ ID NO: 116 and SEQ ID NO: 117, SEQ ID NO: 118 and SEQ ID NO: 119, or any variants thereof. Although these are listed as, for example SEQ ID NO: 8 being first and SEQ ID NO: 13 being second, the peptides can be either N-terminal or C-terminal to one another. For example, the peptide could have a formula of SEQ ID NO: 8 followed by a peptide of SEQ ID NO: 13 or vice versa. There can be intervening sequences between the sequences or on the N or C-terminal portion of the sequences.

In addition to these specific combinations any of the $V_H$ peptides and the $V_L$ peptides can be combined with one another. For example, the antibody, or antigen binding fragment thereof can comprise a sequence of: SEQ ID NO: 8 and SEQ ID NO: 14; SEQ ID NO: 8 and SEQ ID NO: 15; SEQ ID NO: 8 and SEQ ID NO: 16; SEQ ID NO: 8 and SEQ ID NO: 17; SEQ ID NO: 9 and SEQ ID NO: 13, SEQ ID NO: 9 and SEQ ID NO: 15, SEQ ID NO: 9 and SEQ ID NO: 16, SEQ ID NO: 9 and SEQ ID NO: 17, SEQ ID NO: 10 and SEQ ID NO: 13, SEQ ID NO: 10 and SEQ ID NO: 14, SEQ ID NO: 10 and SEQ ID NO: 16, SEQ ID NO: 10 and SEQ ID NO: 17, SEQ ID NO: 11 and SEQ ID NO: 13, SEQ ID NO: 11 and SEQ ID NO: 14, SEQ ID NO: 11 and SEQ ID NO: 15, SEQ ID NO: 11 and SEQ ID NO: 17, SEQ ID NO: 12 and SEQ ID NO: 13, SEQ ID NO: 12 and SEQ ID NO: 14, SEQ ID NO: 12 and SEQ ID NO: 15, or SEQ ID NO: 12 and SEQ ID NO: 16.

Additionally, as provided for herein, the antibodies can be multi-specific antibodies, in that the antibodies have multiple binding regions that target different proteins or the same protein on different epitopes. In some embodiments, the antibody is a bi-specific antibody or a tri-specific antibody.

As provided for herein, the different peptides ($V_H$ or $V_L$) described herein can be linked with a peptide linker or not linked with a peptide linker and instead for a contiguous sequence. In some embodiments, the peptide linker comprises a sequence of GQSSRSSGGGGSSGGGGS (SEQ ID NO: 120); (GGGGS)$_n$ (SEQ ID NO: 121) (GGGGA)$_n$ (SEQ ID NO: 122), or any combination thereof, wherein each n is independently 1-5. The linked peptide format can be represented by a formula of $V_H$-Z-$V_L$ or $V_L$-Z-$V_H$, wherein Z is the peptide linker. In some embodiments, Z is GQSSRSSGGGGSSGGGGS (SEQ ID NO: 120); (GGGGS)$_n$ (SEQ ID NO: 121) (GGGGA)$_n$ (SEQ ID NO: 122), or any combination thereof, wherein each n is independently 1-5.

As provided for herein, the antibodies, or antigen binding fragments thereof can be variants of the sequences.

In some embodiments, a GLUT4 specific antibodies, or antigen binding fragments thereof, that binds to an epitope of GLUT4 comprising residues R265 and G414 is provided. In some embodiments, the antibody, or antigen binding fragments thereof, comprises a heavy chain variable region CDR of CAKSTGYGDSWIYPDSIDA (SEQ ID NO: 29), or a variant thereof. In some embodiments, the antibody comprises a sequence of SEQ ID NO: 9 or SEQ ID NO: 14, or a variant thereof. In some embodiments, the antibody comprises a sequence of SEQ ID NO: 9 and SEQ ID NO: 14, or a variant thereof.

In some embodiments, GLUT4 specific antibodies, or antigen binding fragments thereof, that binds to an inward-open GLUT4 protein are provided. In some embodiments, the inward-open GLUT4 protein is present in a native environment, such as a cell membrane or viral particle. In some embodiments, the inward-open GLUT4 protein that binds to the antibody is not fixed or cross-linked with a chemical agent such as glutaraldehyde or formaldehyde. In some embodiments, the antibody, or antigen binding fragments thereof, comprises a heavy chain variable region CDR CAKSTGYGDSWIYPDSIDA (SEQ ID NO: 29), or a variant thereof. In some embodiments, the antibody, or antigen binding fragments thereof, comprises a sequence of SEQ ID NO: 9 or SEQ ID NO: 14, or a variant thereof. In some embodiments, the antibody, or antigen binding fragments thereof, comprises a sequence of SEQ ID NO: 9 and SEQ ID NO: 14, or a variant thereof. In some embodiments, the peptides of SEQ ID NO: 9 and SEQ ID NO:14 are linked by a peptide linker. In some embodiments, the peptide linker is as provided for herein. In some embodiments, the antibody, or antigen binding fragments thereof, comprises a sequence of SEQ ID NO: 3, or a variant thereof.

In some embodiments, antibodies, or antigen binding fragment thereof, that bind to an epitope of GLUT4 comprising residues E315 and G446 are provided. In some embodiments, GLUT inhibitory antibodies, or antigen binding fragments thereof, are provided. In some embodiments, the GLUT4 inhibitory antibodies binds to to an epitope of GLUT4 comprising residues E315 and G446. In some embodiments, antibodies, or antigen binding fragment thereof, comprises a heavy chain variable region CDR of SEQ ID NO:20, or a variant thereof. In some embodiments, antibodies, or antigen binding fragment thereof, comprises a sequence of SEQ ID NO: 10 or SEQ ID NO: 15, or a variant thereof. In some embodiments, antibodies, or antigen binding fragment thereof, comprises a sequence of SEQ ID NO: 10 and SEQ ID NO: 15, or a variant thereof. In some embodiments, the peptides of SEQ ID NO: 10 and SEQ ID NO: 15 are linked by a peptide linker. In some embodiments, the peptide linker is as provided for herein.

In some embodiments, antibodies, or antigen binding fragment thereof, that specifically bind to an outward-open form of GLUT4 are provided. In some embodiments, the outward-open GLUT4 protein is present in a native environment, such as a cell membrane or viral particle. In some embodiments, the outward-open GLUT4 protein that binds to the antibody is not fixed or cross-linked with a chemical agent such as glutaraldehyde or formaldehyde. In some embodiments, antibodies, or antigen binding fragment thereof, comprises a heavy chain variable region CDR of SEQ ID NO: 20, or a variant thereof. In some embodiments, antibodies, or antigen binding fragment thereof, comprises a sequence of: SEQ ID NO: 10 or SEQ ID NO: 15, or a variant thereof. In some embodiments, antibodies, or antigen binding fragment thereof, comprises a sequence of: SEQ ID NO: 10 and SEQ ID NO: 15, or a variant thereof. In some embodiments, antibodies, or antigen binding fragment thereof, comprises a peptide linker sequence linking the peptide of SEQ ID NO: 10 and the peptide of SEQ ID NO: 15. The linker can be, for example, as provided herein.

In some embodiments, antibodies, or antigen binding fragment thereof, that bind to an epitope of GLUT4 comprising residues L61, G65, and P66 of GLUT4 are provided. In some embodiments, the antibodies, or antigen binding fragment thereof, comprises a heavy chain variable region CDR of SEQ ID NO: 21, or a variant thereof. In some embodiments, the antibodies, or antigen binding fragment thereof, comprises a sequence of SEQ ID NO: 11 or SEQ ID NO: 16, or a variant thereof. In some embodiments, antibodies, or antigen binding fragment thereof, comprises a sequence of SEQ ID NO: 11 and SEQ ID NO: 16, or a variant thereof. In some embodiments, antibodies, or antigen binding fragment thereof, comprises a peptide linker sequence linking the peptide of SEQ ID NO: 11 and the peptide of SEQ ID NO: 16. The linker can be as provided for herein.

In some embodiments, antibodies, or antigen binding fragment thereof, that bind to an epitope of GLUT4 comprising residue G65 of GLUT4. In some embodiments, the antibody that binds to an epitope comprising residue G65 does not bind to the same epitope that is made by the residues of L61, G65, and P66. In some embodiments, the antibodies, or antigen binding fragments thereof, comprises a CDR of SEQ ID NO: 21, or a variant thereof. In some embodiments, the antibodies, or antigen binding fragments thereof, comprises a sequence of SEQ ID NO: 12 or SEQ ID NO: 17, or a variant thereof. In some embodiments, the antibodies, or antigen binding fragments thereof, comprises a sequence of SEQ ID NO: 12 and SEQ ID NO: 17, or a variant thereof. In some embodiments, the antibodies, or antigen binding fragments thereof, comprises a peptide linker sequence linking the peptide of SEQ ID NO: 12 and the peptide of SEQ ID NO: 17. The linker can be as provided for herein.

Also provided herein are mutant GLUT4 proteins. In some embodiments, the mutant GLUT4 protein comprises any of the mutations provided herein. In some embodiments, the GLUT4 mutant protein is locked in conformational state. In some embodiments, the conformational state is outward-open or inward open. In some embodiments, the protein comprises a sequence of SEQ ID NO: 1, and a mutation at positions E345 or Y309. In some embodiment, the protein comprises a sequence of SEQ ID NO:1 with a E345Q and/or Y3091 mutation.

Pharmaceutical Compositions

In some embodiments, to prepare pharmaceutical or sterile compositions of the anti-GLUT4 antibodies or other proteins provided herein, the antibody or antigen binding fragment thereof or other proteins provided herein are admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) Goodman and *Gilman's The Pharmacological Basis of Therapeutics*, McGraw-Hill, New York, N.Y.; Gennaro (2000) *Remington: The Science and Practice of Pharmacy, Lippincott, Williams, and Wilkins*, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.). In some embodiments embodiment, the antibodies are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antibody compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}$/EDO. In particular aspects, antibodies exhibiting high therapeutic indices are desirable. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In some embodiments, a composition of the invention is administered to a subject in accordance with the Physicians' Desk Reference 2003 (Thomson Healthcare; 57th edition (Nov. 1, 2002)).

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In some embodiments, the antibody or antigen binding fragment thereof can be administered by an invasive route such as by injection. In some embodiments, the antibodies or antigen binding fragment thereof, or pharmaceutical composition thereof, is administered intravenously, subcutaneously, intramuscularly, intraarterially, intra-articularly (e.g. in arthritis joints), intratumorally, or by inhalation, aerosol delivery. Administration by non-invasive routes (e.g., orally; for example, in a pill, capsule or tablet) is also within the scope of the present embodiments.

In some embodiments, the anti-GLUT4 antibody, or antigen binding fragment thereof, is administered in combination with at least one additional therapeutic agent, such as, but not limited to insulin, pramlintide, acarbose, miglitol, metformin, alogliptin, canagliflozin, dapagliflozin, empagliflozin, glipizide, glyburide, linagliptin, pioglitazone, repaglinide, rosiglitazone, saxagliptin, sitagliptin, Bromocriptine, albiglutide, dulaglutide, exenatide, liraglutide, semaglutide, nateglinide, repaglinide, ertugliflozin, glimepiride, glipizide, gliclazide, glyburide, chlorpropamide, tolazamide, tolbutamide, rosiglitazone, pioglitazone, or any combination thereof.

In some embodiments, the anti-GLUT4 antibody, or antigen binding fragment thereof, is administered in combination with at least one additional therapeutic agent, such as, but not limited to a therapeutic used to treat cancer or a condition related to cancer. Examples of such treatments and therapeutics include, but are not limited to, Abemaciclib, Abiraterone Acetate, Abraxane (Paclitaxel Albumin-stabilized Nanoparticle Formulation), ABVD, ABVE, ABVE-PC, AC, Acalabrutinib, AC-T, Actemra (Tocilizumab), Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ameluz (Aminolevulinic Acid Hydrochloride), Amifostine, Aminolevulinic Acid Hydrochloride, Anastrozole, Apalutamide, Aprepitant, Aranesp (Darbepoetin Alfa), Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Asparlas (Calaspargase Pegol-mknl), Atezolizumab, Avastin (Bevacizumab), Avelumab, Axicabtagene Ciloleucel, Axitinib, Azacitidine, Azedra (Iobenguane I 131), Bavencio (Avelumab), BEACOPP, Beleodaq (Belinostat), Belinostat, Bendamustine Hydrochloride, Bendeka (Bendamustine Hydrochloride), BEP, Besponsa (Inotuzumab Ozogamicin), Bevacizumab, Bexarotene, Bicalutamide, BiCNU (Carmustine), Binimetinib, Bleomycin Sulfate, Blinatumomab, Blincyto (Blinatumomab), Bortezomib, Bo sulif (Bo sutinib), Bo sutinib, Braftovi (Encorafenib), Brentuximab Vedotin, Brigatinib, BuMel, Busulfan, Busulfex (Busulfan), Cabazitaxel, Cablivi (Caplacizumab-yhdp), Cabometyx (Cabozantinib-S-Malate), Cabozantinib-S-Malate, CAF, Calaspargase Pegol-mknl, Calquence (Acalabrutinib), Campath (Alemtuzumab), Camptosar (Irinotecan Hydrochloride), Capecitabine, Caplacizumab-yhdp, CAPDX, Carac (Fluorouracil—Topical), Carboplatin, CARBOPLATIN-TAXOL, Carfilzomib, Carmustine, Carmustine Implant, Casodex (Bicalutamide), CEM, Cemiplimab-rwlc, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clofarabine, Clolar (Clofarabine), CMF, Cobimetinib, Cometriq (Cabozantinib-S-Malate), Copanlisib Hydrochloride, COPDAC, Copiktra (Duvelisib), COPP, COPP-ABV, Cosmegen (Dactinomycin), Cotellic (Cobimetinib), Crizotinib, CVP, Cyclophosphamide, Cyramza (Ramucirumab), Cytarabine, Cytarabine Liposome, Cytosar-U (Cytarabine), Dabrafenib, Dacarbazine, Dacogen (Decitabine), Dacomitinib, Dactinomycin, Daratumumab, Darbepoetin Alfa, Darzalex (Daratumumab), Dasatinib, Daunorubicin Hydrochloride, Daunorubicin Hydrochloride and Cytarabine Liposome, Daurismo (Glasdegib Maleate), Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), Durvalumab, Duvelisib, Efudex (Fluorouracil—Topical), Eligard (Leuprolide Acetate), Elitek (Rasburicase), Ellence (Epirubicin Hydrochloride), Elotuzumab, Eloxatin (Oxaliplatin), Eltrombopag Olamine, Elzonris (Tagraxofusp-erzs), Emapalumab-lzsg, Emend (Aprepitant), Empliciti (Elotuzumab), Enasidenib Mesylate, Encorafenib, Enzalutamide, Epirubicin Hydrochloride, EPOCH, Epoetin Alfa, Epogen (Epoetin Alfa), Erbitux (Cetuximab), Eribulin Mesylate, Erivedge (Vismodegib), Erleada (Apalutamide), Erlotinib Hydrochloride, Erwinaze (Asparaginase *Erwinia chrysanthemi*), Ethyol (Amifostine), Etopophos (Etoposide Phosphate), Etopo side, Etopo side Phosphate, Evacet (Doxorubicin Hydrochloride Liposome), Everolimus, Evista (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Firmagon (Degarelix), Fludarabine Phosphate, Fluoroplex (Fluorouracil—Topical), Fluorouracil Injection, Fluorouracil—Topical, Flutamide, FOLFIRI, FOLFIRI-BEVACIZUMAB, FOLFIRI-CETUXIMAB, FOLFIRINOX, FOLFOX, Folotyn (Pralatrexate), Fostamatinib Disodium, FU-LV, Fulvestrant, Fusilev (Leucovorin Calcium), Gamifant (Emapalumab-lzsg), Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gilteritinib Fumarate, Glasdegib Maleate, Gleevec (Imatinib Mesylate), Gliadel Wafer (Carmustine Implant), Glucarpidase, Goserelin Acetate, Granisetron, Granisetron Hydrochloride, Granix (Filgrastim), Halaven (Eribulin Mesylate), Hemangeol (Propranolol Hydrochloride), Herceptin Hylecta (Trastuzumab and Hyaluronidase-oysk), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idarubicin Hydrochloride, Idelalisib, Idhifa (Enasidenib Mesylate), Ifex (Ifosfamide), Ifosfamide, IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iobenguane I 131, Ipilimumab, Iressa (Gefitinib), Irinotecan Hydrochloride, Irinotecan Hydrochloride Liposome, Istodax (Romidepsin), Ivosidenib, Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Larotrectinib Sulfate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Levulan Kerastik (Aminolevulinic Acid Hydrochloride), Libtayo (Cemiplimab-rwlc), LipoDox (Doxorubicin Hydrochloride Liposome), Lomustine, Lonsurf (Trifluridine and Tipiracil Hydrochloride), Lorbrena (Lorlatinib), Lorlatinib, Lumoxiti (Moxetumomab Pasudotox-tdfk), Lupron (Leuprolide Acetate), Lupron Depot (Leuprolide Acetate), Lutathera (Lutetium Lu 177-Dotatate), Lutetium (Lu 177-Dotatate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Mektovi (Binimetinib), Melphalan, Melphalan Hydrochloride, Mercaptopurine, Mesna, Mesnex (Mesna), Methotrexate, Methylnaltrexone Bromide, Midostaurin, Mitomycin C, Mitoxantrone Hydrochloride, Mogamulizumab-kpkc, Moxetumomab Pasudotox-tdfk, Mozobil (Plerixafor), Mustargen (Mechlorethamine Hydrochloride), MVAC, Myleran (Busulfan), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib To sylate Monohydrate, Nivolumab, Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Plerixafor, Pomalidomide, Pomalyst (Pomalidomide), Ponatinib Hydrochloride, Portrazza (Necitumumab), Poteligeo (Mogamulizumab-kpkc), Pralatrexate, Prednisone, Procarbazine Hydrochloride, Procrit (Epoetin Alfa), Proleukin (Aldesleukin), Prolia (Deno sumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, Ravulizumab-cwvz, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Retacrit (Epoetin Alfa), Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sancuso (Granisetron), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sustol (Granisetron), Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagraxofusp-erzs, Tagrisso (Osimertinib), Talazoparib To sylate, Talc, Talimogene Laherparepvec, Talzenna (Talazoparib Tosylate), Tamoxifen Citrate, Tarabine PFS (Cytarabine), Tarceva (Erlotinib Hydrochloride), Targretin (Bexarotene), Tasigna (Nilotinib), Tavalisse (Fostamatinib Disodium), Taxol (Paclitaxel), Taxotere (Docetaxel), Tecentriq (Atezolizumab), Temodar (Temozolomide), Temozolomide, Temsirolimus, Thalidomide, Thalomid (Thalidomide), Thioguanine, Thiotepa, Tibsovo (Ivosidenib), Tisagenlecleucel, Tocilizumab, Tolak (Fluorouracil—Topical), Topotecan Hydrochloride, Toremifene, Torisel (Temsirolimus), Totect (Dexrazoxane Hydrochloride), TPF, Trabectedin, Trametinib, Trastuzumab, Trastuzumab and Hyaluronidase-oysk, Treanda (Bendamustine Hydrochloride), Trexall (Methotrexate), Trifluridine and Tipiracil Hydrochloride, Trisenox (Arsenic Trioxide), Tykerb (Lapatinib Ditosylate), Ultomiris (Ravulizumab-cwvz), Unituxin (Dinutuximab), Uridine Triacetate, VAC, Valrubicin, Valstar (Valrubicin), Vandetanib, VAMP, Varubi (Rolapitant Hydrochloride), Vectibix (Panitumumab), VeIP, Velcade (Bortezomib), Vemurafenib, Venclexta (Venetoclax), Venetoclax, Verzenio (Abemaciclib), Vidaza (Azacitidine), Vinblastine Sulfate, Vincristine Sulfate, Vincristine Sulfate Liposome, Vinorelbine Tartrate, VIP, Vismodegib, Vistogard (Uridine Triacetate), Vitrakvi (Larotrectinib Sulfate), Vizimpro (Dacomitinib), Voraxaze (Glucarpidase), Vorinostat, Votrient (Pazopanib Hydrochloride), Vyxeos (Daunorubicin Hydrochloride and Cytarabine Liposome), Xalkori (Crizotinib), Xeloda (Capecitabine), XELIRI, XELOX, Xgeva (Denosumab), Xofigo (Radium 223 Dichloride), Xospata (Gilteritinib Fumarate), Xtandi (Enzalutamide), Yervoy (Ipilimumab), Yescarta (Axicabtagene Ciloleucel), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), Zytiga (Abiraterone Acetate), or any combination thereof.

Compositions can be administered with medical devices known in the art. For example, a pharmaceutical composition of the invention can be administered by injection with a hypodermic needle, including, e.g., a prefilled syringe or autoinjector.

The pharmaceutical compositions may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

The pharmaceutical compositions of the invention may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, chimeric, humanized and fully human antibodies are may be desirable.

Antibodies or antigen binding fragments thereof can be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 mg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144). Doses may also be provided to achieve a pre-determined target concentration of of the antibody in the subject's serum, such as 0.1, 0.3, 1, 3, 10, 30, 100, 300 µg/ml or more. In other embodiments, a fully human antibody is administered subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms "therapeutically effective amount", "therapeutically effective dose" and "effective amount" refer to an amount of the antibody, or antigen binding fragment thereof, that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the binding compound sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity. In some embodiments, an amount is a therapeutically effective amount if it is an amount that can be used to treat, ameliorate or diabetes, by, for example, modulating glucose transport, modulating GLUT4 internalization, modulating insulin resistance, and the like. In some embodiments, glucose transport or GLUT4 internalization is increased. In some embodiments, glucose transport or GLUT4 internalization is decreased. In some embodiments, insulin resistance is decreased. In some embodiments, insulin resistance is increased.

The term "subject" as used throughout includes any organism, such as an animal, including a mammal (e.g., rat, mouse, dog, cat, rabbit) and, for example, a human. A subject can be also be referred to as a patient. In some embodiments, the subject is a subject in need thereof. A subject that is "in need thereof" refers to a subject that has been identified as requiring treatment for the condition that is to be treated and is treated with the specific intent of treating such condition. The conditions can be, for example, any of the conditions described herein.

Whereas, an isolated antibody binds an epitope on a GLUT4 protein, or other protein described herein, and displays in vitro and/or in vivo GLUT4 inhibiting or therapeutic activities, the antibodies or antigen binding fragments thereof, capable of inhibiting GLUT4 function (e.g. internalization or glucose transport), are suitable both as therapeutic and prophylactic agents for treating or preventing GLUT4-associated conditions in humans and animals. These conditions include the glucose transport, obesity, insulin resistance, and diabetes. According, methods of treating such conditions are also provided, wherein the method comprises administering an antibody, or antigen binding fragment thereof, to the subject with such a condition.

In some embodiments, the methods comprise administering a therapeutically or prophylactically effective amount of one or more monoclonal antibodies or antigen binding fragments of the antibodies described herein to a susceptible subject or to one exhibiting a condition in which GLUT4 is known to have caused the pathology observed. Any active form of the antibody can be administered, including, but not limited to Fab and F(ab')2 fragments and other forms of antibodies provided for herein.

As used herein, a GLUT4 associated pathology refers to conditions that are caused by the function or aberrant function of a GLUT 4 receptor. These conditions include, but are not limited to, insulin resistance, glucose transport, diabetes, and the like.

In some embodiments, the antibodies used are compatible with the recipient species such that the immune response to the MAbs does not result in an unacceptably short circulating half-life or induce an immune response to the MAbs in the subject. In some embodiments, the MAbs administered exhibit some secondary functions such as binding to Fc receptors of the subject and activation of antibody dependent cell mediated cytotoxicity (ADCC) mechanisms.

Treatment of individuals may comprise the administration of a therapeutically effective amount of the antibodies described herein. The antibodies can be provided in a kit, such as those provided herein. The antibodies can be used or administered alone or in admixture with another therapeutic, analgesic, or diagnostic agent, such as provided for herein. In providing a patient with an antibody, or fragment thereof, capable of binding to GLUT4, or an antibody capable of protecting against GLUT4, pathology in a recipient patient, the dosage of administered agent will vary depending upon such factors as the patient's age, weight, height, sex, general medical condition, previous medical history, etc.

An antibody, capable treating a condition associated with GLUT4 activity or use to treat a GLUT4 related pathology, is intended to be provided to subjects in an amount sufficient to affect a reduction, resolution, or amelioration in the GLUT4 related symptom or pathology. Such a pathology includes, but is not limited to, glucose transport, insulin resistance, obesity, cancer, or diabetes in a subject. Examples of cancer, include, but are not limited to, brain cancers, lung cancer, colon cancer, prostate cancer, ovarian cancer, uterine cancer, endometrial cancer, skin cancer, breast cancer, throat cancer, esophageal cancer, bladder cancer, kidney cancer, gliomas, astrocytomas, and the like.

Accordingly, in some embodiments, methods of treating a subject with a GLUT4 mediated disorder are provided. In some embodiments, the method comprises administering a pharmaceutical composition comprising an antibody, or antigen binding fragment thereof, as provided herein. In some embodiments, the disorder is insulin resistance, obesity, diabetes or cancer. As provided for herein, the antibodies, or antigen binding fragments thereof, can be administered with other therapeutics. These can be administered simultaneously or sequentially.

In some embodiments, the antibodies, or antigen binding fragments thereof, may be used to treat diabetes, type 1 or type 2 diabetes. The antibodies, or antigen binding fragments thereof, may be used to, for example, normalize a patient's regimen and avoid blood sugar "dips" (e.g. hypoglycemia, e.g. blood sugar of below about 70 mg/dL) and "spikes" (e.g. hyperglycemia, e.g. blood sugar of below about 200 mg/dL) that afflict many patients with diabetes. Accordingly, in some embodiments, the antibodies, or antigen binding fragments thereof, may be used to treat or prevent symptoms associated with hypoglycemia, including for example, shakiness, anxiety, nervousness, palpitations, tachycardia, pallor, coldness, clamminess, dilated pupils (mydriasis), hunger, borborygmus, nausea, vomiting, abdominal discomfort, headache, abnormal mentation, impaired judgment, nonspecific dysphoria, paresthesia, negativism, irritability, belligerence, combativeness, rage, personality change, emotional lability, fatigue, weakness, apathy, lethargy, daydreaming, sleep, confusion, amnesia, lightheadedness or dizziness, delirium, staring, "glassy" look, blurred vision, double vision, flashes of light in the field of vision, automatism, difficulty speaking, slurred speech, ataxia, incoordination, focal or general motor deficit, paralysis, hemiparesis, paresthesia, headache, stupor, coma, abnormal breathing, generalized or focal seizures, memory loss, and amnesia.

In some embodiments, the antibodies, or antigen binding fragments thereof, may be used to treat or prevent symptoms associated with hyperglycemia, including for example, polyphagia, polydipsia, polyuria, blurred vision, fatigue, weight loss, poor wound healing, dry mouth, dry or itchy skin, tingling in feet or heels, erectile dysfunction, recurrent infections, external ear infections (e.g. swimmer's ear), cardiac arrhythmia, stupor, coma, and seizures. In various regimens, a type 1 diabetes subject may receive additional agents to supplement the therapies provided for herein.

Obesity refers to the medical condition in which adipose tissue (body fat) is systemically accumulated as a result of, for example, energy intake that is higher than energy expenditure over a long period of time. Obesity may result in various associated diseases, such as arteriosclerosis. In some embodiments, the antibodies, or antigen binding fragments thereof, can be used in methods for inducing weight loss or preventing weight gain, comprising administering an effective amount of the antibodies, or antigen binding fragments thereof, to a subject (patient) in need thereof. In some embodiments, wherein the subject does not substantially change caloric intake. In some embodiments, the caloric intake is high, relative to guidelines, such as the USDA tables. In some embodiments, the patient's caloric intake is 2000-10000 calories/day, or greater than about 2000 calories/day, or about 2200 calories/day, or about 2400 calories/day, or about 2600 calories/day, or about 2800 calories/day, or about 3000 calories/day, or about 3200 calories/day, or about 3400 calories/day, or about 3600 calories/day, or about 3800 calories/day, or about 4000 calories/day, or about 5000 calories/day, or about 6000 calories/day. In various embodiments, the patient has a high caloric intake and does not gain weight or even loses weight. Therefore, the present embodiments provide for an effect without life style changes that often reduce patient adherence (e.g. failed dieting). In some embodiments, the patient's caloric intake is not restricted by more than about 20%, or not by more than about 10%, or not by more than about 5% of the patient's caloric intake at the start of treatment. In some embodiments, a high proportion of the patient's caloric intake is "empty calories," i.e. calories from solid fats and/or added sugars. In some embodiments, greater than about 15%, or 20%, or 25%, or 30%, or 35%, or 50% of the patient's caloric intake is empty calories. Even in these embodiments, a patient may not gain weight or even lose weight.

In various embodiments, the subject (patient) is overweight or obese. In some embodiments, the patient suffers from central obesity. In some embodiments, the obesity of one of simple obesity (alimentary obesity; usually resulting from consumption of more calories than the body can utilize), secondary obesity (usually resulting from an underlying medical condition, such as, for example, Gushing's syndrome and polycystic ovary syndrome), and childhood obesity. In some embodiments, the obesity is classified as: Class I, which includes a BMI between 30 and 34.99; Class II, which includes BMIs of 35 to 39.99; and Class III, which mcludes a BMI of over 40. Further, the present invention provides for obesity of any of classes I, II, or III that is further classified as severe, morbid, and super obesity. In some embodiments, the patient is at risk of further weight gain, as assessed by, for example, daily caloric intake.

In some embodiments, the antibodies, or antigen binding fragments thereof, can be combined with other therapeutics as provided for herein. In some embodiments, the antibodies, or antigen binding fragments thereof, are administered with additional agents may be selected from among appetite suppressants, neurotransmitter reuptake inhibitors, dopaminergic agonists, serotonergic agonists, modulators of GABAergic signaling, anticonvulsants, antidepressants, monoamine oxidase inhibitors, substance P (NK1) receptor antagonists, melanocortin receptor agonists and antagonists, lipase inhibitors, inhibitors of fat absorption, regulators of energy intake or metabolism, cannabinoid receptor modulators, agents for treating addiction, agents for treating metabolic syndrome, peroxisome proliferator-activated receptor (PPAR) modulators; dipcptidyl peptidase 4 (DPP-4) antagonists, agents for treating cardiovascular disease, agents for treating elevated triglyceride levels, agents for treating low HDL, agents for treating hypercholesterolemia, and agents for treating hypertension. Some agents for cardiovascular disease include statins (e.g. lovastatin, atorvastatin, fluvastatin, rosuvastatin, simvastatin and pravastatin) and omega-3 agents (e.g. LOVAZA, EPANQVA, VASCEPA, esterified omega-3's in general, fish oils, hill oils, algal oils). In some embodiments, additional agents may be selected from among amphetamines, benzodiazepines, suifonyl ureas, meglitinides, thiazolidinediones, biguanides, beta-blockers, XCE inhibitors, diuretics, nitrates, calcium channel blockers, phenlermine, sibutramine, iorcaserin, cetilistat, rimonabant, taranabant, topiramate, gabapentin, valproate, vigabatrin, bupropion, tiagabine, sertraline, fluoxetine, trazodone, zonisamide, methylphenidate, varenicline, naltrexone, diethylpropion, phendimetrazine, rcpaglini.de, nateglinide, glimepiride, metformin, pioglitazone, rosiglilazone, and sitagliptin.

Kits are also provided which are useful for carrying out embodiments described herein. The present kits comprise a first container containing or packaged in association with the above-described antibodies. The kit may also comprise another container containing or packaged in association solutions necessary or convenient for carrying out the embodiments. The containers can be made of glass, plastic or foil and can be a vial, bottle, pouch, tube, bag, etc. The kit may also contain written information, such as procedures for carrying out the embodiments or analytical information, such as the amount of reagent contained in the first container means. The container may be in another container apparatus, e.g. a box or a bag, along with the written information.

Yet another aspect provided for herein is a kit for detecting GLUT4 protein in a biological sample. The kit includes a container holding one or more antibodies which binds an epitope of GLUT4 protein and instructions for using the antibody for the purpose of binding to GLUT4 protein to form an immunological complex and detecting the formation of the immunological complex such that the presence or absence of the immunological complex correlates with presence or absence of GLUT4 protein in the sample. Examples of containers include multiwell plates which allow simultaneous detection of GLUT4 protein in multiple samples.

In some embodiments, antibodies that bind to a GLUT4 protein are provided. In some embodiments, the antibody is isolated. In some embodiments, the antibody binds specifically. In some embodiments, the antibody binds to a GLUT4 protein that is properly folded. In some embodiments, the antibody is specific for a specific GLUT4 conformational state (open or closed). In some embodiments, the antibody binds to a GLUT4 protein in a cell membrane. In some embodiments, the antibody binds to a GLUT4 protein that is in a cell membrane in an intact cell. In some embodiments, the antibody inhibits or neutralizes the function of a GLUT4 protein. As used herein, the term "neutralize" means that the activity or function of the protein is inhibited. The inhibition can be complete or partial. In some embodiments, the activity or function of the protein is inhibited at least 10, 20, 30, 40, 50, 60, 70, 80, 90, 95, or 99%. The percent inhibition can be based upon the function or activity of the protein in the absence of the antibody. In some embodiments, the antibody inhibits the glucose transport facilitated by GLUT4. In some embodiments, the antibody inhibits the internalization of the GLUT4 protein.

In some embodiments, the antibody comprises a sequence as provided for herein or antigen binding fragment thereof. In some embodiments, the antibody comprises a heavy chain CDR or an antigen binding fragment thereof described herein. The heavy chain may be one or more of the heavy chains described herein. In some embodiments, the antibody comprises a light chain, or an antigen binding fragment thereof as described herein In some embodiments, methods of treating, inhibiting or ameliorating a GLUT4, associated pathology are provided. In some embodiments, the methods comprise administering an antibody described herein or a pharmaceutical composition described herein to a subject to treat, inhibit or ameliorate a GLUT4 associated pathology. In some embodiments, the pathology is glucose transport, insulin resistance, or diabetes.

In some embodiments, methods of detecting the presence or absence of a GLUT4 in a sample are provided, the method comprising contacting a sample with one or more antibodies described herein detecting the binding to a GLUT4 antigen by the antibody. In some embodiments, the detection of the binding indicates the presence GLUT4 antigen; or the absence of the detection of the binding to the GLUT4 antigen indicates the absence of the GLUT4 antigen. The detecting can be done with any known method, such as using a biosensor, ELISA, sandwich assay, and the like. However, in some embodiments, the method comprises detecting the presence of the protein in non-denaturing conditions. The non-denaturing conditions can be used so that the protein of interest is detected in its native, or properly folded form.

In some embodiments, methods of identifying a test antibody that binds to an epitope on GLUT4 protein, are provided, the method comprising contacting a test antibody with the epitope on GLUT4 protein and determining whether the test antibody binds to the epitope. In some embodiments, the determining comprises determining whether the test antibody binds to the protein and is competitively inhibited by an antibody comprising a sequence as provided herein. In some embodiments, the determining comprises mutating one or more residues of epitope or protein and determining binding of the test antibody to the mutated epitope, wherein if the mutation reduces binding of the test antibody as compared to the non-mutated epitope, the test antibody is deemed to bind to that epitope.

In some embodiments, methods of monitoring internalization of GLUT4 from the surface of a cell are provided. In some embodiments, the method comprising contacting the cell with an anti-GLUT4 antibody as provided herein and detecting the presence of GLUT4 in the cell or on the surface of the cell. The differences in cell surface expression can be measured and the internalization can be monitored and measured. This can be used, for example, to measure the effect of another molecule, such as a test agent, to modulate internalization of GLUT4 protein. Thus, the antibodies provided for herein can be used to identify test agents that modulate (increase or decrease) the internalization of GLUT4 protein. Test molecules that increase the internalization, which would be measured as a decrease in binding of an anti-GLUT4 antibody to GLUT4 protein on the cell surface, can be identified according to the methods provided herein. Test molecules that decrease the internalization, which would be measured as an increase in binding of an anti-GLUT4 antibody to GLUT4 protein on the cell surface, can be identified according to the methods provided herein. The surface expression can be measured by fluorescence, which can be done through a secondary antibody that recognized the GLUT4 antibodies or by labelling the anti-GLUT4 antibodies provided for herein.

In some embodiments, methods of inducing an immune response against a GLUT4 antigen are provided, the methods comprising administering a GLUT4 antigen to a subject under conditions sufficient to induce an immune response. In some embodiments, the GLUT4 antigen is delivered as a nucleic acid molecule encoding the GLUT4 antigen. As discussed herein, in some embodiments, the methods comprise administering a virus-like particle, such as a lipoparticle, comprising a GLUT4 antigen to the subject to induce the immune response. In some embodiments, antibodies produced by the immune response are isolated. The antibodies can then be cloned, isolated and/or otherwise modified as described herein.

In some embodiments, antibodies, or antigen binding fragments thereof, are further identified using a display library. In some embodiments, the antibodies that are generated through the use of VLPs that express GLUT4 protein are isolated and put into a library to further identify antibodies, or antigen binding fragments thereof. The libraries can be phage library or a yeast expression library. In some embodiments, the library is made from the immunized animal that generates antibodies against the GLUT4 VLPs. Thus, the antibodies, or antigen binding fragments thereof, can be identified by detecting the binding of a GLUT4 VLP with one of the protein members of the library.

In some embodiments, the library is a naïve library that is generated from a subject's antibodies. The library can also be a synthetic library that utilizes combintatorial biology to produce synthetic antibodies, or antigen binding fragments thereof, to produce antibodys, or antigen binding fragments thereof that bind to GLUT4 protein. The binding partners can be identified by screening, for example, the members of the library against VLPs that express GLUT4 protein. Any method can be used to detect the binding of the antibody, or antigen binding fragment thereof, with the VLP that expresses or contains GLUT4 on its surface.

In some embodiments, the subject is a chicken. In some embodiments, the GLUT4 antigen is a mutant protein as provided for herein. In some embodiments, the GLUT4 mutant protein is locked in conformational state. In some embodiments, the conformational state is outward-open or inward open. In some embodiments, the protein comprises a sequence of SEQ ID NO: 1, and a mutation at positions E345 or Y309. In some embodiments, the protein comprises a sequence of SEQ ID NO:1 with a E345Q and/or Y3091 mutation. In some embodiments, the protein comprises a E345A or Y309A mutation. In some embodiments, the subject is a human, a mouse, sheep, a rat, a rabbit, a shark, a llama, or a chicken.

In some embodiments, embodiments provided herein also include, but are not limited to:

1. A recombinant antibody that binds to a GLUT4 protein, wherein the GLUT4 protein is in its native conformation.
2. The antibody of embodiment 1, wherein the GLUT4 protein is human GLUT4 protein.
3. The antibody of embodiment 1, wherein the antibody is a monoclonal antibody.
4. The antibody of embodiment 1, wherein the antibody is a humanized antibody.
5. The antibody of embodiment 1, wherein the antibody is a chicken antibody.
6. The antibody of embodiment 1, wherein the antibody is a scFv antibody.
7. The antibody of any of embodiments 1-5, wherein the antibody comprises the sequence selected from one or more of the following sequences: SEQ ID NO: 2; SEQ ID NO: 3; SEQ ID NO: 4; SEQ ID NO: 5; SEQ ID NO: 6; or a variant thereof.
8. An antibody, or antigen binding fragment thereof, wherein the antibody or antibody fragment comprises:
   (i) a heavy chain variable region comprising heavy chain CDR1, CDR2, and CDR3 sequences, wherein the heavy chain CDR1 sequence has the amino acid sequence of 21, 27, 33, 39, 45, 51, 57, 63, 69, 75, 81, 87, 93, or 99; the heavy chain CDR2 has the amino acid sequence of 22, 28, 34, 40, 46, 52, 58, 64, 70, 76, 82, 88, 94, or 100; and the heavy chain CDR3 sequence has the amino acid sequence of SEQ ID NO: 23, 29, 35, 41, 47, 53, 59, 65, 71, 77, 83, 89, 95, or 101; or variants of any of the foregoing; and
   (ii) a light chain variable region comprising light chain CDR1, CDR2, and CDR3 sequences, wherein the light chain CDR1 sequence has the amino acid sequence 18, 24, 30, 36, 42, 48, 54, 60, 66, 72, 78, 84, 90, or 96; the light chain CDR2 sequence has the amino acid sequence of 19, 25, 31, 37, 43, 49, 55, 61, 67, 73, 79, 85, 91, or 97, and the light chain CDR3 sequence has the amino acid sequence of 20, 26, 32, 38, 44, 50, 56, 62, 68, 74, 80, 86, 92, or 98; or variants of any of the foregoing.
9. The antibody, or antigen binding fragment thereof, of embodiment 8, wherein the antibody comprises:
   (i) a heavy chain variable region comprising heavy chain CDR1, CDR2, and CDR3 sequences, wherein the heavy chain CDR1 sequence has the amino acid sequence of SEQ ID NO: 21, the heavy chain CDR2 has the amino acid sequence of SEQ ID NO: 22; and the heavy chain CDR3 sequence has the amino acid sequence of SEQ ID NO: 23; and (ii) a light chain variable region comprising light chain CDR1, CDR2, and CDR3 sequences, wherein the light chain CDR1 sequence has the amino acid sequence SEQ ID NO: 18; the light chain CDR2 sequence has the amino acid sequence of SEQ ID NO: 19, and the light chain CDR3 sequence has the amino acid sequence of SEQ ID NO: 20;

(i) a heavy chain variable region comprising heavy chain CDR1, CDR2, and CDR3 sequences, wherein the heavy chain CDR1 sequence has the amino acid sequence of SEQ ID NO: 27; the heavy chain CDR2 has the amino acid sequence of SEQ ID NO: 28; and the heavy chain CDR3 sequence has the amino acid sequence of SEQ ID NO: 29; or variants of any of the foregoing; and (ii) a light chain variable region comprising light chain CDR1, CDR2, and CDR3 sequences, wherein the light chain CDR1 sequence has the amino acid sequence SEQ ID NO: 24; the light chain CDR2 sequence has the amino acid sequence of SEQ ID NO: 25, and the light chain CDR3 sequence has the amino acid sequence of SEQ ID NO: 26; or variants of any of the foregoing;
   (i) a heavy chain variable region comprising heavy chain CDR1, CDR2, and CDR3 sequences, wherein the heavy chain CDR1 sequence has the amino acid sequence of SEQ ID NO: 33; the heavy chain CDR2 has the amino acid sequence of SEQ ID NO: 34; and the heavy chain CDR3 sequence has the amino acid sequence of SEQ ID NO: 35; or variants of any of the foregoing; and (ii) a light chain variable region comprising light chain CDR1, CDR2, and CDR3 sequences, wherein the light chain CDR1 sequence has the amino acid sequence SEQ ID NO: 30; the light chain CDR2 sequence has the amino acid sequence of SEQ ID NO: 31, and the light chain CDR3 sequence has the amino acid sequence of SEQ ID NO: 32; or variants of any of the foregoing;
   (i) a heavy chain variable region comprising heavy chain CDR1, CDR2, and CDR3 sequences, wherein the heavy chain CDR1 sequence has the amino acid sequence of SEQ ID NO: 39; the heavy chain CDR2 has the amino acid sequence of SEQ ID NO: 40; and the heavy chain CDR3 sequence has the amino acid sequence of SEQ ID NO: 41; or variants of any of the foregoing; and (ii) a light chain variable region comprising light chain CDR1, CDR2, and CDR3 sequences, wherein the light chain CDR1 sequence has the amino acid sequence SEQ ID NO: 36; the light chain CDR2 sequence has the amino acid sequence of SEQ ID NO: 37, and the light chain CDR3 sequence has the amino acid sequence of SEQ ID NO: 38; or variants of any of the foregoing;
   (i) a heavy chain variable region comprising heavy chain CDR1, CDR2, and CDR3 sequences, wherein the heavy chain CDR1 sequence has the amino acid sequence of SEQ ID NO: 45; the heavy chain CDR2 has the amino acid sequence of SEQ ID NO: 46; and the heavy chain CDR3 sequence has the amino acid sequence of SEQ ID NO: 47; or variants of any of the foregoing; and (ii) a light chain variable region comprising light chain CDR1, CDR2, and CDR3 sequences, wherein the light chain CDR1 sequence has the amino acid sequence SEQ ID NO: 42; the light chain CDR2 sequence has the amino acid sequence of SEQ ID NO: 43, and the light chain CDR3 sequence has the amino acid sequence of SEQ ID NO: 44; or variants of any of the foregoing;
   (i) a heavy chain variable region comprising heavy chain CDR1, CDR2, and CDR3 sequences, wherein the heavy chain CDR1 sequence has the amino acid sequence of SEQ ID NO: 51; the heavy chain CDR2 has the amino acid sequence of SEQ ID NO: 52; and the heavy chain CDR3 sequence has the amino acid sequence of SEQ ID NO: 53; or variants of any of the foregoing; and (ii) a light chain variable region comprising light chain CDR1, CDR2, and CDR3 sequences, wherein the light chain CDR1 sequence has the amino acid sequence SEQ ID NO: 48; the light chain CDR2 sequence has the amino acid sequence of SEQ ID NO: 49, and the light chain CDR3 sequence has the amino acid sequence of SEQ ID NO: 50; or variants of any of the foregoing;

(i) a heavy chain variable region comprising heavy chain CDR1, CDR2, and CDR3 sequences, wherein the heavy chain CDR1 sequence has the amino acid sequence of SEQ ID NO: 57; the heavy chain CDR2 has the amino acid sequence of SEQ ID NO: 58; and the heavy chain CDR3 sequence has the amino acid sequence of SEQ ID NO: 59; or variants of any of the foregoing; and (ii) a light chain variable region comprising light chain CDR1, CDR2, and CDR3 sequences, wherein the light chain CDR1 sequence has the amino acid sequence SEQ ID NO: 54; the light chain CDR2 sequence has the amino acid sequence of SEQ ID NO: 55, and the light chain CDR3 sequence has the amino acid sequence of SEQ ID NO: 56; or variants of any of the foregoing;

(i) a heavy chain variable region comprising heavy chain CDR1, CDR2, and CDR3 sequences, wherein the heavy chain CDR1 sequence has the amino acid sequence of SEQ ID NO: 63; the heavy chain CDR2 has the amino acid sequence of SEQ ID NO: 64; and the heavy chain CDR3 sequence has the amino acid sequence of SEQ ID NO: 65; or variants of any of the foregoing; and (ii) a light chain variable region comprising light chain CDR1, CDR2, and CDR3 sequences, wherein the light chain CDR1 sequence has the amino acid sequence SEQ ID NO: 60; the light chain CDR2 sequence has the amino acid sequence of SEQ ID NO: 61, and the light chain CDR3 sequence has the amino acid sequence of SEQ ID NO: 62; or variants of any of the foregoing;

(i) a heavy chain variable region comprising heavy chain CDR1, CDR2, and CDR3 sequences, wherein the heavy chain CDR1 sequence has the amino acid sequence of SEQ ID NO: 69; the heavy chain CDR2 has the amino acid sequence of SEQ ID NO: 70; and the heavy chain CDR3 sequence has the amino acid sequence of SEQ ID NO: 71; or variants of any of the foregoing; and (ii) a light chain variable region comprising light chain CDR1, CDR2, and CDR3 sequences, wherein the light chain CDR1 sequence has the amino acid sequence SEQ ID NO: 66; the light chain CDR2 sequence has the amino acid sequence of SEQ ID NO: 67, and the light chain CDR3 sequence has the amino acid sequence of SEQ ID NO: 68; or variants of any of the foregoing;

(i) a heavy chain variable region comprising heavy chain CDR1, CDR2, and CDR3 sequences, wherein the heavy chain CDR1 sequence has the amino acid sequence of SEQ ID NO: 75; the heavy chain CDR2 has the amino acid sequence of SEQ ID NO: 76; and the heavy chain CDR3 sequence has the amino acid sequence of SEQ ID NO: 77; or variants of any of the foregoing; and (ii) a light chain variable region comprising light chain CDR1, CDR2, and CDR3 sequences, wherein the light chain CDR1 sequence has the amino acid sequence SEQ ID NO: 72; the light chain CDR2 sequence has the amino acid sequence of SEQ ID NO: 73, and the light chain CDR3 sequence has the amino acid sequence of SEQ ID NO: 74; or variants of any of the foregoing;

(i) a heavy chain variable region comprising heavy chain CDR1, CDR2, and CDR3 sequences, wherein the heavy chain CDR1 sequence has the amino acid sequence SEQ ID NO: 81; the heavy chain CDR2 has the amino acid sequence of SEQ ID NO: 82; and the heavy chain CDR3 sequence has the amino acid sequence of SEQ ID NO: 83; or variants of any of the foregoing; and (ii) a light chain variable region comprising light chain CDR1, CDR2, and CDR3 sequences, wherein the light chain CDR1 sequence has the amino acid sequence SEQ ID NO: 78; the light chain CDR2 sequence has the amino acid sequence of SEQ ID NO: 79, and the light chain CDR3 sequence has the amino acid sequence of SEQ ID NO: 80; or variants of any of the foregoing;

(i) a heavy chain variable region comprising heavy chain CDR1, CDR2, and CDR3 sequences, wherein the heavy chain CDR1 sequence has the amino acid sequence of SEQ ID NO: 87; the heavy chain CDR2 has the amino acid sequence of SEQ ID NO: 88; and the heavy chain CDR3 sequence has the amino acid sequence of SEQ ID NO: 89; or variants of any of the foregoing; and (ii) a light chain variable region comprising light chain CDR1, CDR2, and CDR3 sequences, wherein the light chain CDR1 sequence has the amino acid sequence SEQ ID NO: 84; the light chain CDR2 sequence has the amino acid sequence of SEQ ID NO: 85, and the light chain CDR3 sequence has the amino acid sequence of SEQ ID NO: 86; or variants of any of the foregoing;

(i) a heavy chain variable region comprising heavy chain CDR1, CDR2, and CDR3 sequences, wherein the heavy chain CDR1 sequence has the amino acid sequence of SEQ ID NO: 93; the heavy chain CDR2 has the amino acid sequence of SEQ ID NO: 94; and the heavy chain CDR3 sequence has the amino acid sequence of SEQ ID NO: 95; or variants of any of the foregoing; and (ii) a light chain variable region comprising light chain CDR1, CDR2, and CDR3 sequences, wherein the light chain CDR1 sequence has the amino acid sequence SEQ ID NO: 90; the light chain CDR2 sequence has the amino acid sequence of SEQ ID NO: 91, and the light chain CDR3 sequence has the amino acid sequence of SEQ ID NO: 92; or variants of any of the foregoing; or (i) a heavy chain variable region comprising heavy chain CDR1, CDR2, and CDR3 sequences, wherein the heavy chain CDR1 sequence has the amino acid sequence of SEQ ID NO: 99; the heavy chain CDR2 has the amino acid sequence of SEQ ID NO: 100; and the heavy chain CDR3 sequence has the amino acid sequence of SEQ ID NO: 101; or variants of any of the foregoing; and (ii) a light chain variable region comprising light chain CDR1, CDR2, and CDR3 sequences, wherein the light chain CDR1 sequence has the amino acid sequence SEQ ID NO: 96; the light chain CDR2 sequence has the amino acid sequence of SEQ ID NO: 97, and the light chain CDR3 sequence has the amino acid sequence of SEQ ID NO: 98; or variants of any of the foregoing.

10. The antibody of embodiments 8 or 9 wherein the heavy chain variable region and the light chain variable region are not linked by a linker.

11. The antibody of embodiments 8 or 9, wherein the heavy chain variable region and the light chain variable region are linked with a peptide linker.
12. The antibody of embodiment 11, wherein the peptide linker comprises a sequence of GQSSRSSGGGGSSGGGGS (SEQ ID NO: 120); (GGGGS)$_n$ (SEQ ID NO: 121) (GGGGA)$_n$ (SEQ ID NO: 122), or any combination thereof, wherein each n is independently 1-5.
13. The antibody of embodiment 11, wherein the peptide linker does not comprise a sequence of GQSSRSSGGGGSSGGGGS (SEQ ID NO: 120).
14. The antibody of any one of embodiments 8-13, wherein the antibody comprises a sequence of SEQ ID NO.s: 8, 9, 10, 11, 12, 102, 104, 106, 108, 110, 112, 114, 116, or 118, or a variant thereof.
15. The antibody of any one of embodiments 8-13, wherein the antibody comprises a $V_L$ sequence of SEQ ID NO.s: 8, 9, 10, 11, 12, 102, 104, 106, 108, 110, 112, 114, 116, or 118, or a variant thereof.
16. The isolated antibody of any one of embodiments 8-15, wherein the antibody comprises a sequence of SEQ ID NOs: 13, 14, 15, 16, 17, 103, 105, 107, 109, 111, 113, 115, 117, or 119, or a variant thereof.
17. The antibody of any one of embodiments 8-15, wherein the antibody comprises a $V_H$ sequence of SEQ ID NOs: 13, 14, 15, 16, 17, 103, 105, 107, 109, 111, 113, 115, 117, or 119, or a variant thereof.
18. The antibody of any one of embodiments 8-18, wherein the antibody comprises a sequence of: SEQ ID NO: 8 and SEQ ID NO: 13, SEQ ID NO: 9 and SEQ ID NO: 14, SEQ ID NO: 10 and SEQ ID NO: 15, SEQ ID NO: 11 and SEQ ID NO: 16, or SEQ ID NO: 12 and SEQ ID NO: 17, SEQ ID NO: 102 and SEQ ID NO: 103, SEQ ID NO: 104 and SEQ ID NO: 105, SEQ ID NO: 106 and SEQ ID NO: 107, SEQ ID NO: 108 and SEQ ID NO: 109, SEQ ID NO: 110 and SEQ ID NO: 111, SEQ ID NO: 112 and SEQ ID NO: 113, SEQ ID NO: 114 and SEQ ID NO: 115, SEQ ID NO: 116 and SEQ ID NO: 117, SEQ ID NO: 118 and SEQ ID NO: 119, or any variants thereof.
19. The antibody of embodiment 18, further comprising a peptide linker sequence between the two sequences.
20. The antibody of embodiment 19, wherein the peptide linker comprises a sequence of GQSSRSSGGGGSSGGGGS; (GGGGS)$_n$; (GGGGA)$_n$, or any combination thereof, wherein each n is independently 1-5.
21. The antibody of any one of embodiments 8-20, wherein the variant has 1-10 substitutions, deletions, or insertions.
22. The antibody of embodiment 21, wherein the substitutions, deletions, or insertions is present in SEQ ID NOs: 8-21.
23. The antibody of any one of embodiments 8-20, wherein the variant has 1-10 conservative substitutions.
24. The antibody of embodiment 22, wherein the 1-10 conservative substitutions is present in SEQ ID NOs: 8-21.
25. The antibody of any one of embodiments 8-20, wherein the variant has at least 85% homology to a sequence of SEQ ID NOs: 8-21.
26. The antibody of any one of embodiments 8-20, wherein the variant has at least 90%, 91%, 92%, 93%, 94%, 95%, 96%, 97%, 98%, or 99% homology to a sequence of SEQ ID NOs: 8-21.
27. The antibody of any one of embodiments 8-20, wherein the variant has at least 85% identity to a sequence of SEQ ID NOs: 8-21.
28. The antibody of any one of embodiments 8-20, wherein the variant has at least 90%, 91%, 92%, 93%, 94%, 95%, 96%, 97%, 98%, or 99% identify to a sequence of SEQ ID NOs: 8-21.
29. The antibody of any one of embodiments 8-28, wherein the antibody is a scFv antibody.
30. The antibody of any one of embodiments 8-28, wherein the antibody is a monoclonal antibody.
31. The antibody of any one of embodiments 8-28, wherein the antibody is a humanized antibody.
32. A GLUT4 specific antibody that binds to residues R265 and G414 of GLUT4.
33. The antibody of embodiment 32, wherein the antibody comprises a heavy chain variable region CDR of CAK-STGYGDSWIYPDSIDA (SEQ ID NO: 29), or a variant thereof.
34. The antibody of embodiment 32, wherein the antibody comprises a sequence of SEQ ID NO: 9 or SEQ ID NO: 14, or a variant thereof.
35. The antibody of embodiment 32, wherein the antibody comprises a sequence of SEQ ID NO: 9 and SEQ ID NO: 14, or a variant thereof.
36. A GLUT4 specific antibody that binds to an inward-open GLUT4 protein in a native environment.
37. The antibody of embodiment 36, wherein the antibody comprises a heavy chain variable region CDR CAK-STGYGDSWIYPDSIDA (SEQ ID NO: 29), or a variant thereof.
38. The antibody of embodiments 36 or 37, wherein the antibody comprises a sequence of SEQ ID NO: 9 or SEQ ID NO: 14, or a variant thereof.
39. The antibody of embodiments 36 or 37, wherein the antibody comprises a sequence of SEQ ID NO: 9 and SEQ ID NO: 14, or a variant thereof.
40. The antibody of embodiments 38 and 39, wherein the peptides of SEQ ID NO: 9 and SEQ ID NO:14 are linked by a peptide linker.
41. The antibody of embodiment 40, wherein the peptide linker comprises a sequence of GQSSRSSGGGGSSGGGGS; (GGGGS)$_n$; (GGGGA)$_n$, or any combination thereof, wherein each n is independently 1-5.
42. The antibody of embodiment 41, wherein the antibody comprises a sequence of SEQ ID NO: 3, or a variant thereof.
43. An antibody that binds to an epitope of GLUT4 comprising residues E315 and G446.
44. The antibody of embodiment 43, wherein the antibody comprises a heavy chain variable region CDR of SEQ ID NO:20, or a variant thereof.
45. The antibody of embodiment 44, wherein the antibody comprises a sequence of SEQ ID NO: 10 or SEQ ID NO: 15, or a variant thereof.
46. The antibody of embodiment 44, wherein the antibody comprises a sequence of SEQ ID NO: 10 and SEQ ID NO: 15, or a variant thereof.
47. The antibody of embodiment 46, wherein the antibody further comprises a peptide linker sequence linking the peptide of SEQ ID NO: 10 and the peptide of SEQ ID NO: 15.

48. The antibody of embodiment 47, wherein the peptide linker comprises a sequence of GQSSRSSGGGGSSGGGGS; (GGGGS)$_n$; (GGGGA)$_n$, or any combination thereof, wherein each n is independently 1-5.
49. A antibody that specifically binds to an outward-open form of GLUT4 in a native environment.
50. The antibody of embodiment 49, wherein the antibody comprises a heavy chain variable region CDR of SEQ ID NO:20, or a variant thereof.
51. The antibody of embodiments 49 or 50, wherein the antibody comprises a sequence of: SEQ ID NO: 10 or SEQ ID NO: 15, or a variant thereof.
52. The antibody of embodiments 49 or 50, wherein the antibody comprises a sequence of: SEQ ID NO: 10 and SEQ ID NO: 15, or a variant thereof.
53. The antibody of embodiment 52, wherein the antibody further comprises a peptide linker sequence linking the peptide of SEQ ID NO: 10 and the peptide of SEQ ID NO: 15.
54. The antibody of embodiment 53, wherein the peptide linker comprises a sequence of GQSSRSSGGGGSSGGGGS; (GGGGS)$_n$; (GGGGA)$_n$, or any combination thereof, wherein each n is independently 1-5.
55. An antibody that binds to an epitope of GLUT4 comprising the residues of L61, G65, and P66.
56. The antibody of embodiment 55, wherein the antibody comprises a heavy chain variable region CDR of SEQ ID NO: 21, or a variant thereof.
57. The antibody of embodiments 55 or 56, wherein the antibody comprises a sequence of SEQ ID NO: 11 or SEQ ID NO: 16, or a variant thereof.
58. The antibody of embodiments 55 or 56, wherein the antibody comprises a sequence of SEQ ID NO: 11 and SEQ ID NO: 16, or a variant thereof.
59. The antibody of embodiment 58, wherein the antibody further comprises a peptide linker sequence linking the peptide of SEQ ID NO: 11 and the peptide of SEQ ID NO: 16.
60. The antibody of embodiment 59, wherein the peptide linker comprises a sequence of GQSSRSSGGGGSSGGGGS; (GGGGS)$_n$; (GGGGA)$_n$, or any combination thereof, wherein each n is independently 1-5.
61. An antibody that binds to an epitope of GLUT4 comprising the residue G65.
62. The antibody of embodiment 61, wherein the antibody comprises a CDR of SEQ ID NO: 21, or a variant thereof.
63. The antibody of embodiments 61 or 62, wherein the antibody comprises a sequence of SEQ ID NO: 12 or SEQ ID NO: 17, or a variant thereof
64. The antibody of embodiments 61 or 62, wherein the antibody comprises a sequence of SEQ ID NO: 12 and SEQ ID NO: 17, or a variant thereof.
65. The antibody of embodiment 64, wherein the antibody further comprises a peptide linker sequence linking the peptide of SEQ ID NO: 12 and the peptide of SEQ ID NO: 17.
66. The antibody of embodiment 65, wherein the peptide linker comprises a sequence of GQSSRSSGGGGSSGGGGS; (GGGGS)$_n$; (GGGGA)$_n$, or any combination thereof, wherein each n is independently 1-5.
67. A nucleic acid molecule encoding an antibody, or antigen binding fragment thereof, of any of the preceding embodiments.
68. A vector comprising the nucleic acid molecule of embodiment 67.
69. A cell comprising the nucleic comprising the nucleic acid molecule of embodiment 67 or the vector of embodiment 68.
70. A pharmaceutical composition comprising the antibody of any one of embodiments 1-66 or a nucleic acid molecule encoding the same.
71. The pharmaceutical composition of embodiment 70, wherein the composition is an injectable pharmaceutical composition.
72. The pharmaceutical compositions of embodiments 70 or 71, wherein the composition is sterile or pyrogen free.
73. The pharmaceutical compositions of any one of embodiments 70-72, wherein the composition is free of antibodies that do not bind to GLUT4.
74. A method of modulating GLUT4 internalization by contacting a cell expressing GLUT4 with a GLUT4 antibody or a pharmaceutical composition comprising the same that binds to GLUT4 on the cell surface, wherein the antibody is an antibody of any one of embodiments 1-66.
75. The method of embodiment 74, wherein the antibody reduces GLUT4 internalization.
76. A method of inhibiting the function of GLUT4 by contacting a cell expressing GLUT4 with an antibody of any one of embodiments 1-69, or a pharmaceutical composition comprising the same, to inhibit the function of GLUT4.
77. The method of embodiment 76, wherein the function is glucose transport.
78. A method of treating a subject with a GLUT4 mediated disorder, the method comprising administering a pharmaceutical composition comprising an antibody of any one of embodiments 1-66 to the subject.
79. The method of embodiment 78, wherein the disorder is insulin resistance, obesity, diabetes or cancer.
80. A method of monitoring internalization of GLUT4 from the surface of a cell, the method comprising contacting the cell with a GLUT4 antibody of any one of embodiments 1-66 and detecting the presence of GLUT4 in the cell or on the surface of the cell.
81. The method of embodiment 80, wherein the GLUT4 antibody binding is detected by fluorescence.
82. A method of identifying a test molecule that modulates the activity of GLUT4 function, the method comprising:
    contacting a cell with the test molecule;
    contacting the cell with a GLUT4 antibody of any one of embodiments 1-66 that binds to GLUT4 to quantify GLUT4 on the cell surface;
    wherein the test molecule that modulates the amount of GLUT4 on the cell surface as detected by the GLUT4 antibody that binds to GLUT4 is said to be a molecule that modulates GLUT4 function.
83. The method of embodiment 82, wherein the GLUT4 function is internalization.
84. The method of embodiment 83, wherein the GLUT4 internalization is enhanced or inhibited.
85. A method of detecting the presence or absence of GLUT4 in a sample comprising contacting a sample with an antibody of any one of embodiments 1-66 and detecting the binding to a GLUT4 antigen by the antibody,
wherein the detection of the binding indicates the presence GLUT4; or the absence of the detection of the binding to the GLUT4 indicates the absence of the GLUT4.

86. A method of inducing an immune response against GLUT4 protein in a subject, the method comprising administering a virus-like particle comprising the GLUT4 protein to the subject under conditions sufficient to induce an immune response.

87. The method of 86, wherein the subject is a human, a mouse, sheep, a rat, a rabbit, a shark, a llama, or a chicken.

88. A method of generating an antibody that binds to a GLUT4 protein, the method comprising administering a virus-like particle comprising the GLUT4 protein on its surface to a subject under conditions to induce an immune response against the GLUT 4 protein to generate the antibody that binds to the GLUT4 protein.

89. The method of embodiment 88, further comprising isolating the antibody that binds to the GLUT4 protein.

90. The method of embodiments 88 or 89, wherein the subject is a human, a mouse, sheep, a rat, or a chicken.

91. The method of any one of embodiments 88-90, wherein the antibody that is generated binds to GLUT 4 in a non-conformation dependent manner, inward-open GLUT4 protein, or outward-open GLUT4 protein.

92. The method of any one of embodiments 88-90, wherein the antibody that is generated binds to an extracellular domain of the GLUT4 protein.

93. The method of any one of embodiments 88-90, wherein the antibody that is generated binds to an intracellular domain of the GLUT4 protein.

94. The method of any one of embodiments 88-93, further comprising generating a virus-like particle comprising the GLUT4 protein, the method comprising transfecting or transducing a cell with GLUT4 protein and a retroviral gag protein under conditions sufficient to produce the virus-like particle comprising the GLUT4 protein.

95. The method of embodiment 94, wherein the cell is a HEK-293T cell.

96. The method of embodiment 94, wherein the gag protein is a MLV gag protein.

97. The method of embodiment 96, wherein the retroviral gag protein is Murine Leukemia Virus (MLV), gag, HIV gag, or RSV gag protein.

98. A GLUT4 mutant protein comprising any of the mutations provided herein.

99. The GLUT4 mutant proteins of embodiment 98, wherein the GLUT4 mutant protein is locked in conformational state.

100. The GLUT4 mutant protein of embodiment 98, wherein the protein comprises a sequence of SEQ ID NO: 1, and a mutation at one or more positions of M112, M158, Y159, E162, I163, R169, L247, R265, Q295, L296, Q298, N304, V306, F307, Y309, S310, I313, F314, E315, E345, G348, F405, R416, or G446 of SEQ ID NO:1.

The subject matter is now described with reference to the following examples. These examples are provided for the purpose of illustration only and the claims should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

EXAMPLES

Example 1: Generation, Characterization and Analysis of GLUT4 Antibodies and Epitopes Thereof Use of VLPs for immunization and phage display to isolate MAbs against native GLUT4

In order to generate conformationally-sensitive MAbs against GLUT4, we used murine leukemia virus (MLV)-based VLPs containing human GLUT4 ('Lipoparticles') for immunization. Without being bound by any particular theory, retaining the native structure of multispanning membrane proteins during immunization (and later phage panning steps) is vital for eliciting functionally relevant MAbs, which usually recognize conformational structures on the extracellular membrane protein face. VLPs are non-infectious lipid-enveloped retrovirus particles that can present intact multispanning membrane proteins on their surface with native topology and conformation (Hoffman T L, Canziani G, Jia L, Rucker J, & Doms R W (2000) A biosensor assay for studying ligand-membrane receptor interactions: Binding of antibodies and HIV-1 Env to chemokine receptors. Proc. Natl. Acad. Sci. USA 97(21): 11215-11220; 20; Endres M J, et al. (1997) Targeting of HIV- and SIV-infected cells by CD4-chemokine receptor pseudotypes. Science 278:1462-1464; Balliet J & Bates P (1998) Efficient infection mediated by viral receptors incorporated into retroviral particles. J. Virol. 72:671-676, each of which is hereby incorporated by reference in its entirety).

VLPs can capture high levels of structurally intact GPCRs, ion channels, and transporters when the virus particles bud from the plasma membrane, and are potent immunogens due to their particulate structure and multivalent epitope organization (Ludwig C & Wagner R (2007) Virus-like particles-universal molecular toolboxes. Curr Opin Biotechnol 18(6):537-545; Saitoh R, et al. (2007) Viral envelope protein gp64 transgenic mouse facilitates the generation of monoclonal antibodies against exogenous membrane proteins displayed on baculovirus. J Immunol Methods 322(1-2):104-117, each of which is hereby incorporated by reference in its entirety).

The level of incorporation of GLUT4 into the VLPs was ~300 pmol/mg (specific protein amount per mg total protein). For comparison, commercial membrane preparations generally contain 1 to 10 pmol/mg (e.g. from Perkin Elmer or Millipore-Sigma) and intact cells generally contain 0.1 to 1 pmol/mg, so the VLPs concentrated GLUT4 approximately 10-100 fold (Lai X (2013) Reproducible method to enrich membrane proteins with high purity and high yield for an LC-MS/MS approach in quantitative membrane proteomics. Electrophoresis 34(6):809-817; Bryk A H & Wisniewski J R (2017) Quantitative Analysis of Human Red Blood Cell Proteome. J Proteome Res 16(8):2752-2761, each of which is hereby incorporated by reference in its entirety).

The conservation of GLUT4 informed our choice of chickens as the host for immunization with human GLUT4 (hsGLUT4) VLPs. GLUT4 is highly conserved among mammals, with hsGLUT4 sharing 95-97% sequence identity with mouse, rat, and rabbit orthologs (Zhao F Q & Keating A F (2007) Functional properties and genomics of glucose transporters. Current genomics 8(2):113-128, which is hereby incorporated by reference in its entirety).

Generating antibodies against highly conserved proteins is difficult due to immune tolerance, which severely limits both the magnitude of the humoral response and the diversity of epitopes recognized. In contrast, birds have a large evolutionary distance from mammals so are capable of generating immune responses to human proteins that are highly conserved in mammals. Specifically, chickens lack a GLUT4 ortholog (Kono T, et al. (2005) Characterisation of glucose transporter (GLUT) gene expression in broiler chickens. British poultry science 46(4):510-515; Seki Y, Sato K, Kono T, Abe H, & Akiba Y (2003) Broiler chickens (Ross strain) lack insulin-responsive glucose transporter GLUT4 and have GLUT8 cDNA. General and comparative endocrinology 133(1):80-87, each of which is hereby incorporated by reference in its entirety) and their closest paralog is GLUT1, which is only 65% identical to hsGLUT4, making them an excellent host for antibody generation. Also, chicken immunoglobulin (IgY) is highly similar to mammalian IgG but with only a single VH and VL framework, making phage library creation and downstream humanization even easier than for murine antibodies (Finlay W J, Bloom L, Varghese S, Autin B, & Cunningham 0 (2017) Optimized Generation of High-Affinity, High-Specificity Single-Chain Fv Antibodies from Multi-Antigen Immunized Chickens. Methods Mol Biol 1485:319-338; Finlay W J, et al. (2017) Phage Display: A Powerful Technology for the Generation of High-Specificity Affinity Reagents from Alternative Immune Sources. Methods Mol Biol 1485:85-99, each of which is hereby incorporated by reference in its entirety).

Although the structure of GLUT4 has not been solved, the crystal structure of hsGLUT1 (65% identity) (Deng D, et al. (2014) Crystal structure of the human glucose transporter GLUT1. Nature 510(7503):121-125.), allows prediction of the position and size of the GLUT4 extracellular loops. GLUT4 has six predicted extracellular loops, all small (<12aa) except for loop 1 (32aa). A comparative alignment of the 80aa in the extracellular regions of hsGLUT4 showed 9aa differences with mouse (mm) GLUT4, but 29aa differences with chicken GLUT1. Extracellular loop 1 has only 4aa differences with mmGLUT4, but there are 11aa differences with chicken GLUT1, as well as a 4aa deletion, increasing the potential diversity of epitopes. From this analysis, the six extracellular loops of hsGLUT4 are predicted to comprise 32, 8, 12, 11, 8, and 9 amino acids, respectively (data not shown).

Based on this analysis, we selected chickens for immunization with hsGLUT4 VLPs to generate the most robust immune response against hsGLUT4. The sera of immunized chickens were screened by flow cytometry for reactivity with hsGLUT4 expressed in the avian cell line QT6 (FIG. 1, panel A). B cells from an animal with the most reactive serum were collected, and antibody $V_H$ and VL gene fragments were amplified by PCR and used to construct a diverse ($2\times10^9$) immunoglobulin single-chain variable fragment (scFv) library for phage display. The phage display library was panned in three consecutive rounds using hsGLUT4-VLPs (commercial 'Lipoparticles') (FIG. 1, panel B), resulting in 364 reactive phage clones. Screening of these clone by enzyme-linked immunosorbent assay (ELISA) identified 81 clones that bound to GLUT4 with a signal-to-background ratio of at least 5:1 (FIG. 1, panel C). DNA sequencing of these clones and alignment of the $V_H$ genes identified 29 unique clones falling into 6 unrelated sequence families. Based on their sequence diversity and initial binding properties, four clones (AB102, AB105, AB108, and AB111) were selected for further characterization and were subcloned into a human IgG1 Fc fragment vector for MAb production and characterization. A fifth clone (AB101) was used in selected experiments as a control; the other clones isolated were not further characterized. AB108 and AB111 were from the largest $V_H$ sequence family and contained identical $V_H$ sequences but different VL genes. Interestingly, for the 6 families of isolated MAbs, the lengths of H-CDR3s (the primary determinant of specificity for most MAbs) ranged from 16 to 26 amino acids (FIG. 1, panel D, and Table 2), reflecting the longer length of most chicken H-CDR3's compared to mouse or human (89% of chicken H-CDR3 sequences are between 15 and 23 residues) (Wu L, et al. (2012) Fundamental characteristics of the immunoglobulin $V_H$ repertoire of chickens in comparison with those of humans, mice, and camelids. J Immunol 188(1):322-333, which is hereby incorporated by reference in its entirety.)

Identification of MAbs that Bind Selectively to Human and Mouse GLUT4

Figure 2:
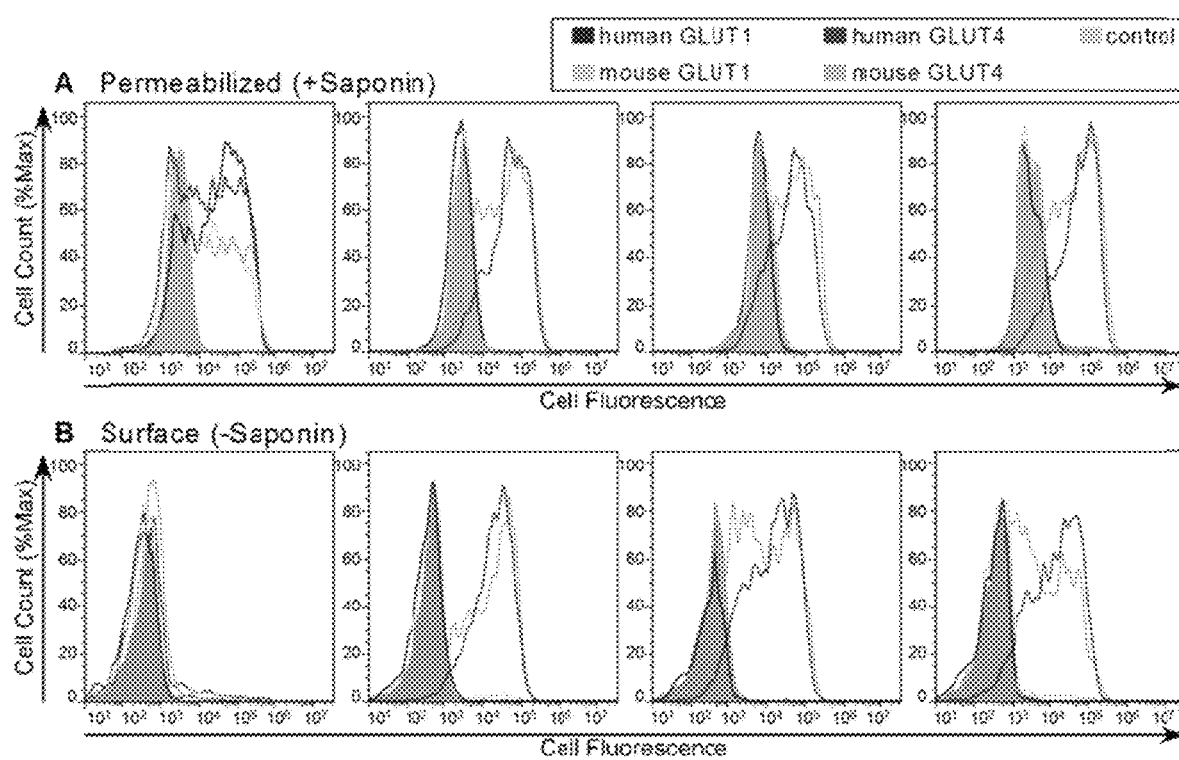
FIG. 2, panels A and B, illustrates reactivity of selected MAb clones against intracellular and surface GLUT4. Flow cytometry histograms for saponin-permeabilized (A) or surface stained (B) HEK-293T cells expressing hsGLUT4, mmGLUT4, hsGLUT1, mmGLUT1, or a negative control protein, stained with one of four MAbs (AB102, AB105, AB108, or AB111). All GLUT proteins tested here contained a C-terminal myc epitope tag that was used to verify expression.

To confirm the reactivity of the MAbs against native GLUT4 on human cells, we first assessed MAb binding by flow cytometry after permeabilizing HEK-293T cells transfected with GLUT4. All four MAbs demonstrated strong reactivity with GLUT4 (FIG. 2, PANEL A). All MAbs also demonstrated reactivity with mouse GLUT4 (mmGLUT4), which is important because murine cell lines such as 3T3-L1 adipocytes are routinely used to study GLUT4 trafficking. MAb AB105 reacted with endogenous GLUT4 on the surface of 3T3-L1 adipocytes in an insulin-dependent manner (data not shown), and MAbs AB102, AB105, and AB111 demonstrated various levels of reactivity with endogenous GLUT4 within permeabilized 3T3-L1 adipocytes (data not shown).

Reactivity was next assessed against surface-expressed hsGLUT4 and mmGLUT4. Three of the four tested MAbs (AB105, AB108, and AB111) were highly reactive against hsGLUT4 and mmGLUT4 on the cell surface (FIG. 2, PANEL B). The remaining MAb, AB102, exhibited minimal reactivity against hsGLUT4 or mmGLUT4 on the surface of non-permeabilized cells, but reacted strongly when cells were permeabilized using saponin, suggesting binding to an intracellular domain of GLUT4. To confirm that AB102 recognizes an intracellular epitope, transfected cells were labeled with propidium iodide (PI), a nuclear staining reagent that is not permeant to live cells, to differentiate naturally permeabilized (dead) and non-permeabilized (live) cell populations. PI staining confirmed that AB102 binding to GLUT4 occurs exclusively in the permeabilized cell population (data not shown). As positive controls, a commercial MAb (1F8) that binds an intracellular peptide on GLUT4 (Thoidis G, Kotliar N, & Pilch P F (1993) Immunological analysis of GLUT4-enriched vesicles. Identification of novel proteins regulated by insulin and diabetes. J Biol Chem 268(16):11691-11696, which is hereby incorporated by reference in its entirety.)

and another MAb that we isolated (AB101) that binds to a similar intracellular epitope, also bound exclusively to the naturally permeabilized (PI+) cell population. These results indicate that AB102 binds an intracellular epitope of GLUT4. While the use of VLPs biases antibody discovery towards extracellular epitopes, VLPs that break open clearly allow for the discovery of antibodies against intracellular epitopes as well.

We next tested the specificity of the MAbs against other GLUT family members. MAbs AB105, AB108, and AB111 demonstrated no cross-reactivity with hsGLUT1, hsGLUT2, hsGLUT3, or mmGLUT1 (FIG. 2 and data not shown), representing the GLUT family members with the highest homology to hsGLUT4. MAb AB102 was able to bind hsGLUT1 and mmGLUT1 (FIG. 2, PANEL A), which can be explained by a common epitope (discussed below). To further determine if these MAbs displayed cross-reactivity with any other human membrane proteins, the binding specificities of AB102, AB105, AB108, and AB111 were tested for reactivity against an array of 4,571 human membrane proteins expressed in cells (the Membrane Proteome Array, MPA), which includes GLUT1-13. Each antibody was added to the MPA and binding across the protein library was determined by flow cytometry. Three MAbs (AB105, AB108, and AB111) demonstrated very high specificity for GLUT4, with binding to GLUT4 10 to 100-fold above the other membrane proteins tested. AB102 bound to both GLUT4 and GLUT1, but did not bind well to any other membrane proteins (data not shown). Interestingly, the very low level reactivity of some MAbs with other membrane proteins can be explained by a common epitope.

MAbs Bind with pM to nM Affinities to Native GLUT4

Figure 3:
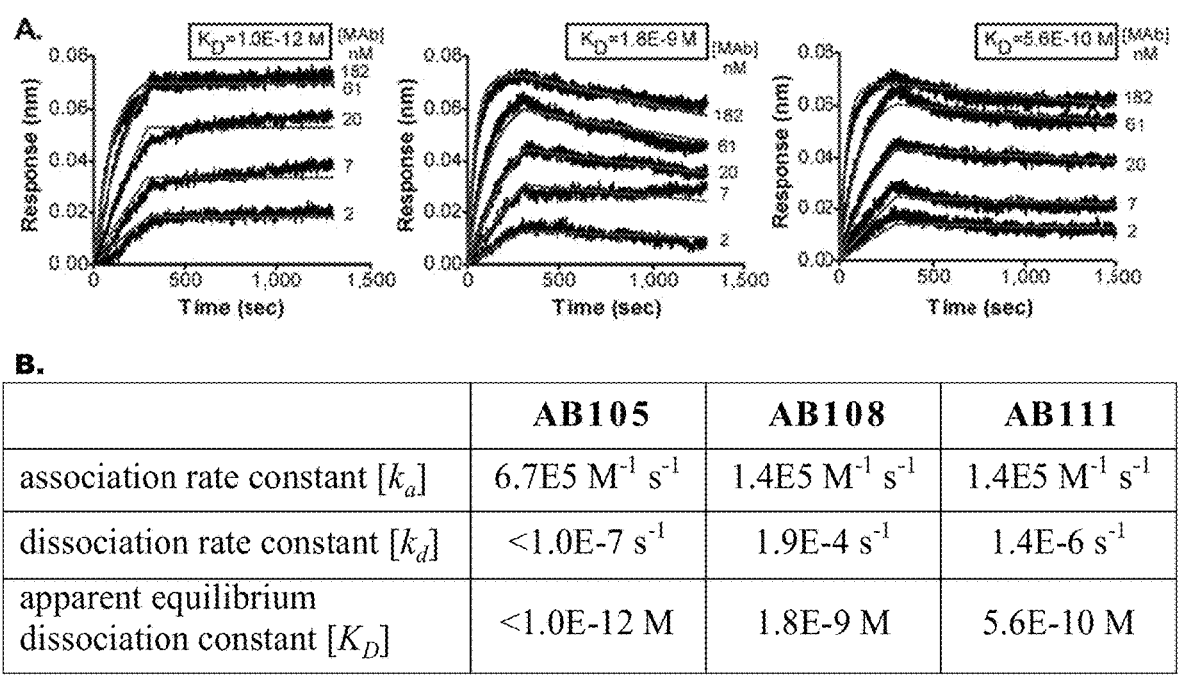
FIG. 3, panels A and B illustrates, in part, GLUT4 MAbs binding with pM to nM apparent affinity. Binding of AB105, AB108, and AB111 to native hsGLUT4 was detected using biotinylated VLPs immobilized on bio sensor tips. The kinetics of MAb binding to hsGLUT4 was assessed by fitting data to a 1:1 binding model to determine the rate constants. MAb titration experiments used bivalent scFv-Fc clones of each MAb, which results in apparent kinetics. Black curves represent the raw data curves of MAb binding and red curves are fitted traces. For AB105, the experiment was run out to 45 minutes without measurable dissociation.

To further characterize the binding activities of the selected GLUT4 MAbs, the kinetics of MAb binding to conformationally native GLUT4 were assessed using biosensor analysis. For this, biotinylated hsGLUT4-VLPs were immobilized onto biosensor tips, and the binding affinity and kinetics of MAbs AB105, AB108, and AB111 were measured using biolayer interferometry (FIG. 3, PANEL A). MAb titration experiments using bivalent scFv-Fc clones of each MAb (which results in apparent kinetics) demonstrated that AB105, AB108, and AB111 all have strong binding affinity to GLUT4, characterized by rapid association and slow dissociation (FIG. 3, PANEL B). Of the three MAbs, AB105 exhibited the strongest apparent binding affinity to GLUT4 of <1 pM, primarily due to its extremely slow dissociation rate. The binding kinetics of AB102 could not be measured since it binds an intracellular epitope and is therefore inaccessible in immobilized VLPs that contain an intact lipid bilayer.

GLUT4 MAbs AB102 and AB105 are Conformational and State-Dependent.

Since conformationally-intact GLUT4 was used for MAb isolation, we tested whether the resulting MAbs were reactive against conformational or linear epitopes of GLUT4. HEK-293T cells were transfected with a GLUT4-V5 construct and lysates were assayed by Western blotting with the four selected MAbs. None of the GLUT4 MAbs showed reactivity against denatured GLUT4 by Western blot. GLUT4-V5 expression was confirmed using an antibody against the V5 epitope tag included on its C-terminus. These results suggest that all four GLUT4 MAbs recognize conformational epitopes formed by the three-dimensional GLUT4 structure presented during VLP immunization.

Figure 4:
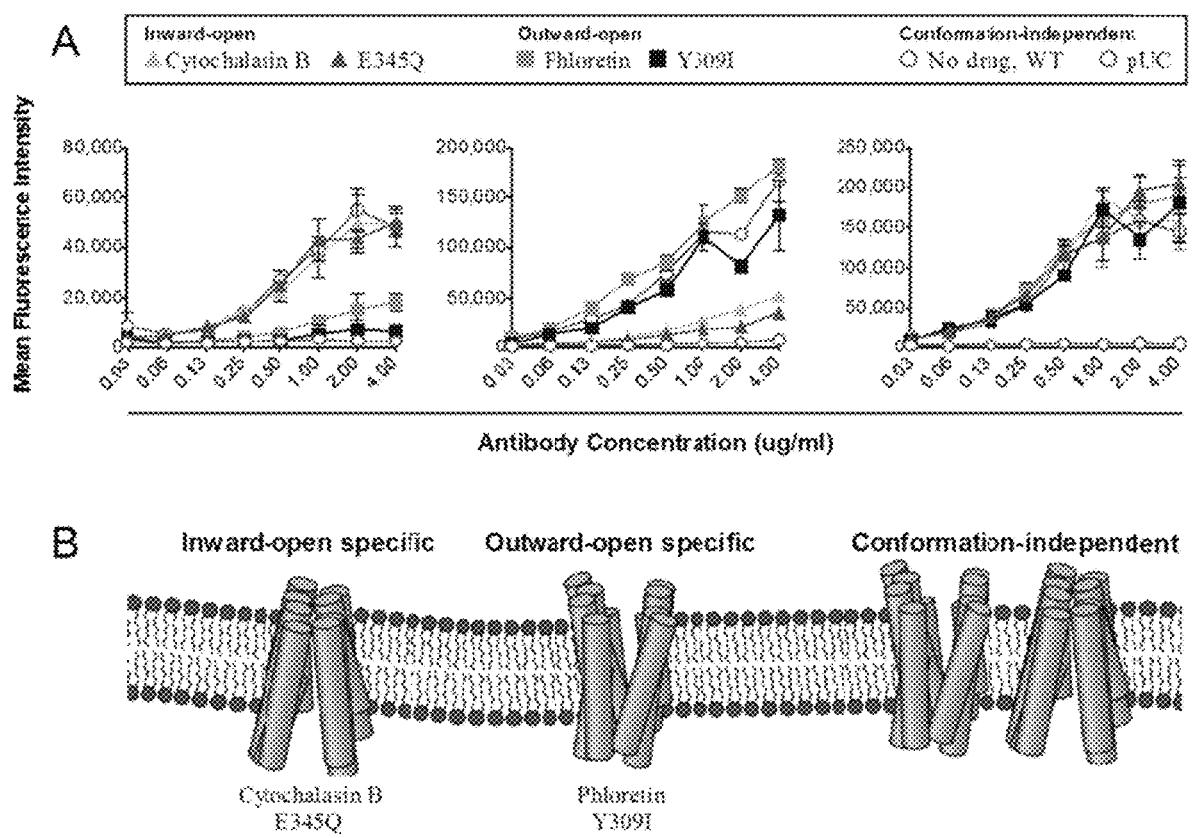
FIG. 4, panels A and B illustrate, for example, MAbs AB102 and AB105 showing state-specific binding to GLUT4. A. Wild type hsGLUT4 (WT) expressed on HEK-293T cells was treated either with cytochalasin B or phloretin, or mutated (E345Q or Y3091) to induce specific GLUT4 conformational states. The treated or mutated hsGLUT4 proteins were then assayed for binding by MAbs AB102, AB105, or AB111 followed by an Alexa Fluor 488-conjugated goat anti-human secondary antibody. Cells transfected with pUC vector were used as a negative control. MAb AB108 displayed similar reactivity as AB111 (not shown). B. The MAbs isolated are sensitive to GLUT4 conformations induced by the presence of cytochalasin B or E345Q (inward open), phloretin or Y3091 (outward open), or are conformation-independent.

Glucose transporters undergo large ligand-induced conformational changes during their transport cycle so can exist in several distinct states (Mohan S, Sheena A, Poulose N, & Anilkumar G (2010) Molecular dynamics simulation studies of GLUT4: substrate-free and substrate-induced dynamics and ATP-mediated glucose transport inhibition. PLoS One 5(12):e14217; Deng D, et al. (2014) Crystal structure of the human glucose transporter GLUT1. Nature 510(7503):121-125; Deng D, et al. (2015) Molecular basis of ligand recognition and transport by glucose transporters. Nature 526(7573):391-396; Quistgaard E M, Low C, Moberg P, Tresaugues L, & Nordlund P (2013) Structural basis for substrate transport in the GLUT-homology family of monosaccharide transporters. Nat Struct Mol Biol 20(6):766-768, each of which is hereby incorporated by reference in its entirety.) To test if binding of any of the isolated MAbs was state-dependent, we next assessed MAb binding to GLUT4 in distinct conformational states induced by either chemical compounds or point mutations. GLUT4 can be locked into an inward-open conformation by either the transport inhibitor cytochalasin B or an E345Q mutation (Schurmann A, et al. (1997) Role of conserved arginine and glutamate residues on the cytosolic surface of glucose transporters for transporter function. Biochemistry 36(42):12897-12902, which is hereby incorporated by reference in its entirety. Alternatively, GLUT4 can be locked into an outward-open conformation by the GLUT4 inhibitor phloretin or a Y309I mutation (Yano Y & May J M (1993) Ligand-induced conformational changes modify proteolytic cleavage of the adipocyte insulin-sensitive glucose transporter. Biochem J 295 (Pt 1):183-188; Mori H, et al. (1994) Substitution of tyrosine 293 of GLUT1 locks the transporter into an outward facing conformation. J Biol Chem 269(15):11578-11583, each of which is hereby incorporated by reference in its entirety). Unexpectedly, two of the four MAbs tested demonstrated state-specific binding. AB102 showed strong binding to GLUT4 in the inward-open conformation induced by both cytochalasin B and E345Q (FIG. 4). In contrast, locking GLUT4 into the outward-open conformation with phloretin or the Y309I mutation essentially abolished binding of AB102 to GLUT4. These results indicate that AB102 binding to GLUT4 is specific for the inward-open conformation of GLUT4.

MAb AB105 also demonstrated state-dependent binding to GLUT4, but in the opposite manner. AB105 showed strong binding to GLUT4 in the outward-open conformation induced by both phloretin and Y309I. In contrast, locking GLUT4 into the inward-open conformation with cytochalasin B or the E345Q mutation essentially abolished binding of AB105 to GLUT4, indicating that AB105 binding is dependent on the outward-open conformation of GLUT4.

Binding to GLUT4 by the other MAbs, AB108 and AB111, was unaffected by phloretin or cytochalasin B treatment, or by the two point mutations. Therefore, AB108 and AB111 appear to bind to a GLUT4 epitope whose availability is independent of the inward-open or outward-open states of GLUT4.

Figure 6:
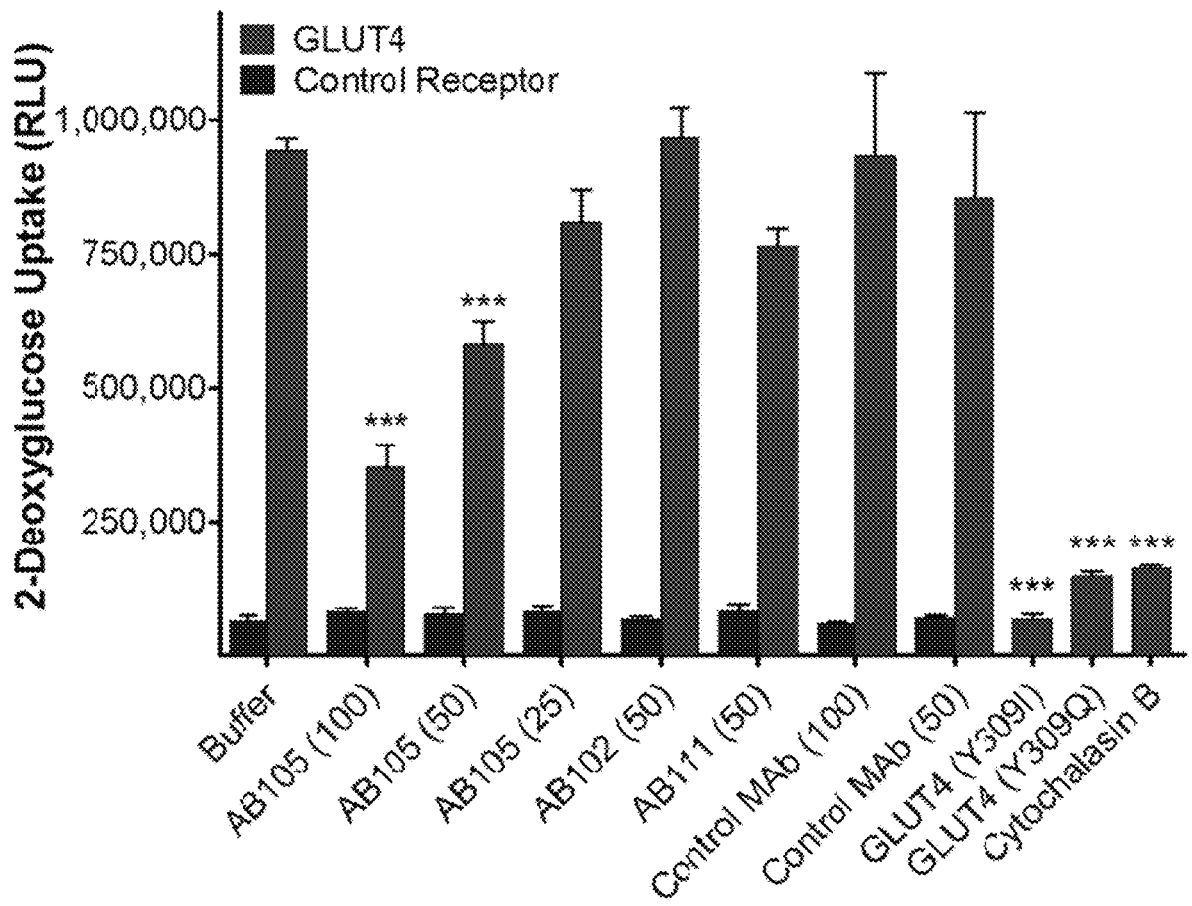
FIG. 6 illustrates, in some embodiments, state-specific GLUT4 antibodies, such as MAb AB105, inhibits glucose transport. GLUT4 was expressed in transfected HEK-293T cells and GLUT4 antibodies were tested for their ability to inhibit GLUT4 transport activity (Glucose Uptake-Glo™ kit, Promega). The state-specific MAb AB 105 at 50 and 100 ug/ml showed inhibition of glucose transport activity (***one-way ANOVA, p<0.001 compared to 50 ug/ml control MAb inhibition), while the intracellular antibody AB102, the state-independent antibody AB111, and a control antibody showed no inhibition of sugar uptake. The two conformational lock mutants (Y3091, E345Q) and the GLUT-specific inhibitor cytochalasin B (10 mM) were used as positive controls for transport inhibition. The specific GLUT1-inhibitor BAY-876 (10 nM) was included in all wells to inhibit basal glucose transport. A control receptor showed no glucose transport activity.

State-specific GLUT4 MAbs are expected to act as inhibitors of GLUT4-mediated glucose transport. We therefore tested the ability of antibodies to inhibit the ability of GLUT4 to transport a glucose analog using a bioluminescent assay. AB105 inhibited the ability of GLUT4 to transport 2-deoxyglucose, while neither AB111 (state-independent) or AB102 (intracellular) show inhibition at any concentration tested (FIG. 6).

Mapping of MAb Epitopes and Residues that Control GLUT4 State-Dependence

Because of the state-dependence of the isolated MAbs, we next wished to understand the mechanism by which each MAb could recognize GLUT4 in its different conformations. The residues required for binding of each MAb were determined using shotgun mutagenesis comprehensive alanine scanning (Davidson E & Doranz B J (2014) A High-Throughput Shotgun Mutagenesis Approach to Mapping B-cell Antibody Epitopes. Immunology, which is hereby incorporated by reference in its entirety). All residues of hsGLUT4 were individually mutated to alanine, with existing alanines changed to serines. Mutations were obtained for 508 of the 509 residues of GLUT4 (excluding the initiating methionine). The entire mutation library was transfected into human HEK-293T cells in a 384-well array format (one clone per well) and assessed for immunoreactivity using high-throughput flow cytometry.

MAb epitopes were obtained by testing each MAb against the entire mutation library, identifying residues whose mutation to alanine impaired binding relative to wild type GLUT4, which are illustrated in the Table 2.

TABLE 2

Residues critical for GLUT4 MAb binding. For each MAb, binding activities against mutations of the shown residue are expressed as the percentages of binding to wild type GLUT4, with ranges (half of the maximum - minimum values) in parentheses. All positions were individually changed to alanine unless otherwise indicated. For AB102, binding activities were measured in the presence of cytochalasin B (mapping in its absence produced inconclusive results). Values are indicated with an "*" or indicated with text "MAb epitopes", or with a "$" or indicated with text "(Outward-open locks)", or with a "#" or indicated with text "(Inward-open locks)", for critical epitope residues detected using each MAb below the designated threshold (20%). The reactivtiy values for other residues of significance (e.g. <30% reactivity) are also shown.

| | MAbs | | | | | |
|---|---|---|---|---|---|---|
| Residue | AB102 | AB105 | AB108 | AB111 | AB101 | 1F8 |
| L61 | 69 (15) | 101 (16) | 13 (3) MAb epitope* | 80 (4) | 115 (33) | 90 (9) |
| G65 | 95 (35) | 95 (8) | 1 (5) MAb epitope* | 15 (3) MAb epitope* | 87 (10) | 95 (6) |
| P66 | 97 (5) | 68 (5) | 11 (2) MAb epitope* | 90 (14) | 91 (10) | 78 (2) |
| M112 | 23 (9) | 30 (6) | 57 (17) | 79 (0) | 103 (28) | 120 (11) |
| L155 | 26 (3) | 22 (2) | 42 (10) | 57 (5) | 88 (37) | 91 (7) |
| M158 | 85 (9) | 17 (2) (Inward-open locks) # | 110 (4) | 107 (7) | 126 (12) | 95 (3) |
| Y159 | 11 (7) (Outward-open locks) $ | 38 (5) | 46 (20) | 88 (4) | 122 (9) | 96 (7) |
| E162 | 7 (3) (Outward-open locks) $ | 5 (1) (Inward-open locks) # | 41 (7) | 72 (4) | 83 (5) | 87 (2) |
| I163 | 28 (1) | 23 (0) | 90 (3) | 87 (3) | 115 (14) | 91 (12) |
| R169 | 77 (4) | 20 (3) (Inward-open locks) # | 108 (34) | 97 (13) | 119 (7) | 84 (8) |
| P224 | 29 (7) | 42 (5) | 56 (34) | 108 (0) | 90 (16) | 103 (7) |
| L247 | 15 (1) (Outward-open locks) $ | 23 (2) | 110 (46) | 99 (5) | 111 (12) | 95 (8) |
| L260 | 42 (5) | 31 (1) | 108 (21) | 130 (3) | 112 (7) | 98 (11) |
| R265 | -5 (4) MAb epitope* | 81 (1) | 111 (2) | 143 (8) | 91 (15) | 101 (2) |
| Q295 | 89 (2) | 4 (0) (Inward-open locks) # | 113 (4) | 138 (3) | 102 (8) | 81 (5) |
| L296 | 69 (3) | 27 (5) | 72 (6) | 144 (3) | 90 (10) | 105 (0) |
| Q298 | 107 (1) | 17 (1) (Inward-open locks) | 78 (5) | 145 (2) | 107 (0) | 87 (2) |
| N304 | 112 (9) | 11 (3) (Inward-open locks) # | 72 (6) | 125 (2) | 145 (6) | 79 (6) |
| V306 | 29 (5) | 98 (5) | 83 (6) | 171 (9) | 91 (9) | 74 (1) |
| F307 | 22 (2) | 117 (1) | 74 (11) | 108 (12) | 82 (4) | 84 (2) |
| Y309 | 24 (5) | 84 (10) | 91 (3) | 110 (9) | 64 (5) | 75 (1) |
| Y309I | 4 (2) (Outward-open locks) $ | 84 (10) | 67 (2) | 154 (19) | 110 (7) | 101 (10) |
| S310 | 20 (0) (Outward-open locks) $ | 125 (6) | 97 (10) | 130 (4) | 101 (3) | 93 (4) |
| I313 | 15 (2) (Outward-open locks) $ | 60 (2) | 39 (5) | 106 (8) | 94 (9) | 85 (9) |
| F314 | 23 (4) | 96 (9) | 92 (8) | 166 (7) | 91 (5) | 91 (7) |
| E315 | 76 (19) | 19 (2) MAb epitope* | 96 (17) | 164 (6) | 130 (11) | 93 (3) |
| E345 | 80 (17) | 5 (6) (Inward-open locks) # | 88 (82) | 200 (6) | 78 (12) | 93 (29) |
| E345Q | 39 (8) | 16 (2) (Inward-open locks) # | 78 (1) | 125 (3) | 96 (7) | 91 (3) |
| G348 | 79 (6) | 16 (2) (Inward-open locks) # | 94 (11) | 161 (7) | 101 (10) | 109 (12) |
| G356 | 72 (13) | 87 (0) | 19 (21) | 137 (21) | 46 (44) | 90 (3) |
| F405 | 105 (36) | 14 (5) (Inward-open locks) # | 103 (26) | 118 (13) | 106 (58) | 107 (5) |
| G414 | 23 (16) | 41 (11) | 80 (19) | 109 (5) | 83 (17) | 78 (1) |
| R416 | 70 (2) | 19 (5) (Inward-open locks) # | 67 (32) | 157 (9) | 69 (6) | 73 (5) |
| G446 | 43 (5) | 10 (3) MAb epitope* | 86 (13) | 71 (1) | 95 (29) | 108 (12) |
| Y502 | 94 (7) | 78 (3) | 94 (0) | 169 (1) | 4 (0) MAb epitope* | 51 (6) |
| G504 | 71 (17) | 96 (1) | 141 (3) | 172 (4) | 8 (2) MAb epitope* | 120 (13) |
| D506 | 60 (5) | 133 (22) | 105 (1) | 158 (3) | 34 (1) | 29 (8) |
| E507 | 97 (5) | 94 (1) | 53 (8) | 119 (2) | 5 (1) MAb epitope* | 127 (7) |
| N508 | 70 (6) | 74 (1) | 89 (1) | 193 (2) | 7 (2) MAb epitope* | 21 (15) |

Residues critical for each GLUT4 MAb epitope were identified as those where GLUT4 mutations resulted in less than 20% reactivity for the MAb of interest (relative to wild type GLUT4) yet greater than 70% wild type binding by a reference MAb. Residues were further validated as critical by comparing their reactivities across all MAbs tested to verify that the mutation did not globally disrupt the binding of diverse MAbs. The location and exposure of the identified residues was also taken into account as an indication of their potential for direct interaction with each MAb. Identified residues are 'hot-spots' that generally represent the most energetically important amino acids contributing to the binding of each MAb. As a control, epitope mapping of the commercial MAb 1F8 identified distal C-terminal amino acids D506 and N508 as its critical epitope residues, consistent with prior localization of the 1F8 epitope to a linear peptide from the distal C-terminus of GLUT4. Epitope mapping of our own MAb AB101 identified a binding site overlapping that of 1F8.

Mapping of MAb AB111 identified a single residue, G65, that, when mutated to alanine, eliminated AB111 binding. G65 is located at the apex of the largest GLUT4 extracellular loop (ECL1, 32aa), so binding of AB111 at this site is consistent with its location and exposure. Other GLUT4 residues likely also contact AB111 but do not sufficiently contribute to the energetics of the interaction for a single alanine substitution to disrupt binding.

For MAb AB108, which shares the same VH as AB111 but demonstrates a weaker affinity, G65 was also identified as a critical residue, along with adjacent residues L61 and P66. Mutation G356A also reduced the binding of AB108 to just below 20%, but its location in the middle of TM9 suggests that this mutation may have an allosteric effect on the AB108 epitope. Notably, although both AB108 and AB111 bind nearly sequential residues, neither recognizes denatured GLUT4 by Western blot, suggesting that the epitope structure recognized by these MAbs forms a three-dimensional conformation that requires the entire protein to be natively presented and is disrupted by protein unfolding.

MAb AB 105 binds to GLUT4 on the cell surface and binding is specific for GLUT4 in its outward-open conformational state. Screening of the GLUT4 mutation library identified thirteen critical residues with <20% binding of AB105. Residues E315, located on extracellular loop 4 (ECL4), and G446, on ECL6, were the only extracellular-accessible residues identified so likely form the critical binding amino acids for AB105. The locations of E315 and G446 explain the state-specific binding shown by AB105. Comparison between structures of GLUT proteins demonstrate that TM7 undergoes extensive local structural changes in the shift from outward-open to inward-open, which changes the relative positions of E315 and G446 at the GLUT4 extracellular surface and eliminates the conformational epitope formed by these residues.

Interestingly, additional residues critical for the binding of MAb AB 105 were also identified, but are located within the TM region and are not sufficiently exposed to allow MAb binding (data not shown). These residues, when individually mutated to alanine, abolish the binding of MAb AB105, which binds only the outward-open state of GLUT4. Remarkably, many of these residues have been implicated in controlling the conformational rearrangement of GLUT4 during glucose transport (Table 3), including residue E345, the site of the E345Q mutation that locks GLUT into the inward-open state (Schurmann A, et al. (1997) Role of conserved arginine and glutamate residues on the cytosolic surface of glucose transporters for transporter function. Biochemistry 36(42):12897-12902, which is hereby incorporated by reference in its entirety).

TABLE 3

Residues critical for GLUT4 state-specific MAb binding.

| Residue | AB102 | AB105 | Relation of Residue to State-Specificity |
|---------|-------|-------|------------------------------------------|
| M112 | 23 (9) | 30 (6) | May be involved in helical movements; mutation severely reduced transport (Heinze M, Monden I, & Keller K (2004) Cysteine-scanning mutagenesis of transmembrane segment 1 of glucose transporter GLUT1: extracellular accessibility of helix positions. Biochemistry 43(4):931-936; Mueckler M, Roach W, & Makepeace C (2004) Transmembrane segment 3 of the Glut1: glucose transporter is an outer helix. J Biol Chem 279(45):46876-46881.) |
| M158 | 85 (9) | 17 (2) [#] | |
| Y159 | 11 (7) (Outward-open locks) [$] | 38 (5) | Mutation severely reduced transport, predicted to be locked in one conformation (Mueckler M & Makepeace C (2005) Cysteine-scanning mutagenesis and substituted cysteine accessibility analysis of transmembrane segment 4 of the Glut 1 glucose transporter. J Biol Chem 280(47):39562-39568.) |
| E162 | 7 (3) (Outward-open locks) [$] | 5 (1) [#] | Conserved, essential for conformational rearrangement; mutation decreased cytochalasin binding, reduced transport |
| I163 | 28 (1) | 23 (0) | |
| R169 | 77 (4) | 20 (3) [#] | Conserved, interactions stabilize outward-open conformation; essential for conformational rearrangement, mutation decreased cytochalasin binding, reduced transport |
| L247 | 15 (1) (Outward-open locks) [$] | 23 (2) | |
| R265 | −5 (4) (MAb epitopes)[*] | 81 (1) | |
| Q295 | 89 (2) | 4 (0)[*] | Mutation severely decreased transport |
| L296 | 69 (3) | 27 (5) | Mutation decreased transport |
| Q298 | 107 (1) | 17 (1) [#] | Q298 binds cytochalasin; mutation decreased transport |
| N304 | 112 (9) | 11 (3) [#] | N304 binds cytochalasin; mutation severely decreased transport |
| V306 | 29 (5) | 98 (5) | TM 7b, changes conformation outward-open/occluded transition; mutation decreased transport |
| F307 | 22 (2) | 117 (1) | TM 7b, changes conformation outward-open/occluded transition; mutation decreased transport |
| Y309 | 4 (2) (Outward-open locks) [$] | 84 (10) | In TM 7b, changes conformation outward-open/occluded transition; mutation locks outward-open conformation (Mori et al., 1994; Deng et al., 2015) |
| S310 | 20 (0) (Outward-open locks) [$] | 125 (6) | TM 7b, changes conformation outward open/occluded transition; mutation eliminates cytochalasin binding, predicted to lock in outward-open conformation |
| I313 | 15 (2) (Outward-open locks)[$] | 60 (2) | TM 7b, changes conformation outward-open/occluded transition (Deng et al., 2015) |

TABLE 3-continued

Residues critical for GLUT4 state-specific MAb binding.

| Residue | AB102 | AB105 | Relation of Residue to State-Specificity |
|---|---|---|---|
| F314 | 23 (4) | 96 (9) | TM 7b, changes conformation outward-open/occluded transition (Deng et al., 2015) |
| E315 | 76 (19) | 19 (2) (MAb epitopes)* | |
| E345 | 80 (17) | 5 (6) (Inward-open locks) # | Conserved, mutation severely decreased transport, favors inward-open conformation |
| G348 | 79 (6) | 16 (2) (Inward-open locks)* | Conserved, component of intracellular gate (Deng et al., 2015) |
| F405 | 105 (36) | 14 (5) (Inward-open locks) | Mutation severely decreased transport |
| R416 | 70 (2) | 19 (5) (Inward-open locks) # | Conserved, stabilizes outward-open; mutation severely decreased transport, may lock as inward-open. |
| G446 | 43 (5) | 10 (3) (MAb epitopes)* | |

For each state-specific MAb, binding activities against each mutant are expressed as the percentages of binding to wild type GLUT4, with ranges (half of the maximum-minimum values) in parentheses. From crystallography of GLUT1, the equivalent GLUT4 residues that contact cytochalasin B are S96, S153, Q177, I180, Q298, N304, G400, W404, N427, and W428 (40), two of which were identified in our studies.
Values are indicated with a "*" or indicated with text "(MAb epitopes)", with a "$" or indicated with text "(Outward-open locks)", or with a "#" or indicated with text "(Inward-open locks)", for residues crtiical for the binding of each MAb.
The relation of each residue to state-specifity, based on prior research, is summarized.

This cluster also includes two residues (Q298 and N304) that are part of the binding site for cytochalasin B, which locks GLUT4 into the inward-open state and abolishes AB105 binding. Cumulatively, this data suggests that this group of residues in the TM region locks GLUT4 in an inward-open state.

MAb AB102 binds to GLUT4 only in permeabilized cells and binding is specific for GLUT4 in its inward-open conformational state. Screening of the GLUT4 mutation library identified seven critical residues with <20% binding by AB102. Residue R265, located on intracellular loop 3 (ICL3), was the only intracellular-accessible residue identified so is likely the critical binding contact for AB102. Residue G414, located on ICL5, was the only other poorly reactive amino acid located intracellularly so is likely also bound by AB102, but did not quite meet our threshold (23% reactivity with AB102). Interestingly, the locations of R265 and G414 may explain the state-specific binding shown by AB102. Comparison between structures of GLUT proteins demonstrate that ICL3 (proposed as a 'door closer' that determines the extent of inward opening) undergoes extensive local structural changes in the shift from outward-open to inward-open, which changes the relative positions of R265 (and G414) on the GLUT4 intracellular loops and eliminates the conformational epitope formed by these residues. These epitope residues also explain AB102's cross-reactivity with GLUT1, as both R265 and G414 are conserved within GLUT1 but at least one is changed in each of the other human GLUT family members.

Similar to the analysis of AB 105 binding, two additional clusters of residues critical for the binding of MAb AB102 were also identified, but are located within the TM region and are not sufficiently exposed to allow MAb binding (data not shown). These residues, when individually mutated to alanine, abolish the binding of MAb AB102, which binds only the inward-open state of GLUT4. Remarkably, many of these residues have been implicated in controlling the conformational rearrangement of GLUT4 during glucose transport (Table 3), including residue Y309, the site of the Y3091 mutation that locks GLUT into the outward-open state. The extracellular-most cluster (most of the residues from 306 to 314) forms the top of TM 7B that is also known to partly unwind and bend to form the outward-open state of GLUT4. Cumulatively, this data suggests that this group of residues in the TM region locks GLUT4 in an outward-open state.

Interestingly, mutation E162A was identified both as disrupting the inward-open state and the outward-open state (i.e. eliminating the ability of both AB102 and AB105 to bind). E162 is structurally located toward the cytoplasmic face of GLUT4 at the interface between the cluster of outward-open locking residues and inward-open locking residues. These data suggest that E162 may be centrally involved in the transition between the outward-open and inward-open conformational states of GLUT4.

Discussion

GLUT4, one of the most studied members of the GLUT family of glucose transporters, plays the central role in maintaining glucose homeostasis at cellular and physiological levels. Insulin induces GLUT4 translocation from intracellular storage vesicles to the cell surface where it drives post-prandial glucose uptake and maintenance of euglycemia. Disruption of GLUT4 regulation by insulin resistance results in the development of human diseases including diabetes and obesity. Monitoring the GLUT4 translocation process is useful not only for basic biochemical and cellular studies, but has also been used to screen for small-molecule insulin mimetics that can induce GLUT4 trafficking to the cell surface (Lanzerstorfer P, et al. (2014) Identification of novel insulin mimetic drugs by quantitative total internal reflection fluorescence (TIRF) microscopy. Br J Pharmacol 171(23):5237-5251, which is hereby incorporated by reference in its entirety).

, and could be a valuable diagnostic tool to screen patients for early stage insulin resistance before disease onset. However, to date, there are no tools available to help understand, detect, and visualize the native trafficking and conformational states of GLUT4—or most other transporters. The MAbs isolated in this study will therefore be valuable as tools to study human diseases that impact glucose homeostasis as well as for the development of assays to screen for small molecule drugs that modify GLUT4 transport.

Generating MAbs against the native extracellular epitopes of multispanning membrane proteins is challenging due to multiple issues, including the difficulty in maintaining the membrane-dependent structure during immunization and panning/screening, poor immunogenicity of small extracellular loops, and immune tolerance due to high sequence identity among mammals that limits the antibody response. As a result, there have been no MAbs that recognize the conformational structure of GLUT4, and, more generally, few MAbs against native epitopes for any multispanning membrane proteins, including most GPCRs, ion channels, and transporters (42. Douthwaite J A, Finch D K, Mustelin T, & Wilkinson T C (2017) Development of therapeutic antibodies to G protein-coupled receptors and ion channels: Opportunities, challenges and their therapeutic potential in respiratory diseases. Pharmacol Ther 169:113-123). Here, we have isolated conformationally sensitive MAbs against one of the most challenging multispanning membrane proteins, GLUT4, containing twelve transmembrane domains and six small highly conserved extracellular loops.

The biological characteristics of retroviral VLPs were critical both for immunization and for MAb isolation by phage panning. Multispanning membrane proteins such as GLUT4 require the continued presence of a lipid membrane to maintain native extracellular epitopes. Retroviral VLPs are produced by budding from the plasma membrane, so GLUT4 was maintained in its native cellular membrane at all stages of production and purification, eliminating the need to extract protein from the membrane with the attendant risk of denaturation and misfolding. Membrane proteins are also often difficult to express at high levels due to poor translation, folding, and trafficking. We were able to incorporate high levels of GLUT4 in VLPs (~300 pmol/mg), approximately 10 to 100 fold more concentrated than in cells or traditional membrane preparations, contributing to the success of both immunization and phage panning. Immunogenicity was likely further improved by the size (~150 nm) and particulate nature of VLPs, which are efficiently targeted by dendritic cells for antigen processing and presentation. Although we were primarily interested in generating MAbs against extracellular epitopes, we also identified MAbs against intracellular regions. Intracellular epitopes are likely exposed when the VLP immunogen is broken open during immunization, antigen presentation, and phage panning, although the conformation-dependent nature of the isolated MAbs suggests that GLUT4 within VLPs still maintained its native structure throughout these manipulations. Based on the state-dependent MAbs isolated, VLPs are also able to present integral membrane proteins in multiple, biologically relevant states.

To avoid problems associated with immune tolerance, chickens were chosen as the immunization host species, since the most similar GLUT homolog in chickens is only 65% identical to hsGLUT4, compared to 95% identical to mmGLUT4. In many respects, chickens are very similar to and perhaps even better than mammalian hosts in terms of antibody generation and isolation, and produce immunoglobulin (IgY) that is highly similar to mammalian IgG. Chicken antibodies have a single VH and VL framework, which simplifies the molecular biology of phage library construction, minimizes VH/VL incompatibility when building a large scFv library, and makes humanization of any desired antibodies much easier than murine humanization (Finlay W J, Bloom L, Varghese S, Autin B, & Cunningham 0 (2017) Optimized Generation of High-Affinity, High-Specificity Single-Chain Fv Antibodies from Multi-Antigen Immunized Chickens. Methods Mol Biol 1485:319-338; Finlay W J, et al. (2017) Phage Display: A Powerful Technology for the Generation of High-Specificity Affinity Reagents from Alternative Immune Sources. Methods Mol Biol 1485:85-99, each of which is hereby incorporated by reference in its entirety).

The anti-GLUT4 scFv phage display library created here was constructed using VH and VL genes derived from B cells from a single sero-positive chicken. After panning on hsGLUT4 VLPs, 29 unique clones were identified representing 6 unrelated VH-CDR3 sequence families. Given the relatively modest extent of our screen, it is likely that further screening of additional phage clones and under different conditions would identify additional unique GLUT4 antibodies. For example, similar campaigns we have since conducted against other multispanning membrane proteins have identified hundreds of unique family members after more extensive screening. Future discovery campaigns could also utilize conformationally-locked GLUT4 to bias recovery of MAbs with desired binding properties. AB108 and AB111 have distinct VL genes, but identical VH genes, overlapping epitopes, and similar apparent affinities, reflecting the dominance of VH in MAb binding. Chicken VH genes appear to have an especially dominant role in antigen interaction since they have relatively long VH CDR3's (Finlay W J, Bloom L, Varghese S, Autin B, & Cunningham 0 (2017) Optimized Generation of High-Affinity, High-Specificity Single-Chain Fv Antibodies from Multi-Antigen Immunized Chickens. Methods Mol Biol 1485:319-338; Wu L, et al. (2012) Fundamental characteristics of the immunoglobulin VH repertoire of chickens in comparison with those of humans, mice, and camelids. J Immunol 188(1): 322-333; Konitzer J D, et al. (2017) Generation of a highly diverse panel of antagonistic chicken monoclonal antibodies against the GIP receptor. MAbs 9(3):536-549, each of which is hereby incorporated by reference in its entirety). Long VH CDR3's may also be especially useful for binding to multispanning membrane proteins that often have functionally important binding pockets that long CDRs may reach into.

To develop a detailed understanding of how the MAbs bind, AB102, AB105, AB108, and AB111 were characterized for affinity, specificity, and the nature of the epitopes that they recognize (summarized in FIG. 5). Given the 95% identity between human and mouse GLUT4, it was not surprising that all of the MAbs were able to recognize both proteins. However, generating mouse antibodies able to cross-react across human and mouse orthologs is often difficult using traditional immunization host species because of immune tolerance mechanisms. Using chickens as the host animal enabled us to easily isolate human-mouse cross-reactive antibodies. While hsGLUT1, the closest paralog to hsGLUT4, is only 65% identical, one MAb, AB102, was also able to cross-react with hsGLUT1, explained by the identified AB102 epitope residues being conserved between hsGLUT1 and hsGLUT4.

Additional information about some antibodies can also be found in Tucker et al. PNAS May 29, 2018 115 (22) E4990-E4999, which is hereby incorporated by reference in its entirety.

Unexpectedly, out of four MAbs characterized, we identified two state-specific MAbs, AB102 and AB105, with specificity for opposing inward-open and outward-open conformations of GLUT4. Locking GLUT4 into defined inward- or outward-open conformations, using either pharmacological agents or mutations, enabled or eliminated MAb binding. Additionally, binding of AB105 was able to inhibit the transport function of GLUT4, consistent with its ability to bind GLUT4 extracellularly and in a state-specific fashion. Consistent with their state specificity, the epitopes of AB102 and AB 105 each spanned two loops of GLUT4 that demonstrate relative structural rearrangement between the two states, whereas the epitopes for the conformationally insensitive MAbs AB108 and AB111 were contained in a single loop. To the best of our knowledge, AB102 and AB105 are the only state-specific MAbs ever isolated against a glucose transporter and some of the only state-specific MAbs against any transporter. One other antibody was recently reported that inhibits the eukaryotic transporter ABCG2 from entering its inward facing conformation. MAbs specific for the conformational states of other complex membrane proteins, such as eukaryotic GPCRs and ion channels as well as the lactose permease prokaryotic transporter, have proven critical for understanding the structure and function of these proteins. We expect that the availability of state-specific MAbs against GLUT4 will be helpful in detecting transient conformational changes of GLUT4 during glucose transport, as well as for future structural studies of GLUT4 stabilized in state-specific conformations. These MAbs may also be useful as tools for identifying small molecules that preferentially bind specific states of GLUT4. Finally, the ability of MAbs to functionally modulate transporter function (e.g. as antagonists or agonists) opens up potential new avenues of therapeutic intervention for diseases such as diabetes and cancer.

The epitopes of the GLUT4 MAbs were determined using comprehensive alanine scanning shotgun mutagenesis. Two MAbs, AB108 and AB111, bound the apex of ECL1, the largest extracellular loop at 32aa and the most accessible extracellular site on GLUT4. AB105 bound across ECL4 and ECL6, which are each only ~10 residues long and are recessed in a cavity on the surface of GLUT4. Interestingly, AB105 contains the longest VH CDR3 (26 residues) among the isolated MAbs, which may enable it to bind in the cavity formed by ECL4 and ECL6 and sense the outward-open state of GLUT4. It is notable that a MAb with this length of CDR3 would not likely be found using traditional immunization hosts, but chicken CDR3s are generally longer than either mouse or human CDR3s, so make such MAbs more likely (FIG. 2D). We note that the epitope data for AB105 (and AB102) do not enable us to distinguish between states of GLUT4 with or without bound ligand and we have not seen differences in binding in the presence or absence of glucose. Studies using non-transportable sugars such as maltose may enable determination of the exact conformational state bound by these antibodies.

Since binding of the state-dependent MAbs AB102 and AB105 was tested against alanine mutations across the entire GLUT4 sequence, we were also able to comprehensively identify mutations that lock GLUT4 into inward-open or outward-open conformations. Remarkably, the sites of these mutations were clustered around many positions known to influence the conformational state of GLUT4, including previously defined locking mutants and the binding site for cytochalasin. Still, it is possible that these residues could be affecting GLUT4 and MAb binding in alternative ways, such as allosterically affecting the MAb binding sites.

Interestingly, mutation of residue E162 eliminated both AB102 and AB105 reactivity (although not AB108 or AB111 reactivity, GLUT4 surface trafficking, or GLUT4 expression). E162 is located at the interface between the outward-open and inward-open locking residue clusters that we identified (data not shown), and was previously identified as essential for conformational rearrangement. Its location, effect on GLUT4 function, and effect on GLUT4 conformation (stabilizing a conformation of GLUT4 that is neither inward-open nor outward-open) suggests that residue E162 plays a critical role in the transition between the inward-open and outward-open conformations.

The results of this study highlight the utility of VLPs and divergent host animals for the isolation of conformational MAbs against complex multispanning membrane proteins. MAbs specific for extracellular epitopes, intracellular epitopes, and the two conformational states of GLUT4 were readily isolated using the strategies outlined here. These MAbs represent the first reagents of their kind and can be used for monitoring native GLUT4 function and trafficking, studying the structure of GLUT4, differentiating different GLUT4 epitopes and states, and high-throughput screening of novel diabetes therapeutics.

Materials and Methods

Isolation of GLUT4 MAbs

VLPs displaying GLUT proteins (commercially referred to as 'Lipoparticles') were produced by cotransfection of HEK-293T cells with plasmids carrying hsGLUT1 or hsGLUT4 genes and the retroviral (MLV) Gag protein, as previously described (Hoffman T L, Canziani G, Jia L, Rucker J, & Doms R W (2000) A biosensor assay for studying ligand-membrane receptor interactions: Binding of antibodies and HIV-1 Env to chemokine receptors. Proc. Natl. Acad. Sci. USA 97(21):11215-11220; Willis S, et al. (2008) Virus-like particles as quantitative probes of membrane protein interactions. Biochemistry 47(27):6988-6990, each of which is hereby incorporated by reference in its entirety. 'Null' VLPs were produced the same way but without transfection of a specific receptor.

A scFv phage display library was constructed from B cells of a hsGLUT4 VLP-immunized chicken that showed serum reactivity with GLUT4 by flow cytometry, as previously described (Finlay W J, Bloom L, Varghese S, Autin B, & Cunningham O (2017) Optimized Generation of High-Affinity, High-Specificity Single-Chain Fv Antibodies from Multi-Antigen Immunized Chickens. Methods Mol Biol 1485:319-338, which is hereby incorporated by reference in its entirety.) For panning, the phage library (2E9) was allowed to bind to wells coated with GLUT4 VLPs (for positive selection) or null VLPs (for de-selection). Bound phage was trypsin-eluted and amplified through three rounds of panning before screening the clones for binding to GLUT4. Individual scFv peripreps were prepared from single colonies by induction with 1 mM IPTG (iso-propyl-β-D-thiogalactopyranoside) at 28° C. overnight followed by extraction of the periplasmic fraction by freeze-thaw, and then screened for hsGLUT4-specific binding by ELISA using VLPs.

For screening phage clones by periprep ELISA, purified hsGLUT4-displaying VLPs were coated on a 96-well white, flat-bottom microtiter plate overnight at 4° C. using 0.25 µg of protein per well in 0.1 M sodium bicarbonate buffer, pH 8.6. The wells were washed with PBS and blocked with 4% PBS–/– with 4% milk (PBSM) for 1 h. scFv in 4% PBSM were added to each well, and the plate was incubated for 1 h at 37° C. with gentle agitation. The scFv solution was discarded, and the plate was washed 3 times with PBS plus 0.01% Tween 20. To detect bound scFv, a 1:5,000 dilution of anti-human Fd conjugated with horseradish peroxidase (HRP; Southern Biotech, Birmingham, Ala.) in 4% PBSM was added to the wells, and the plate was incubated at room temperature (22° C.) for 30 min with gentle agitation. The plate was washed 3 times with PBS plus 0.01% Tween 20 and developed according to the manufacturer's instructions (Super Signal West Pico; Thermo Scientific, Waltham, Mass.). Negative controls included a buffer blank (no antigen) and a non-specific antigen.

Candidate scFv were converted to human IgG1-Fc format for production in HEK-293T cells. Briefly, the scFv region was PCR amplified and cloned using infusion cloning (Clontech) in-frame with a leader sequence and the Fc fragment of human IgG1 to create a scFv-Fc gene. scFv-Fc constructs were transfected into HEK-293T cells by calcium phosphate precipitation. Secreted scFv-Fc were purified from the culture media at 48 to 72 h post-transfection by protein A chromatography, followed by concentration and buffer exchange against PBS. Quantification of the purified scFv-Fc was performed using a bicinchoninic acid (BCA) assay (Thermo Scientific, Waltham, Mass.).

Biosensor Binding Kinetics

All biosensor studies were performed in PBS buffer supplemented with 1 mg/ml bovine serum albumin (BSA; PBS-B) at 25° C. using a ForteBio Octet Red biosensor system (Pall-ForteBio, Inc., Menlo Park, Calif.). Streptavidin (SA) biosensor tips were loaded with biotinylated hsGLUT4 VLPs (diluted to 20 µg/ml in PBS-B) for 45 minutes and allowed to stabilize for 10 minutes. Antibody binding and dissociation kinetics were determined for serial dilutions of antibody in PBS-B starting at 20 µg/ml. Antibody association was measured for 5 minutes followed by dissociation for up to 45 minutes in buffer. Non-specific binding was assessed using sensor tips with VLPs containing only endogenous proteins (Null VLPs). Data analysis was performed using the Octet data analysis program (v8.1; ForteBio) using a standard 1:1 binding model.

Flow Cytometry

HEK-293T cells were transfected by $CaPO_4$ with plasmids in 6-well culture plates (Falcon) at 750,000 cells/well. At 48 hours post transfection, cells were stained with anti-V5 and anti-GLUT4 MAbs (purified scFv, 2 µg/ml) followed by biotinylated goat anti-mouse or human antibody (1:500) and streptavidin-PerCP (1:500). Fluorescence was detected using an Intellicyt high-throughput flow cytometer (HTFC; Intellicyt, Albuquerque, NM). For cell permeabilization, cells were treated with saponin at 0.1% in PBS for 20 minutes. To discriminate intact (live) and permeabilized (dead) cells without the use of detergent, propidium iodide (PI) was added to HEK-293T cells at 1 ug/ml just prior to flow cytometry. Where indicated, cytochalasin B (Sigma) was used at a final concentration of 10 uM and phloretin (Sigma) was used at a final concentration of 100 uM, each added in 10% NGS for 30 minutes prior to antibody staining as well as included with the primary antibody.

Western Blot

HEK-293T cells were plated in 6-wells and transfected with plasmids at 8 µg per well via a calcium phosphate transfection. After 48 hours, cells were lysed using 1 ml of RIPA lysis buffer, and lysates were collected and spun at 18,000 RPM for 20 minutes at 4° C. Protein concentration in the supernatant was determined using a bicinchoninic acid (BCA) assay (Pierce). 30 µg of cell lysates and 2 µg of VLPs were further solubilized in Sample Buffer (62.5 mM Tris-HCl, 5% Glycerol, 2% SDS, 0.0025% Bromophenol Blue and 25 mM DTT). Samples were run on a 10% urea gel at 110 volts for 1.33 hours (BioRad). Proteins were transferred onto a PVDF membrane (ThermoFisher) overnight at 4° C. at 22V (BioRad). Membrane was blocked using 5% milk in Blocking buffer (PBS with 0.2% Tween-20) for 0.5 hours and then stained with primary antibodies at a concentration of 2-5 µg/mL in Blocking Buffer for 1 hour. The appropriate HRP secondary antibody (either anti-human or anti-mouse, SouthernBiotech) was used at a 1:5000 dilution in 5% milk in Blocking Buffer for 0.5 hours. Blots were developed using West Femto chemiluminescent substrate (ThermoScientific) and imaged on an Alpha Innotech FluorChem.

Membrane Proteome Array (MPA) Specificity Testing

The MPA is Integral Molecular's cell-based platform of 4,571 different human membrane proteins, each over-expressed in live cells from expression plasmids that are individually transfected in separate wells of a 384-well plate (Huston-Paterson D J, Banik S S, & Doranz B J (2016) Screening the Membrane Proteome. Genetic Engineering & Biotechnology News (September 1):18-19, which is hereby incorporated by reference in its entirety). The entire library is arrayed in duplicate in a matrix format to facilitate testing and analysis. For testing here, the array of plasmids in the MPA was expressed in HEK-293T cells for 24 hours. Prior to testing on the array, primary MAb concentrations were determined using an independent immunofluorescence titration curve against wild type hsGLUT4 to ensure that the signal-to-background was optimal for target detection. Cells were permeabilized with 0.1% saponin, each antibody was added to the MPA at 1 ug/ml, and binding across the protein library was measured using high-throughput flow cytometry (Intellicyt HTFC) using a fluorescent secondary antibody. Each array plate contains both positive (Fc-binding) and negative (empty vector) controls to ensure plate-by-plate data validity. Any identified targets were confirmed in a second flow cytometry experiment using serial dilutions of antibody, and the target identity was re-verified by sequencing.

Shotgun Mutagenesis Epitope Mapping of GLUT4 MAbs

A hsGLUT4 expression construct (accession number P14672) was subjected to high-throughput alanine scanning mutagenesis to generate a comprehensive mutation library. Primers were designed to mutate each residue to alanine, with alanine codons mutated to serine. In total, 508 hsGLUT4 mutants were generated across the entire GLUT4 sequence (residues 2-509), the mutations were sequence confirmed, and the mutants were arrayed into 384-well plates at one mutant per well.

The GLUT4 mutation library, arrayed in 384-well microplates, was transfected into HEK-293T cells and allowed to express for 22 h. Cells were stained with purified MAbs AB102 (0.5 µg/ml), AB105 (1 µg/ml), AB108 (0.5 µg/ml), or AB111 (0.5 µWm') diluted in 10% normal goat serum (NGS; Sigma-Aldrich, St. Louis, Mo.). Primary MAb concentrations were determined using an independent immunofluorescence titration curve against wild type GLUT4 to ensure that the signals were within the linear range of detection. For AB102, binding to the library was measured in the presence of 10 uM cytochalasin B. MAbs were detected using an Alexa Fluor 488-conjugated secondary antibody (Jackson ImmunoResearch Laboratories, West Grove, Pa.) at 3.75 µg/ml in 10% NGS. Cells were washed twice in PBS without calcium or magnesium (PBS−/−) and resuspended in Cellstripper solution (Cellgro, Manassas, Va.) with 0.1% BSA (Sigma-Aldrich, St. Louis, Mo.). Mean cellular fluorescence was detected using an Intellicyt HTFC. MAb reactivities against each mutant GLUT4 clone relative to the reactivity against wild type GLUT4 protein were calculated by subtracting the signal from mock-transfected controls and normalizing the signal to the signal from wild type GLUT4-transfected controls.

Mutated residues within critical clones were identified to be critical to the MAb epitope if they did not support the reactivity of the test MAb but did support the reactivity of a reference GLUT4 MAb and additional GLUT4 MAbs. This counter-screen strategy facilitates the exclusion of GLUT4 mutants that are locally misfolded or that have an expression defect. Residues constituting the MAb epitope were visualized on the homology-based structural model of GLUT4 generated from the crystal structure of GLUT1 (PDB ID 4pyp) using Phyre2.

3T3-L1 Adipocyte Immunofluorescence

3T3-L1 preadipocytes were grown and differentiated into the adipocyte phenotype as previously described (Choi S M, et al. (2010) Insulin regulates adipocyte lipolysis via an Akt-independent signaling pathway. Mol Cell Biol 30(21): 5009-5020, which is incorporated by reference in its entirety).

Adipocytes, between 7-8 days post-differentiation, were serum-starved for 3 hours in Dulbecco's modified Eagle's medium with 220 mM bicarbonate and 20 mM HEPES pH 7.4, prior to stimulation for 20 minutes at 37° C. with or without 170 nM human insulin (Sigma Aldrich) prepared in the same media with 2% BSA. Adipocytes were washed twice with ice-cold PBS with calcium and magnesium (PBS+/+) and remained on ice for all subsequent steps.

Adipocytes were blocked with 10% Normal Goat Serum (NGS) in PBS+/+ for 30 minutes on ice before adding test antibodies at 10 ug/ml in 10% NGS. Primary antibodies were incubated for 2 hours, then washed 2× with PBS+/+. Cells were subsequently fixed for 5 minutes in 4% paraformaldehyde (PFA), washed 2× with PBS+/+, and then stained with secondary antibody (AF488 conjugated Goat anti-human, Jackson Immunoresearch) diluted 1:200 in 10% NGS. Secondary antibody was incubated for 1 hour, after washing 3× with PBS+/+. For intracellular staining, cells were fixed prior to the blocking step and permeabilized with 10% NGS containing 0.2% Saponin. The 1F8 antibody was used at 1 µg/ml, and detected using AF647-conjugated goat anti-mouse secondary antibody diluted 1:400 (Jackson Immunoresearch). Alexafluor 488 was visualized using the B-2EC cube with an exposure time of 1.5 seconds. Alexafluor 647 was visualized using the Cy5 cube with an exposure time of 2 seconds.

2-Deoxyglucose Uptake Assay

HEK-293T cells were transfected with hsGLUT4 expression plasmid or pUC19 control plasmid in poly-L-lysine coated, black 384-well plates with clear bottoms (Costar) and incubated at 37° C. for 22 hours. Growth media was removed and cells were washed three times with PBS+/+ to remove residual glucose. Cells were incubated at 25° C. for 2 hours in PBS (+/+) containing 0.5% BSA, 25-100 ug/ml scFv-Fc, and 10 nM BAY-876 (Sigma-Aldrich) to block endogenous GLUT1 channels. Glucose uptake was initiated by the addition of 1 mM 2-deoxyglucose and allowed to proceed for 20 minutes at 37° C. Cellular 2-deoxyglucose uptake was measured in total cell lysates using the Glucose Uptake-Glo™ kit (Promega), according to the manufacturer's instructions. Luminescence was measured using an Envision, and non-specific luminescence was measured in lysates from cells pre-treated with 10 mM cytochalasin-B.

The embodiments and examples provided herein provide a surprising and unexpected result that antibodies that can bind specifically to GLUT4 in its native environment, such as a cell membrane, can be generated and that inhibitory antibodies can also be generated. Because of the complexity of the protein these results could not have been predicted or expected.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present embodiments are not to be limited in scope by the specific embodiments described herein. Indeed, various modifications in addition to those described herein will become apparent to those skilled in the art from the foregoing description and the accompanying figures. Such modifications are intended to fall within the scope of the embodiments and any appended claims.

The present specification is considered to be sufficient to enable one skilled in the art to practice the embodiments. Various modifications in addition to those shown and described herein will become apparent to those skilled in the art from the foregoing description and fall within the scope of the present disclosure and any appended claims.

What is claimed is:

1. An antibody, or antigen binding fragment thereof, that binds to a GLUT4 protein, wherein the antibody, or antigen binding fragment thereof, comprises a light chain variable ($V_L$) region comprising a light chain CDR1 (LCDR1), a light chain CDR2 (LCDR2), and a light chain CDR3 (LCDR3), and a heavy chain variable ($V_H$) region comprising a heavy chain CDR1 (HCDR1), a heavy chain CDR2 (HCDR2), and a heavy chain CDR3 (HCDR3), wherein:

(i) the LCDR1 has the amino acid sequence of SEQ ID NO: 42; the LCDR2 has the amino acid sequence of SEQ ID NO: 43; the LCDR3 has the amino acid sequence of SEQ ID NO: 44; the HCDR1 has the amino acid sequence of SEQ ID NO: 45; the HCDR2 has the amino acid sequence of SEQ ID NO: 46; and the HCDR3 has the amino acid sequence of SEQ ID NO: 47;

(ii) the LCDR1 has the amino acid sequence of SEQ ID NO: 18; the LCDR2 has the amino acid sequence of SEQ ID NO: 19; the LCDR3 has the amino acid sequence of SEQ ID NO: 20; the HCDR1 has the amino acid sequence of SEQ ID NO: 21; the HCDR2 has the amino acid sequence of SEQ ID NO: 22; and the HCDR3 has the amino acid sequence of SEQ ID NO: 23;

(iii) the LCDR1 has the amino acid sequence of SEQ ID NO: 24; the LCDR2 has the amino acid sequence of SEQ ID NO: 25; the LCDR3 has the amino acid sequence of SEQ ID NO: 26; the HCDR1 has the amino acid sequence of SEQ ID NO: 27; the HCDR2 has the amino acid sequence of SEQ ID NO: 28; and the HCDR3 has the amino acid sequence of SEQ ID NO: 29;

(iv) the LCDR1 has the amino acid sequence of SEQ ID NO: 60; the LCDR2 has the amino acid sequence of SEQ ID NO: 61; the LCDR3 has the amino acid sequence of SEQ ID NO: 62; the HCDR1 has the amino acid sequence of SEQ ID NO: 63; the HCDR2 has the amino acid sequence of SEQ ID NO: 64; and the HCDR3 has the amino acid sequence of SEQ ID NO: 65; or (v) the LCDR1 has the amino acid sequence of SEQ ID NO: 78; the LCDR2 has the amino acid sequence of SEQ ID NO: 79; the LCDR3 has the amino acid sequence of SEQ ID NO: 80; the HCDR1 has the amino acid sequence of SEQ ID NO: 81; the HCDR2 has the amino acid sequence of SEQ ID NO: 82; and the HCDR3 has the amino acid sequence of SEQ ID NO: 83.

2. The antibody, or antigen binding fragment thereof, of claim 1, wherein:

(i) the $V_L$ region comprises an amino acid sequence that is at least 95% identical to SEQ ID NO: 10, provided that the LCDR1 has the amino acid sequence of SEQ ID NO: 42, the LCDR2 has the amino acid sequence of SEQ ID NO: 43, and the LCDR3 has the amino acid sequence SEQ ID NO: 44;

(ii) the $V_L$ region comprises an amino acid sequence that is at least 95% identical to SEQ ID NO: 8, provided that the LCDR1 has the amino acid sequence of SEQ ID NO: 18, the LCDR2 has the amino acid sequence of SEQ ID NO: 19, and the LCDR3 has the amino acid sequence SEQ ID NO: 20;

(iii) the $V_L$ region comprises an amino acid sequence that is at least 95% identical to SEQ ID NO: 9, provided that the LCDR1 has the amino acid sequence of SEQ ID NO: 24, the LCDR2 has the amino acid sequence of SEQ ID NO: 25, and the LCDR3 has the amino acid sequence SEQ ID NO: 26;

(iv) the $V_L$ region comprises an amino acid sequence that is at least 95% identical to SEQ ID NO: 11, provided that the LCDR1 has the amino acid sequence of SEQ ID NO: 60, the LCDR2 has the amino acid sequence of SEQ ID NO: 61, and the LCDR3 has the amino acid sequence SEQ ID NO: 62; or (v) the $V_L$ region comprises an amino acid sequence that is at least 95% identical to SEQ ID NO: 12, provided that the LCDR1 has the amino acid sequence of SEQ ID NO: 78, the LCDR2 has the amino acid sequence of SEQ ID NO: 79, and the LCDR3 has the amino acid sequence SEQ ID NO: 80.

3. The antibody, or antigen binding fragment thereof, of claim 1, wherein:

(i) the $V_H$ region comprises an amino acid sequence that is at least 95% identical to SEQ ID NO: 15, provided that the HCDR1 has the amino acid sequence of SEQ ID NO: 42, the HCDR2 has the amino acid sequence of SEQ ID NO: 43, and the HCDR3 has the amino acid sequence SEQ ID NO: 44;

(ii) the $V_H$ region comprises an amino acid sequence that is at least 95% identical to SEQ ID NO: 13, provided that the HCDR1 has the amino acid sequence of SEQ ID NO: 21, the HCDR2 has the amino acid sequence of SEQ ID NO: 22, and the HCDR3 has the amino acid sequence SEQ ID NO: 23;

(iii) the $V_H$ region comprises an amino acid sequence that is at least 95% identical to SEQ ID NO: 14, provided that the HCDR1 has the amino acid sequence of SEQ ID NO: 27, the HCDR2 has the amino acid sequence of SEQ ID NO: 28, and the HCDR3 has the amino acid sequence SEQ ID NO: 29;

(iv) the $V_H$ region comprises an amino acid sequence that is at least 95% identical to SEQ ID NO: 16, provided that the HCDR1 has the amino acid sequence of SEQ ID NO: 63, the HCDR2 has the amino acid sequence of SEQ ID NO: 64, and the HCDR3 has the amino acid sequence SEQ ID NO: 65; or (v) the $V_H$ region comprises an amino acid sequence that is at least 95% identical to SEQ ID NO: 17, provided that the HCDR1 has the amino acid sequence of SEQ ID NO: 81, the HCDR2 has the amino acid sequence of SEQ ID NO: 82, and the HCDR3 has the amino acid sequence SEQ ID NO: 83.

4. The antibody, or antigen binding fragment thereof, of claim 1, wherein:

(i) the $V_L$ region comprises an amino acid sequence that is at least 95% identical to SEQ ID NO: 10, provided that the LCDR1 has the amino acid sequence of SEQ ID NO: 42, the LCDR2 has the amino acid sequence of SEQ ID NO: 43, and the LCDR3 has the amino acid sequence SEQ ID NO: 44; and the $V_H$ region comprises an amino acid sequence that is at least 95% identical to SEQ ID NO: 15, provided that the HCDR1 has the amino acid sequence of SEQ ID NO: 42, the HCDR2 has the amino acid sequence of SEQ ID NO: 43, and the HCDR3 has the amino acid sequence SEQ ID NO: 44;

(ii) the $V_L$ region comprises an amino acid sequence that is at least 95% identical to SEQ ID NO: 8, provided that the LCDR1 has the amino acid sequence of SEQ ID NO: 18, the LCDR2 has the amino acid sequence of SEQ ID NO: 19, and the LCDR3 has the amino acid sequence SEQ ID NO: 20; and the $V_H$ region comprises an amino acid sequence that is at least 95% identical to SEQ ID NO: 13, provided that the HCDR1 has the amino acid sequence of SEQ ID NO: 21, the HCDR2 has the amino acid sequence of SEQ ID NO: 22, and the HCDR3 has the amino acid sequence SEQ ID NO: 23;
(iii) the $V_L$ region comprises an amino acid sequence that is at least 95% identical to SEQ ID NO: 9, provided that the LCDR1 has the amino acid sequence of SEQ ID NO: 24, the LCDR2 has the amino acid sequence of SEQ ID NO: 25, and the LCDR3 has the amino acid sequence SEQ ID NO: 26; and the $V_H$ region comprises an amino acid sequence that is at least 95% identical to SEQ ID NO: 14, provided that the HCDR1 has the amino acid sequence of SEQ ID NO: 27, the HCDR2 has the amino acid sequence of SEQ ID NO: 28, and the HCDR3 has the amino acid sequence SEQ ID NO: 29;
(iv) the $V_L$ region comprises an amino acid sequence that is at least 95% identical to SEQ ID NO: 11, provided that LCDR1 has the amino acid sequence of SEQ ID NO: 60, the LCDR2 has the amino acid sequence of SEQ ID NO: 61, and the LCDR3 has the amino acid sequence SEQ ID NO: 62; and the $V_H$ region comprises an amino acid sequence that is at least 95% identical to SEQ ID NO: 16, provided that the HCDR1 has the amino acid sequence of SEQ ID NO: 63, the HCDR2 has the amino acid sequence of SEQ ID NO: 64, and the HCDR3 has the amino acid sequence SEQ ID NO: 65: or
(v) the $V_L$ region comprises an amino acid sequence that is at least 95% identical to SEQ ID NO: 12, provided that the LCDR1 has the amino acid sequence of SEQ ID NO: 78, the LCDR2 has the amino acid sequence of SEQ ID NO: 79, and the LCDR3 has the amino acid sequence SEQ ID NO: 80 and the $V_H$ region comprising an amino acid sequence that is at least 95% identical to SEQ ID NO: 17, provided that the HCDR1 has the amino acid sequence of SEQ ID NO: 81, the HCDR2 has the amino acid sequence of SEQ ID NO: 82, and the HCDR3 has the amino acid sequence SEQ ID NO: 83.

5. A nucleic acid molecule encoding an antibody, or antigen binding fragment thereof, of claim 1.

6. A pharmaceutical composition comprising the antibody, or antigen binding fragment thereof, of claim 1 or a nucleic acid molecule encoding the same.

7. A method of modulating GLUT4 internalization, the method comprising contacting a cell expressing GLUT4 with a GLUT4 antibody, or antigen binding fragment thereof, of claim 1 or a pharmaceutical composition comprising the same.

8. The antibody, or antigen binding fragment thereof, of claim 1, wherein the antibody, or antigen binding fragment thereof, comprises:
(i) a $V_L$ region comprising an amino acid sequence of SEQ ID NO: 10;
(ii) a $V_L$ region comprising an amino acid sequence of SEQ ID NO: 8;
(iii) a $V_L$ region comprising an amino acid sequence of SEQ ID NO: 9;
(iv) a $V_L$ region comprising an amino acid sequence of SEQ ID NO: 11; or
(v) a $V_L$ region comprising an amino acid sequence of SEQ ID NO: 12.

9. The antibody, or antigen binding fragment thereof, of claim 1, wherein the antibody, or antigen binding fragment thereof, comprises:
(i) a $V_H$ region comprising an amino acid sequence of SEQ ID NO: 15;
(ii) a $V_H$ region comprising an amino acid sequence of SEQ ID NO: 13;
(iii) a $V_H$ region comprising an amino acid sequence of SEQ ID NO: 14;
(iv) a $V_H$ region comprising an amino acid sequence of SEQ ID NO: 16; or
(v) a $V_H$ region comprising an amino acid sequence of SEQ ID NO: 17.

10. The antibody, or antigen binding fragment thereof, of claim 1, wherein the antibody, or antigen binding fragment thereof, comprises:
(i) a $V_L$ region comprising an amino acid sequence of SEQ ID NO: 10, and a $V_H$ region comprising an amino acid sequence of SEQ ID NO: 15;
(ii) a $V_L$ region comprising an amino acid sequence of SEQ ID NO: 8, and a $V_H$ region comprising an amino acid sequence of SEQ ID NO: 13;
(iii) a $V_L$ region comprising an amino acid sequence of SEQ ID NO: 9, and a $V_H$ region comprising an amino acid sequence of SEQ ID NO: 14;
(iv) a $V_L$ region comprising an amino acid sequence of SEQ ID NO: 11, and a $V_H$ region comprising an amino acid sequence of SEQ ID NO: 16; or
(v) a $V_L$ region comprising an amino acid sequence of SEQ ID NO: 12, and a $V_H$ region comprising an amino acid sequence of SEQ ID NO: 17.

* * * * *

SEQUENCE LISTING

```
<160> NUMBER OF SEQ ID NOS: 122

<210> SEQ ID NO 1
<211> LENGTH: 509
<212> TYPE: PRT
<213> ORGANISM: Homo sapiens

<400> SEQUENCE: 1

Met Pro Ser Gly Phe Gln Gln Ile Gly Ser Glu Asp Gly Glu Pro Pro
1               5                   10                  15

Gln Gln Arg Val Thr Gly Thr Leu Val Leu Ala Val Phe Ser Ala Val
            20                  25                  30

Leu Gly Ser Leu Gln Phe Gly Tyr Asn Ile Gly Val Ile Asn Ala Pro
        35                  40                  45

Gln Lys Val Ile Glu Gln Ser Tyr Asn Glu Thr Trp Leu Gly Arg Gln
    50                  55                  60

Gly Pro Glu Gly Pro Ser Ser Ile Pro Pro Gly Thr Leu Thr Thr Leu
65                  70                  75                  80

Trp Ala Leu Ser Val Ala Ile Phe Ser Val Gly Gly Met Ile Ser Ser
                85                  90                  95

Phe Leu Ile Gly Ile Ile Ser Gln Trp Leu Gly Arg Lys Arg Ala Met
                100                 105                 110

Leu Val Asn Asn Val Leu Ala Val Leu Gly Gly Ser Leu Met Gly Leu
            115                 120                 125
```

Ala Asn Ala Ala Ala Ser Tyr Glu Met Leu Ile Leu Gly Arg Phe Leu
            130                 135                 140

Ile Gly Ala Tyr Ser Gly Leu Thr Ser Gly Leu Val Pro Met Tyr Val
145                 150                 155                 160

Gly Glu Ile Ala Pro Thr His Leu Arg Gly Ala Leu Gly Thr Leu Asn
                165                 170                 175

Gln Leu Ala Ile Val Ile Gly Ile Leu Ile Ala Gln Val Leu Gly Leu
            180                 185                 190

Glu Ser Leu Leu Gly Thr Ala Ser Leu Trp Pro Leu Leu Gly Leu
        195                 200                 205

Thr Val Leu Pro Ala Leu Leu Gln Leu Val Leu Leu Pro Phe Cys Pro
210                 215                 220

Glu Ser Pro Arg Tyr Leu Tyr Ile Ile Gln Asn Leu Glu Gly Pro Ala
225                 230                 235                 240

Arg Lys Ser Leu Lys Arg Leu Thr Gly Trp Ala Asp Val Ser Gly Val
                245                 250                 255

Leu Ala Glu Leu Lys Asp Glu Lys Arg Lys Leu Glu Arg Glu Arg Pro
            260                 265                 270

Leu Ser Leu Leu Gln Leu Leu Gly Ser Arg Thr His Arg Gln Pro Leu
        275                 280                 285

Ile Ile Ala Val Val Leu Gln Leu Ser Gln Gln Leu Ser Gly Ile Asn
290                 295                 300

Ala Val Phe Tyr Tyr Ser Thr Ser Ile Phe Glu Thr Ala Gly Val Gly
305                 310                 315                 320

Gln Pro Ala Tyr Ala Thr Ile Gly Ala Gly Val Val Asn Thr Val Phe
                325                 330                 335

Thr Leu Val Ser Val Leu Leu Val Glu Arg Ala Gly Arg Arg Thr Leu
            340                 345                 350

His Leu Leu Gly Leu Ala Gly Met Cys Gly Cys Ala Ile Leu Met Thr
        355                 360                 365

Val Ala Leu Leu Leu Leu Glu Arg Val Pro Ala Met Ser Tyr Val Ser
370                 375                 380

Ile Val Ala Ile Phe Gly Phe Val Ala Phe Phe Glu Ile Gly Pro Gly
385                 390                 395                 400

Pro Ile Pro Trp Phe Ile Val Ala Glu Leu Phe Ser Gln Gly Pro Arg
                405                 410                 415

Pro Ala Ala Met Ala Val Ala Gly Phe Ser Asn Trp Thr Ser Asn Phe
            420                 425                 430

Ile Ile Gly Met Gly Phe Gln Tyr Val Ala Glu Ala Met Gly Pro Tyr
        435                 440                 445

Val Phe Leu Leu Phe Ala Val Leu Leu Leu Gly Phe Phe Ile Phe Thr
450                 455                 460

Phe Leu Arg Val Pro Glu Thr Arg Gly Arg Thr Phe Asp Gln Ile Ser
465                 470                 475                 480

Ala Ala Phe His Arg Thr Pro Ser Leu Leu Gln Glu Val Lys Pro
                485                 490                 495

Ser Thr Glu Leu Glu Tyr Leu Gly Pro Asp Glu Asn Asp
            500                 505

<210> SEQ ID NO 2
<211> LENGTH: 246
<212> TYPE: PRT
<213> ORGANISM: Artificial Sequence
<220> FEATURE:
<223> OTHER INFORMATION: Recombinant antibody fragment

<400> SEQUENCE: 2

```
Ala Leu Thr Gln Pro Ser Ser Val Ser Ala Asn Pro Gly Glu Thr Val
1               5                   10                  15
Lys Ile Thr Cys Ser Gly Ser Ser Asn Ser Tyr Gly Trp Tyr Gln Gln
            20                  25                  30
Lys Ser Pro Gly Ser Ala Pro Val Thr Val Ile Tyr Tyr Asn Asp Lys
        35                  40                  45
Arg Pro Ser Asp Ile Pro Ser Arg Phe Ser Gly Lys Ser Asp Ser
    50                  55                  60
Thr His Thr Leu Thr Ile Thr Gly Val Arg Ala Glu Asp Glu Ala Val
65                  70                  75                  80
Tyr Phe Cys Gly Ser Tyr Asp Ser Thr Tyr Val Gly Ile Phe Gly Ala
                85                  90                  95
Gly Thr Thr Leu Thr Val Leu Gly Gln Ser Ser Arg Ser Ser Gly Gly
            100                 105                 110
Gly Gly Ser Ser Gly Gly Gly Ser Ala Val Thr Leu Asp Glu Ser
        115                 120                 125
Gly Gly Gly Leu Gln Thr Pro Gly Gly Thr Leu Ser Leu Val Cys Lys
130                 135                 140
Ala Ser Gly Phe Thr Phe Ser Ser Asn Ala Met Gly Trp Val Arg Gln
145                 150                 155                 160
Ala Pro Gly Lys Gly Leu Glu Trp Val Ala Gly Ile Ser Ser Asp Gly
                165                 170                 175
Arg Tyr Thr Lys Tyr Gly Ser Ala Val Lys Gly Arg Ala Thr Ile Ser
            180                 185                 190
Arg Asp Asn Gly Gln Ser Thr Val Arg Leu Gln Leu Asn Asn Leu Arg
        195                 200                 205
Ala Glu Asp Thr Gly Thr Tyr Phe Cys Ala Lys Ala Phe Gly Asn Asn
    210                 215                 220
Tyr Arg Arg Ile Tyr Ala Gly Gln Ile Asp Ala Trp Gly His Gly Thr
225                 230                 235                 240
Glu Val Ile Val Ser Ser
                245
```

<210> SEQ ID NO 3
<211> LENGTH: 249
<212> TYPE: PRT
<213> ORGANISM: Artificial Sequence
<220> FEATURE:
<223> OTHER INFORMATION: Recombinant antibody fragment

<400> SEQUENCE: 3

```
Ala Leu Thr Gln Pro Ser Ser Val Ser Ala Asn Leu Gly Gly Thr Val
1               5                   10                  15
Lys Ile Thr Cys Ser Gly Gly Gly Ser Tyr Gly Tyr Gly Trp Tyr Gln
            20                  25                  30
Gln Lys Ser Pro Gly Ser Ala Pro Val Thr Val Ile Tyr Ser Asn Asp
        35                  40                  45
Gln Arg Pro Ser Asp Ile Pro Ser Arg Phe Ser Gly Ser Lys Ser Gly
    50                  55                  60
Ser Thr Ala Thr Leu Thr Ile Thr Gly Val Arg Ala Glu Asp Glu Ala
65                  70                  75                  80
Ile Tyr Tyr Cys Gly Ser Thr Asp Ser Asp Tyr Val Gly Ile Phe Gly
                85                  90                  95
```

```
Ala Gly Thr Thr Leu Thr Val Leu Gly Gln Ser Ser Arg Ser Ser Gly
            100                 105                 110

Gly Gly Gly Ser Ser Gly Gly Gly Ser Ala Val Thr Leu Asp Glu
        115                 120                 125

Ser Gly Gly Gly Leu Gln Thr Pro Gly Gly Thr Leu Ser Leu Val Cys
130                 135                 140

Lys Ala Ser Gly Phe Asp Phe Ser Ser Tyr Ala Thr Ile Trp Val Arg
145                 150                 155                 160

Gln Ala Pro Gly Lys Gly Leu Glu Trp Val Ala Gly Ile Ser Gly Thr
                165                 170                 175

Gly Thr Gly Ser Ser Thr Gly Tyr Ala Pro Ala Val Lys Gly Arg Ala
            180                 185                 190

Thr Ile Ser Arg Asp Asn Gly Gln Ser Thr Val Arg Leu Gln Leu Asn
            195                 200                 205

Asn Leu Arg Ala Glu Asp Thr Gly Ser Tyr Phe Cys Ala Lys Ser Thr
        210                 215                 220

Gly Tyr Gly Asp Ser Trp Ile Tyr Pro Asp Ser Ile Asp Ala Trp Gly
225                 230                 235                 240

His Gly Thr Glu Val Ile Val Ser Ser
                245
```

<210> SEQ ID NO 4
<211> LENGTH: 254
<212> TYPE: PRT
<213> ORGANISM: Artificial Sequence
<220> FEATURE:
<223> OTHER INFORMATION: Recombinant antibody fragment

<400> SEQUENCE: 4

```
Ala Leu Thr Gln Pro Ser Ser Val Ser Ala Asn Pro Gly Glu Thr Val
1               5                   10                  15

Glu Ile Thr Cys Ser Gly Asp Ser Ser Tyr Tyr Gly Trp Tyr Gln Gln
                20                  25                  30

Lys Ser Pro Gly Ser Ala Pro Val Thr Val Ile Tyr Ala Asn Thr Asn
            35                  40                  45

Arg Pro Ser Asp Ile Pro Ser Arg Phe Ser Gly Ser Ala Ser Gly Ser
        50                  55                  60

Thr Ala Thr Leu Thr Ile Thr Gly Val Gln Ala Glu Asp Glu Ala Val
65                  70                  75                  80

Tyr Tyr Cys Gly Ser Ala Asp Ser Thr Tyr Ala Gly Ile Phe Gly Ala
                85                  90                  95

Gly Thr Thr Leu Thr Val Leu Gly Gln Ser Ser Arg Ser Ser Gly Gly
            100                 105                 110

Gly Gly Ser Ser Gly Gly Gly Ser Ala Val Thr Leu Asp Glu Ser
        115                 120                 125

Gly Gly Gly Leu Gln Thr Pro Gly Gly Ala Leu Ser Leu Ile Cys Lys
130                 135                 140

Ala Ser Gly Phe Thr Phe Ser Ser Tyr Thr Met Asn Trp Val Arg Gln
145                 150                 155                 160

Ala Pro Gly Lys Gly Leu Glu Trp Val Gly Val Ile Ser Asn Ser Gly
                165                 170                 175

Arg Thr Thr Asn Tyr Gly Ala Ala Val Gln Gly Arg Ala Thr Ile Ser
            180                 185                 190

Arg Asp Asn Gly Gln Ser Thr Val Arg Leu Gln Leu Asn Asn Leu Arg
        195                 200                 205
```

```
Ala Glu Asp Thr Gly Thr Tyr Tyr Cys Ala Lys Ser Ser Ala Ser Ala
    210                 215                 220

Ser Cys Ala Trp Trp Ala Gly Arg Ser Tyr Pro Cys Ser Ala Asn Arg
225                 230                 235                 240

Ile Asp Ala Trp Gly His Gly Thr Glu Val Ile Val Ser Ser
                245                 250
```

<210> SEQ ID NO 5
<211> LENGTH: 244
<212> TYPE: PRT
<213> ORGANISM: Artificial Sequence
<220> FEATURE:
<223> OTHER INFORMATION: Recombinant antibody fragment

<400> SEQUENCE: 5

```
Ala Leu Thr Gln Pro Ser Ser Val Ser Ala Asn Leu Gly Gly Thr Val
1               5                   10                  15

Lys Ile Thr Cys Ser Gly Ser Ser Gly Ser Tyr Gly Trp Tyr Gln Gln
            20                  25                  30

Lys Ala Pro Gly Ser Ala Pro Val Thr Leu Ile Tyr Arg Asn Asp Lys
        35                  40                  45

Arg Pro Ser Asp Ile Pro Ser Arg Phe Ser Gly Ser Glu Ser Gly Ser
    50                  55                  60

Thr Gly Thr Leu Thr Ile Thr Gly Val Gln Ala Glu Asp Glu Ala Val
65                  70                  75                  80

Tyr Phe Cys Gly Gly Tyr Asp Ser Ser Ala Gly Tyr Ala Ala Phe Gly
                85                  90                  95

Ala Gly Thr Thr Leu Thr Val Leu Gly Gln Ser Ser Arg Ser Ser Gly
            100                 105                 110

Gly Gly Gly Ser Ser Gly Gly Gly Ser Ala Val Thr Leu Asp Glu
        115                 120                 125

Ser Gly Gly Gly Leu Gln Thr Pro Gly Gly Ala Leu Ser Leu Val Cys
    130                 135                 140

Lys Ala Ser Gly Phe Thr Phe Ser Ser His Gly Met Gly Trp Val Arg
145                 150                 155                 160

Gln Ala Pro Gly Lys Gly Leu Glu Trp Val Gly Ser Ile Ser Thr Gly
                165                 170                 175

Arg Tyr Thr Phe Tyr Ala Pro Ala Val Lys Gly Arg Ala Thr Ile Ser
            180                 185                 190

Arg Asp Asn Gly Gln Ser Thr Leu Arg Leu Gln Leu Asn Asn Leu Arg
        195                 200                 205

Ala Glu Asp Thr Gly Thr Tyr Tyr Cys Thr Lys Cys Ala Gly Leu Asn
    210                 215                 220

Gly Cys Gly Gly Gly Glu Ile Asp Ala Trp Gly His Gly Thr Glu Val
225                 230                 235                 240

Ile Val Ser Ser
```

<210> SEQ ID NO 6
<211> LENGTH: 238
<212> TYPE: PRT
<213> ORGANISM: Artificial Sequence
<220> FEATURE:
<223> OTHER INFORMATION: Recombinant antibody fragment

<400> SEQUENCE: 6

```
Ala Leu Thr Gln Pro Ser Ser Val Ser Ala Asn Pro Gly Glu Thr Val
1               5                   10                  15
```

```
Lys Ile Thr Cys Ser Gly Ser Gly Ser Trp Tyr Gly Trp Phe Gln Gln
                20                  25                  30

Lys Ser Pro Gly Ser Ala Pro Val Thr Val Ile Tyr Ser Asn Asp Lys
            35                  40                  45

Arg Pro Ser Asp Ile Pro Ser Arg Phe Ser Gly Ser Lys Ser Gly Ser
    50                  55                  60

Thr Ser Thr Leu Thr Ile Thr Gly Val Gln Val Glu Asp Glu Ala Val
65                  70                  75                  80

Tyr Tyr Cys Gly Asn Trp Asp Ile Phe Gly Ala Gly Thr Thr Leu Thr
                85                  90                  95

Val Leu Gly Gln Ser Ser Arg Ser Ser Gly Gly Gly Ser Ser Gly
            100                 105                 110

Gly Gly Gly Ser Ala Val Thr Leu Asp Glu Ser Gly Gly Leu Gln
            115                 120                 125

Thr Pro Gly Gly Ala Leu Ser Leu Val Cys Lys Ala Ser Gly Phe Thr
    130                 135                 140

Phe Ser Ser His Gly Met Gly Trp Val Arg Gln Ala Pro Gly Lys Gly
145                 150                 155                 160

Leu Glu Trp Val Ala Ser Ile Ser Thr Gly Arg Tyr Thr Phe Tyr Ala
                165                 170                 175

Pro Ala Val Lys Gly Arg Ala Thr Ile Ser Arg Asp Asn Gly Gln Ser
            180                 185                 190

Thr Val Arg Leu Gln Leu Asn Asn Leu Arg Ala Glu Asp Thr Ala Thr
    195                 200                 205

Tyr Tyr Cys Thr Lys Cys Ala Gly Leu Asn Gly Cys Gly Gly Glu
                210                 215                 220

Ile Asp Ala Trp Gly His Gly Thr Glu Val Ile Val Ser Ser
225                 230                 235

<210> SEQ ID NO 7

<400> SEQUENCE: 7

000

<210> SEQ ID NO 8
<211> LENGTH: 103
<212> TYPE: PRT
<213> ORGANISM: Artificial Sequence
<220> FEATURE:
<223> OTHER INFORMATION: Recombinant antibody fragment

<400> SEQUENCE: 8

Ala Leu Thr Gln Pro Ser Ser Val Ser Ala Asn Pro Gly Glu Thr Val
1               5                   10                  15

Lys Ile Thr Cys Ser Gly Ser Ser Asn Ser Tyr Gly Trp Tyr Gln Gln
                20                  25                  30

Lys Ser Pro Gly Ser Ala Pro Val Thr Val Ile Tyr Tyr Asn Asp Lys
            35                  40                  45

Arg Pro Ser Asp Ile Pro Ser Arg Phe Ser Gly Ser Lys Ser Asp Ser
    50                  55                  60

Thr His Thr Leu Thr Ile Thr Gly Val Arg Ala Glu Asp Glu Ala Val
65                  70                  75                  80

Tyr Phe Cys Gly Ser Tyr Asp Ser Thr Tyr Val Gly Ile Phe Gly Ala
                85                  90                  95

Gly Thr Thr Leu Thr Val Leu
            100
```

<210> SEQ ID NO 9
<211> LENGTH: 104
<212> TYPE: PRT
<213> ORGANISM: Artificial Sequence
<220> FEATURE:
<223> OTHER INFORMATION: Recombinant antibody fragment

<400> SEQUENCE: 9

Ala Leu Thr Gln Pro Ser Ser Val Ser Ala Asn Leu Gly Gly Thr Val
1               5                   10                  15

Lys Ile Thr Cys Ser Gly Gly Gly Ser Tyr Gly Tyr Gly Trp Tyr Gln
                20                  25                  30

Gln Lys Ser Pro Gly Ser Ala Pro Val Thr Val Ile Tyr Ser Asn Asp
            35                  40                  45

Gln Arg Pro Ser Asp Ile Pro Ser Arg Phe Ser Gly Ser Lys Ser Gly
        50                  55                  60

Ser Thr Ala Thr Leu Thr Ile Thr Gly Val Arg Ala Glu Asp Glu Ala
65                  70                  75                  80

Ile Tyr Tyr Cys Gly Ser Thr Asp Ser Asp Tyr Val Gly Ile Phe Gly
                85                  90                  95

Ala Gly Thr Thr Leu Thr Val Leu
            100

<210> SEQ ID NO 10
<211> LENGTH: 103
<212> TYPE: PRT
<213> ORGANISM: Artificial Sequence
<220> FEATURE:
<223> OTHER INFORMATION: Recombinant antibody fragment

<400> SEQUENCE: 10

Ala Leu Thr Gln Pro Ser Ser Val Ser Ala Asn Pro Gly Glu Thr Val
1               5                   10                  15

Glu Ile Thr Cys Ser Gly Asp Ser Ser Tyr Tyr Gly Trp Tyr Gln Gln
                20                  25                  30

Lys Ser Pro Gly Ser Ala Pro Val Thr Val Ile Tyr Ala Asn Thr Asn
            35                  40                  45

Arg Pro Ser Asp Ile Pro Ser Arg Phe Ser Gly Ser Ala Ser Gly Ser
        50                  55                  60

Thr Ala Thr Leu Thr Ile Thr Gly Val Gln Ala Glu Asp Glu Ala Val
65                  70                  75                  80

Tyr Tyr Cys Gly Ser Ala Asp Ser Thr Tyr Ala Gly Ile Phe Gly Ala
                85                  90                  95

Gly Thr Thr Leu Thr Val Leu
            100

<210> SEQ ID NO 11
<211> LENGTH: 104
<212> TYPE: PRT
<213> ORGANISM: Artificial Sequence
<220> FEATURE:
<223> OTHER INFORMATION: Recombinant antibody fragment

<400> SEQUENCE: 11

Ala Leu Thr Gln Pro Ser Ser Val Ser Ala Asn Leu Gly Gly Thr Val
1               5                   10                  15

Lys Ile Thr Cys Ser Gly Ser Ser Ser Tyr Gly Trp Tyr Gln Gln
                20                  25                  30

Lys Ala Pro Gly Ser Ala Pro Val Thr Leu Ile Tyr Arg Asn Asp Lys
            35                  40                  45

Arg Pro Ser Asp Ile Pro Ser Arg Phe Ser Gly Ser Glu Ser Gly Ser
 50                  55                  60

Thr Gly Thr Leu Thr Ile Thr Gly Val Gln Ala Glu Asp Glu Ala Val
65                  70                  75                  80

Tyr Phe Cys Gly Gly Tyr Asp Ser Ser Ala Gly Tyr Ala Ala Phe Gly
                85                  90                  95

Ala Gly Thr Thr Leu Thr Val Leu
            100

<210> SEQ ID NO 12
<211> LENGTH: 98
<212> TYPE: PRT
<213> ORGANISM: Artificial Sequence
<220> FEATURE:
<223> OTHER INFORMATION: Recombinant antibody fragment

<400> SEQUENCE: 12

Ala Leu Thr Gln Pro Ser Ser Val Ser Ala Asn Pro Gly Glu Thr Val
1               5                   10                  15

Lys Ile Thr Cys Ser Gly Ser Gly Ser Trp Tyr Gly Trp Phe Gln Gln
            20                  25                  30

Lys Ser Pro Gly Ser Ala Pro Val Thr Val Ile Tyr Ser Asn Asp Lys
            35                  40                  45

Arg Pro Ser Asp Ile Pro Ser Arg Phe Ser Gly Ser Lys Ser Gly Ser
 50                  55                  60

Thr Ser Thr Leu Thr Ile Thr Gly Val Gln Val Glu Asp Glu Ala Val
65                  70                  75                  80

Tyr Tyr Cys Gly Asn Trp Asp Ile Phe Gly Ala Gly Thr Thr Leu Thr
                85                  90                  95

Val Leu

<210> SEQ ID NO 13
<211> LENGTH: 125
<212> TYPE: PRT
<213> ORGANISM: Artificial Sequence
<220> FEATURE:
<223> OTHER INFORMATION: Recombinant antibody fragment

<400> SEQUENCE: 13

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val
            35                  40                  45

Ala Gly Ile Ser Ser Asp Gly Arg Tyr Thr Lys Tyr Gly Ser Ala Val
 50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Phe Cys
                85                  90                  95

Ala Lys Ala Phe Gly Asn Asn Tyr Arg Arg Ile Tyr Ala Gly Gln Ile
            100                 105                 110

Asp Ala Trp Gly His Gly Thr Glu Val Ile Val Ser Ser
            115                 120                 125

<210> SEQ ID NO 14
<211> LENGTH: 127
<212> TYPE: PRT
<213> ORGANISM: Artificial Sequence
<220> FEATURE:
<223> OTHER INFORMATION: Recombinant antibody fragment

<400> SEQUENCE: 14

```
Ala Val Thr Leu Asp Glu Ser Gly Gly Leu Gln Thr Pro Gly Gly
1               5                   10                  15

Thr Leu Ser Leu Val Cys Lys Ala Ser Gly Phe Asp Phe Ser Ser Tyr
            20                  25                  30

Ala Thr Ile Trp Val Arg Gln Ala Pro Gly Lys Gly Leu Glu Trp Val
        35                  40                  45

Ala Gly Ile Ser Gly Thr Gly Thr Gly Ser Ser Thr Gly Tyr Ala Pro
    50                  55                  60

Ala Val Lys Gly Arg Ala Thr Ile Ser Arg Asp Asn Gly Gln Ser Thr
65                  70                  75                  80

Val Arg Leu Gln Leu Asn Asn Leu Arg Ala Glu Asp Thr Gly Ser Tyr
                85                  90                  95

Phe Cys Ala Lys Ser Thr Gly Tyr Gly Asp Ser Trp Ile Tyr Pro Asp
            100                 105                 110

Ser Ile Asp Ala Trp Gly His Gly Thr Glu Val Ile Val Ser Ser
        115                 120                 125
```

<210> SEQ ID NO 15
<211> LENGTH: 133
<212> TYPE: PRT
<213> ORGANISM: Artificial Sequence
<220> FEATURE:
<223> OTHER INFORMATION: Recombinant antibody fragment

<400> SEQUENCE: 15

```
Ala Val Thr Leu Asp Glu Ser Gly Gly Leu Gln Thr Pro Gly Gly
1               5                   10                  15

Ala Leu Ser Leu Ile Cys Lys Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Gly Val Ile Ser Asn Ser Gly Arg Thr Thr Asn Tyr Gly Ala Ala Val
    50                  55                  60

Gln Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Ser Ser Ala Ser Ala Ser Cys Ala Trp Trp Ala Gly Arg Ser
            100                 105                 110

Tyr Pro Cys Ser Ala Asn Arg Ile Asp Ala Trp Gly His Gly Thr Glu
        115                 120                 125

Val Ile Val Ser Ser
    130
```

<210> SEQ ID NO 16
<211> LENGTH: 122
<212> TYPE: PRT
<213> ORGANISM: Artificial Sequence
<220> FEATURE:
<223> OTHER INFORMATION: Recombinant antibody fragment

<400> SEQUENCE: 16

Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Ser His
            20                  25                  30

Gly Met Gly Trp Val Arg Gln Ala Pro Gly Lys Gly Leu Glu Trp Val
        35                  40                  45

Gly Ser Ile Ser Thr Gly Arg Tyr Thr Phe Tyr Ala Pro Ala Val Lys
    50                  55                  60

Gly Arg Ala Thr Ile Ser Arg Asp Asn Gly Gln Ser Thr Leu Arg Leu
65                  70                  75                  80

Gln Leu Asn Asn Leu Arg Ala Glu Asp Thr Gly Thr Tyr Tyr Cys Thr
                85                  90                  95

Lys Cys Ala Gly Leu Asn Gly Cys Gly Gly Glu Ile Asp Ala Trp
            100                 105                 110

Gly His Gly Thr Glu Val Ile Val Ser Ser
        115                 120

<210> SEQ ID NO 17
<211> LENGTH: 122
<212> TYPE: PRT
<213> ORGANISM: Artificial Sequence
<220> FEATURE:
<223> OTHER INFORMATION: Recombinant antibody fragment

<400> SEQUENCE: 17

Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Ser His
            20                  25                  30

Gly Met Gly Trp Val Arg Gln Ala Pro Gly Lys Gly Leu Glu Trp Val
        35                  40                  45

Ala Ser Ile Ser Thr Gly Arg Tyr Thr Phe Tyr Ala Pro Ala Val Lys
    50                  55                  60

Gly Arg Ala Thr Ile Ser Arg Asp Asn Gly Gln Ser Thr Val Arg Leu
65                  70                  75                  80

Gln Leu Asn Asn Leu Arg Ala Glu Asp Thr Ala Thr Tyr Tyr Cys Thr
                85                  90                  95

Lys Cys Ala Gly Leu Asn Gly Cys Gly Gly Glu Ile Asp Ala Trp
            100                 105                 110

Gly His Gly Thr Glu Val Ile Val Ser Ser
        115                 120

<210> SEQ ID NO 18
<211> LENGTH: 9
<212> TYPE: PRT
<213> ORGANISM: Artificial Sequence
<220> FEATURE:
<223> OTHER INFORMATION: Recombinant antibody fragment

<400> SEQUENCE: 18

Cys Ser Gly Ser Ser Asn Ser Tyr Gly
1               5

<210> SEQ ID NO 19
<211> LENGTH: 8
<212> TYPE: PRT
<213> ORGANISM: Artificial Sequence
<220> FEATURE:

<223> OTHER INFORMATION: Recombinant antibody fragment

<400> SEQUENCE: 19

Ile Tyr Tyr Asn Asp Lys Arg Pro
1               5

<210> SEQ ID NO 20
<211> LENGTH: 12
<212> TYPE: PRT
<213> ORGANISM: Artificial Sequence
<220> FEATURE:
<223> OTHER INFORMATION: Recombinant antibody fragment

<400> SEQUENCE: 20

Cys Gly Ser Tyr Asp Ser Thr Tyr Val Gly Ile Phe
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Recombinant antibody fragment

<400> SEQUENCE: 21

Gly Phe Thr Phe Ser Ser Asn Ala Met Gly Trp Val
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Recombinant antibody fragment

<400> SEQUENCE: 22

Val Ala Gly Ile Ser Ser Asp Gly Arg Tyr Thr Lys Tyr Gly
1               5                   10

<210> SEQ ID NO 23
<211> LENGTH: 19
<212> TYPE: PRT
<213> ORGANISM: Artificial Sequence
<220> FEATURE:
<223> OTHER INFORMATION: Recombinant antibody fragment

<400> SEQUENCE: 23

Cys Ala Lys Ala Phe Gly Asn Asn Tyr Arg Arg Ile Tyr Ala Gly Gln
1               5                   10                  15

Ile Asp Ala

<210> SEQ ID NO 24
<211> LENGTH: 10
<212> TYPE: PRT
<213> ORGANISM: Artificial Sequence
<220> FEATURE:
<223> OTHER INFORMATION: Recombinant antibody fragment

<400> SEQUENCE: 24

Cys Ser Gly Gly Gly Ser Tyr Gly Tyr Gly
1               5                   10

<210> SEQ ID NO 25
<211> LENGTH: 8
<212> TYPE: PRT
<213> ORGANISM: Artificial Sequence

```
<220> FEATURE:
<223> OTHER INFORMATION: Recombinant antibody fragment

<400> SEQUENCE: 25

Ile Tyr Ser Asn Asp Gln Arg Pro
1               5

<210> SEQ ID NO 26
<211> LENGTH: 12
<212> TYPE: PRT
<213> ORGANISM: Artificial Sequence
<220> FEATURE:
<223> OTHER INFORMATION: Recombinant antibody fragment

<400> SEQUENCE: 26

Cys Gly Ser Thr Asp Ser Asp Tyr Val Gly Ile Phe
1               5                   10

<210> SEQ ID NO 27
<211> LENGTH: 12
<212> TYPE: PRT
<213> ORGANISM: Artificial Sequence
<220> FEATURE:
<223> OTHER INFORMATION: r

<400> SEQUENCE: 27

Gly Phe Asp Phe Ser Ser Tyr Ala Thr Ile Trp Val
1               5                   10

<210> SEQ ID NO 28
<211> LENGTH: 16
<212> TYPE: PRT
<213> ORGANISM: Artificial Sequence
<220> FEATURE:
<223> OTHER INFORMATION: Recombinant antibody fragment

<400> SEQUENCE: 28

Val Ala Gly Ile Ser Gly Thr Gly Thr Gly Ser Ser Thr Gly Tyr Ala
1               5                   10                  15

<210> SEQ ID NO 29
<211> LENGTH: 19
<212> TYPE: PRT
<213> ORGANISM: Artificial Sequence
<220> FEATURE:
<223> OTHER INFORMATION: Recombinant antibody fragment

<400> SEQUENCE: 29

Cys Ala Lys Ser Thr Gly Tyr Gly Asp Ser Trp Ile Tyr Pro Asp Ser
1               5                   10                  15

Ile Asp Ala

<210> SEQ ID NO 30
<211> LENGTH: 9
<212> TYPE: PRT
<213> ORGANISM: Artificial Sequence
<220> FEATURE:
<223> OTHER INFORMATION: Recombinant antibody fragment

<400> SEQUENCE: 30

Cys Ser Gly Ser Ser Ser Gly Tyr Gly
1               5

<210> SEQ ID NO 31
<211> LENGTH: 8
<212> TYPE: PRT
```

```
<213> ORGANISM: Artificial Sequence
<220> FEATURE:
<223> OTHER INFORMATION: Recombinant antibody fragment

<400> SEQUENCE: 31

Ile Tyr Asn Ser Asn Lys Arg Pro
1               5

<210> SEQ ID NO 32
<211> LENGTH: 13
<212> TYPE: PRT
<213> ORGANISM: Artificial Sequence
<220> FEATURE:
<223> OTHER INFORMATION: Recombinant antibody fragment

<400> SEQUENCE: 32

Cys Gly Asn Arg Asp Ser Thr Asn Ser Ala Gly Ile Phe
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Recombinant antibody fragment

<400> SEQUENCE: 33

Gly Phe Thr Phe Ser Asp Tyr Gly Met Gly Trp Val
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Recombinant antibody fragment

<400> SEQUENCE: 34

Val Ala Ala Ile Thr Ser Ser Gly Arg Tyr Thr Tyr Tyr Gly
1               5                   10

<210> SEQ ID NO 35
<211> LENGTH: 18
<212> TYPE: PRT
<213> ORGANISM: Artificial Sequence
<220> FEATURE:
<223> OTHER INFORMATION: Recombinant antibody fragment

<400> SEQUENCE: 35

Cys Ala Lys Thr Thr Ser Thr Cys Ala Ser Cys Val Ala Tyr Ser Ile
1               5                   10                  15

Asp Ala

<210> SEQ ID NO 36
<211> LENGTH: 9
<212> TYPE: PRT
<213> ORGANISM: Artificial Sequence
<220> FEATURE:
<223> OTHER INFORMATION: r

<400> SEQUENCE: 36

Cys Ser Gly Gly Gly Ser Tyr Tyr Gly
1               5

<210> SEQ ID NO 37
<211> LENGTH: 8
```

```
<212> TYPE: PRT
<213> ORGANISM: Artificial Sequence
<220> FEATURE:
<223> OTHER INFORMATION: Recombinant antibody fragment

<400> SEQUENCE: 37

Ile Tyr Tyr Asn Asp Lys Arg Pro
1               5

<210> SEQ ID NO 38
<211> LENGTH: 12
<212> TYPE: PRT
<213> ORGANISM: Artificial Sequence
<220> FEATURE:
<223> OTHER INFORMATION: Recombinant antibody fragment

<400> SEQUENCE: 38

Cys Gly Ser Trp Asp Ser Ser Thr Asn Thr Ala Phe
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Recombinant antibody fragment

<400> SEQUENCE: 39

Gly Phe Thr Phe Ser Ser His Gly Met Gly Trp Val
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Recombinant antibody fragment

<400> SEQUENCE: 40

Val Ala Ser Ile Ser Thr Gly Arg Tyr Thr Phe Tyr Ala
1               5                   10

<210> SEQ ID NO 41
<211> LENGTH: 17
<212> TYPE: PRT
<213> ORGANISM: Artificial Sequence
<220> FEATURE:
<223> OTHER INFORMATION: Recombinant antibody fragment

<400> SEQUENCE: 41

Cys Thr Lys Cys Ala Gly Leu Asn Gly Cys Gly Gly Gly Glu Ile Asp
1               5                   10                  15

Ala

<210> SEQ ID NO 42
<211> LENGTH: 9
<212> TYPE: PRT
<213> ORGANISM: Artificial Sequence
<220> FEATURE:
<223> OTHER INFORMATION: Recombinant antibody fragment

<400> SEQUENCE: 42

Cys Ser Gly Asp Ser Ser Tyr Tyr Gly
1               5

<210> SEQ ID NO 43
```

```
<211> LENGTH: 8
<212> TYPE: PRT
<213> ORGANISM: Artificial Sequence
<220> FEATURE:
<223> OTHER INFORMATION: Recombinant antibody fragment

<400> SEQUENCE: 43

Ile Tyr Ala Asn Thr Asn Arg Pro
1               5

<210> SEQ ID NO 44
<211> LENGTH: 12
<212> TYPE: PRT
<213> ORGANISM: Artificial Sequence
<220> FEATURE:
<223> OTHER INFORMATION: Recombinant antibody fragment

<400> SEQUENCE: 44

Cys Gly Ser Ala Asp Ser Thr Tyr Ala Gly Ile Phe
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Recombinant antibody fragment

<400> SEQUENCE: 45

Gly Phe Thr Phe Ser Ser Tyr Thr Met Asn Trp Val
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Recombinant antibody fragment

<400> SEQUENCE: 46

Val Gly Val Ile Ser Asn Ser Gly Arg Thr Thr Asn Tyr Gly
1               5                   10

<210> SEQ ID NO 47
<211> LENGTH: 27
<212> TYPE: PRT
<213> ORGANISM: Artificial Sequence
<220> FEATURE:
<223> OTHER INFORMATION: Recombinant antibody fragment

<400> SEQUENCE: 47

Cys Ala Lys Ser Ser Ala Ser Ala Ser Cys Ala Trp Trp Ala Gly Arg
1               5                   10                  15

Ser Tyr Pro Cys Ser Ala Asn Arg Ile Asp Ala
            20                  25

<210> SEQ ID NO 48
<211> LENGTH: 8
<212> TYPE: PRT
<213> ORGANISM: Artificial Sequence
<220> FEATURE:
<223> OTHER INFORMATION: Recombinant antibody fragment

<400> SEQUENCE: 48

Cys Ser Gly Gly Gly Ser Tyr Gly
1               5
```

```
<210> SEQ ID NO 49
<211> LENGTH: 8
<212> TYPE: PRT
<213> ORGANISM: Artificial Sequence
<220> FEATURE:
<223> OTHER INFORMATION: Recombinant antibody fragment

<400> SEQUENCE: 49

Ile Tyr Gly Asn Asp Lys Arg Pro
1               5

<210> SEQ ID NO 50
<211> LENGTH: 9
<212> TYPE: PRT
<213> ORGANISM: Artificial Sequence
<220> FEATURE:
<223> OTHER INFORMATION: Recombinant antibody fragment

<400> SEQUENCE: 50

Cys Gly Ser Tyr Glu Asp Ser Ser Ala
1               5

<210> SEQ ID NO 51
<211> LENGTH: 12
<212> TYPE: PRT
<213> ORGANISM: Artificial Sequence
<220> FEATURE:
<223> OTHER INFORMATION: Recombinant antibody fragment

<400> SEQUENCE: 51

Gly Phe Thr Phe Ser Ser His Gly Met Gly Trp Val
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Recombinant antibody fragment

<400> SEQUENCE: 52

Val Ala Ser Ile Ser Thr Gly Arg Tyr Thr Phe Tyr Ala
1               5                   10

<210> SEQ ID NO 53
<211> LENGTH: 17
<212> TYPE: PRT
<213> ORGANISM: Artificial Sequence
<220> FEATURE:
<223> OTHER INFORMATION: Recombinant antibody fragment

<400> SEQUENCE: 53

Cys Thr Lys Cys Ala Gly Leu Asn Gly Cys Gly Gly Gly Glu Ile Asp
1               5                   10                  15

Ala

<210> SEQ ID NO 54
<211> LENGTH: 11
<212> TYPE: PRT
<213> ORGANISM: Artificial Sequence
<220> FEATURE:
<223> OTHER INFORMATION: Recombinant antibody fragment

<400> SEQUENCE: 54

Cys Ser Gly Gly Tyr Ser Gly Cys Gly Tyr Gly
1               5                   10
```

<210> SEQ ID NO 55
<211> LENGTH: 8
<212> TYPE: PRT
<213> ORGANISM: Artificial Sequence
<220> FEATURE:
<223> OTHER INFORMATION: Recombinant antibody fragment

<400> SEQUENCE: 55

Ile Tyr Asp Asn Thr Asn Arg Pro
1               5

<210> SEQ ID NO 56
<211> LENGTH: 14
<212> TYPE: PRT
<213> ORGANISM: Artificial Sequence
<220> FEATURE:
<223> OTHER INFORMATION: Recombinant antibody fragment

<400> SEQUENCE: 56

Cys Gly Ser Ala Asp Ser Ile Ser Tyr Asn Asp Tyr Val Gly
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Recombinant antibody fragment

<400> SEQUENCE: 57

Gly Phe Ser Phe Ser Gly Tyr Gly Met Gly Trp Val
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Recombinant antibody fragment

<400> SEQUENCE: 58

Val Ala Gly Ile Asp Tyr Ser Gly Gly Thr Glu Tyr Gly
1               5                   10

<210> SEQ ID NO 59
<211> LENGTH: 17
<212> TYPE: PRT
<213> ORGANISM: Artificial Sequence
<220> FEATURE:
<223> OTHER INFORMATION: Recombinant antibody fragment

<400> SEQUENCE: 59

Cys Thr Lys Cys Ala Tyr Ser Ser Gly Trp Cys Gly Asp Ser Ile Asp
1               5                   10                  15

Ala

<210> SEQ ID NO 60
<211> LENGTH: 9
<212> TYPE: PRT
<213> ORGANISM: Artificial Sequence
<220> FEATURE:
<223> OTHER INFORMATION: Recombinant antibody fragment

<400> SEQUENCE: 60

Cys Ser Gly Ser Ser Gly Ser Tyr Gly

```
1               5

<210> SEQ ID NO 61
<211> LENGTH: 8
<212> TYPE: PRT
<213> ORGANISM: Artificial Sequence
<220> FEATURE:
<223> OTHER INFORMATION: Recombinant antibody fragment

<400> SEQUENCE: 61

Ile Tyr Arg Asn Asp Lys Arg Pro
1               5

<210> SEQ ID NO 62
<211> LENGTH: 13
<212> TYPE: PRT
<213> ORGANISM: Artificial Sequence
<220> FEATURE:
<223> OTHER INFORMATION: Recombinant antibody fragment

<400> SEQUENCE: 62

Cys Gly Gly Tyr Asp Ser Ser Ala Gly Tyr Ala Ala Phe
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Recombinant antibody fragment

<400> SEQUENCE: 63

Gly Phe Thr Phe Ser Ser His Gly Met Gly Trp Val
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Recombinant antibody fragment

<400> SEQUENCE: 64

Val Gly Ser Ile Ser Thr Gly Arg Tyr Thr Phe Tyr Ala
1               5                   10

<210> SEQ ID NO 65
<211> LENGTH: 17
<212> TYPE: PRT
<213> ORGANISM: Artificial Sequence
<220> FEATURE:
<223> OTHER INFORMATION: Recombinant antibody fragment

<400> SEQUENCE: 65

Cys Thr Lys Cys Ala Gly Leu Asn Gly Cys Gly Gly Gly Glu Ile Asp
1               5                   10                  15

Ala

<210> SEQ ID NO 66
<211> LENGTH: 9
<212> TYPE: PRT
<213> ORGANISM: Artificial Sequence
<220> FEATURE:
<223> OTHER INFORMATION: Recombinant antibody fragment

<400> SEQUENCE: 66
```

Cys Ser Gly Gly Gly Ser Trp Tyr Gly
1               5

<210> SEQ ID NO 67
<211> LENGTH: 8
<212> TYPE: PRT
<213> ORGANISM: Artificial Sequence
<220> FEATURE:
<223> OTHER INFORMATION: Recombinant antibody fragment

<400> SEQUENCE: 67

Ile Tyr Ser Asn Asn Lys Arg Pro
1               5

<210> SEQ ID NO 68
<211> LENGTH: 13
<212> TYPE: PRT
<213> ORGANISM: Artificial Sequence
<220> FEATURE:
<223> OTHER INFORMATION: Recombinant antibody fragment

<400> SEQUENCE: 68

Cys Gly Ser Arg Asp Ser Ser Thr Tyr Val Gly Ile Phe
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Recombinant antibody fragment

<400> SEQUENCE: 69

Gly Phe Thr Phe Ser Ser Tyr Thr Met Gln Trp Val
1               5                   10

<210> SEQ ID NO 70
<211> LENGTH: 14
<212> TYPE: PRT
<213> ORGANISM: Artificial Sequence
<220> FEATURE:
<223> OTHER INFORMATION: Recombinant antibody fragment

<400> SEQUENCE: 70

Val Ala Ala Ile Thr Ser Ser Gly Arg Tyr Thr Gly Tyr Gly
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Recombinant antibody fragment

<400> SEQUENCE: 71

Cys Ala Arg Gly Gly Ser Val Asp Lys Ile Asp Ala
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Recombinant antibody fragment

<400> SEQUENCE: 72

Cys Ser Gly Ser Ser Ser Gly Ser Tyr Gly

<210> SEQ ID NO 73
<211> LENGTH: 8
<212> TYPE: PRT
<213> ORGANISM: Artificial Sequence
<220> FEATURE:
<223> OTHER INFORMATION: Recombinant antibody fragment

<400> SEQUENCE: 73

Ile Tyr Tyr Asn Asp Lys Arg Pro
1               5

<210> SEQ ID NO 74
<211> LENGTH: 14
<212> TYPE: PRT
<213> ORGANISM: Artificial Sequence
<220> FEATURE:
<223> OTHER INFORMATION: Recombinant antibody fragment

<400> SEQUENCE: 74

Cys Gly Ser Tyr Asp Ser Ser Ala Gly Tyr Val Gly Ile Phe
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Recombinant antibody fragment

<400> SEQUENCE: 75

Gly Phe Thr Phe Ser Ser Tyr Thr Met Gln Trp Val
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Recombinant antibody fragment

<400> SEQUENCE: 76

Val Ala Gly Ile Gly Ser Ser Ser Tyr Thr Tyr Phe Gly
1               5                   10

<210> SEQ ID NO 77
<211> LENGTH: 20
<212> TYPE: PRT
<213> ORGANISM: Artificial Sequence
<220> FEATURE:
<223> OTHER INFORMATION: Recombinant antibody fragment

<400> SEQUENCE: 77

Cys Ala Lys Gly Ala Ser Ala Thr Trp Ser Tyr Ala Tyr Ile Ala Ser
1               5                   10                  15

Arg Ile Gly Ala
            20

<210> SEQ ID NO 78
<211> LENGTH: 9
<212> TYPE: PRT
<213> ORGANISM: Artificial Sequence
<220> FEATURE:
<223> OTHER INFORMATION: Recombinant antibody fragment

<400> SEQUENCE: 78

```
Cys Ser Gly Ser Gly Ser Trp Tyr Gly
1               5

<210> SEQ ID NO 79
<211> LENGTH: 8
<212> TYPE: PRT
<213> ORGANISM: Artificial Sequence
<220> FEATURE:
<223> OTHER INFORMATION: Recombinant antibody fragment

<400> SEQUENCE: 79

Ile Tyr Ser Asn Asp Lys Arg Pro
1               5

<210> SEQ ID NO 80
<211> LENGTH: 7
<212> TYPE: PRT
<213> ORGANISM: Artificial Sequence
<220> FEATURE:
<223> OTHER INFORMATION: Recombinant antibody fragment

<400> SEQUENCE: 80

Cys Gly Asn Trp Asp Ile Phe
1               5

<210> SEQ ID NO 81
<211> LENGTH: 12
<212> TYPE: PRT
<213> ORGANISM: Artificial Sequence
<220> FEATURE:
<223> OTHER INFORMATION: Recombinant antibody fragment

<400> SEQUENCE: 81

Gly Phe Thr Phe Ser Ser His Gly Met Gly Trp Val
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Recombinant antibody fragment

<400> SEQUENCE: 82

Val Ala Ser Ile Ser Thr Gly Arg Tyr Thr Phe Tyr Ala
1               5                   10

<210> SEQ ID NO 83
<211> LENGTH: 17
<212> TYPE: PRT
<213> ORGANISM: Artificial Sequence
<220> FEATURE:
<223> OTHER INFORMATION: Recombinant antibody fragment

<400> SEQUENCE: 83

Cys Thr Lys Cys Ala Gly Leu Asn Gly Cys Gly Gly Glu Ile Asp
1               5                   10                  15
Ala

<210> SEQ ID NO 84
<211> LENGTH: 9
<212> TYPE: PRT
<213> ORGANISM: Artificial Sequence
<220> FEATURE:
<223> OTHER INFORMATION: Recombinant antibody fragment
```

```
<400> SEQUENCE: 84

Cys Ser Gly Gly Ser Asn Asn Tyr Gly
1               5

<210> SEQ ID NO 85
<211> LENGTH: 8
<212> TYPE: PRT
<213> ORGANISM: Artificial Sequence
<220> FEATURE:
<223> OTHER INFORMATION: r

<400> SEQUENCE: 85

Ile Tyr Arg Asn Asp Lys Arg Pro
1               5

<210> SEQ ID NO 86
<211> LENGTH: 13
<212> TYPE: PRT
<213> ORGANISM: Artificial Sequence
<220> FEATURE:
<223> OTHER INFORMATION: Recombinant antibody fragment

<400> SEQUENCE: 86

Cys Gly Gly Tyr Asp Ser Ser Asn Tyr Val Ala Val Phe
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Recombinant antibody fragment

<400> SEQUENCE: 87

Gly Phe Thr Phe Ser Ser His Gly Met Gly Trp Val
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Recombinant antibody fragment

<400> SEQUENCE: 88

Val Ala Ser Ile Ser Thr Gly Arg Tyr Thr Phe Tyr Ala
1               5                   10

<210> SEQ ID NO 89
<211> LENGTH: 17
<212> TYPE: PRT
<213> ORGANISM: Artificial Sequence
<220> FEATURE:
<223> OTHER INFORMATION: Recombinant antibody fragment

<400> SEQUENCE: 89

Cys Thr Lys Cys Ala Gly Leu Asn Gly Cys Gly Gly Glu Ile Asp
1               5                   10                  15

Ala

<210> SEQ ID NO 90
<211> LENGTH: 10
<212> TYPE: PRT
<213> ORGANISM: Artificial Sequence
<220> FEATURE:
<223> OTHER INFORMATION: Recombinant antibody fragment
```

```
<400> SEQUENCE: 90

Cys Ser Gly Ser Ser Gly Ser Ser Tyr Gly
1               5                   10

<210> SEQ ID NO 91
<211> LENGTH: 8
<212> TYPE: PRT
<213> ORGANISM: Artificial Sequence
<220> FEATURE:
<223> OTHER INFORMATION: Recombinant antibody fragment

<400> SEQUENCE: 91

Ile Tyr Arg Asn Thr Gln Arg Pro
1               5

<210> SEQ ID NO 92
<211> LENGTH: 11
<212> TYPE: PRT
<213> ORGANISM: Artificial Sequence
<220> FEATURE:
<223> OTHER INFORMATION: Recombinant antibody fragment

<400> SEQUENCE: 92

Cys Gly Ala Val Asp Ser Thr Gly Gly Ala Phe
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Recombinant antibody fragment

<400> SEQUENCE: 93

Gly Phe Thr Phe Asn Asp Tyr Gly Met Ala Trp Val
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Recombinant antibody fragment

<400> SEQUENCE: 94

Val Ala Ser Ile Ser Thr Gly Arg Tyr Thr Phe Tyr Ala
1               5                   10

<210> SEQ ID NO 95
<211> LENGTH: 17
<212> TYPE: PRT
<213> ORGANISM: Artificial Sequence
<220> FEATURE:
<223> OTHER INFORMATION: Recombinant antibody fragment

<400> SEQUENCE: 95

Cys Thr Lys Cys Ala Gly Leu Asn Gly Cys Gly Gly Gly Glu Ile Asp
1               5                   10                  15

Ala

<210> SEQ ID NO 96
<211> LENGTH: 9
<212> TYPE: PRT
<213> ORGANISM: Artificial Sequence
<220> FEATURE:
```

```
<223> OTHER INFORMATION: Recombinant antibody fragment

<400> SEQUENCE: 96

Cys Ser Gly Gly Ser Asn Asn Tyr Gly
1               5

<210> SEQ ID NO 97
<211> LENGTH: 8
<212> TYPE: PRT
<213> ORGANISM: Artificial Sequence
<220> FEATURE:
<223> OTHER INFORMATION: Recombinant antibody fragment

<400> SEQUENCE: 97

Ile Tyr Ala Asn Thr Lys Arg Pro
1               5

<210> SEQ ID NO 98
<211> LENGTH: 11
<212> TYPE: PRT
<213> ORGANISM: Artificial Sequence
<220> FEATURE:
<223> OTHER INFORMATION: Recombinant antibody fragment

<400> SEQUENCE: 98

Cys Gly Ser Ala Asp Ser Arg Ala Gly Ile Phe
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Recombinant antibody fragment

<400> SEQUENCE: 99

Gly Phe Thr Phe Ser Ser His Gly Met Gly Trp Val
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Recombinant antibody fragment

<400> SEQUENCE: 100

Val Ala Ser Ile Ser Thr Gly Arg Tyr Thr Phe Tyr Ala
1               5                   10

<210> SEQ ID NO 101
<211> LENGTH: 17
<212> TYPE: PRT
<213> ORGANISM: Artificial Sequence
<220> FEATURE:
<223> OTHER INFORMATION: Recombinant antibody fragment

<400> SEQUENCE: 101

Cys Thr Lys Cys Ala Gly Leu Asn Gly Cys Gly Gly Gly Glu Ile Asp
1               5                   10                  15

Val

<210> SEQ ID NO 102
<211> LENGTH: 106
<212> TYPE: PRT
<213> ORGANISM: Artificial Sequence
```

```
<220> FEATURE:
<223> OTHER INFORMATION: Recombinant antibody fragment

<400> SEQUENCE: 102

Ala Leu Thr Gln Pro Ser Ser Val Ser Ala Asn Pro Gly Glu Thr Val
1               5                   10                  15

Lys Ile Thr Cys Ser Gly Ser Ser Gly Tyr Gly Tyr Gly Trp Tyr
            20                  25                  30

Gln Gln Lys Ser Pro Gly Ser Ala Pro Val Thr Val Ile Tyr Asn Ser
        35                  40                  45

Asn Lys Arg Pro Ser Asp Ile Pro Ser Arg Phe Ser Gly Ser Lys Ser
50                  55                  60

Gly Ser Thr Gly Thr Leu Thr Ile Thr Gly Val Gln Ala Glu Asp Glu
65                  70                  75                  80

Ala Val Tyr Phe Cys Gly Asn Arg Asp Ser Thr Asn Ser Ala Gly Ile
                85                  90                  95

Phe Gly Ala Gly Thr Thr Leu Thr Val Leu
            100                 105

<210> SEQ ID NO 103
<211> LENGTH: 124
<212> TYPE: PRT
<213> ORGANISM: Artificial Sequence
<220> FEATURE:
<223> OTHER INFORMATION: Recombinant antibody fragment

<400> SEQUENCE: 103

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Asp Tyr
            20                  25                  30

Gly Met Gly Trp Val Arg Gln Ala Pro Gly Lys Gly Leu Glu Phe Val
        35                  40                  45

Ala Ala Ile Thr Ser Ser Gly Arg Tyr Thr Tyr Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Phe Cys
                85                  90                  95

Ala Lys Thr Thr Ser Thr Cys Ala Ser Cys Val Ala Tyr Ser Ile Asp
            100                 105                 110

Ala Trp Gly His Gly Thr Glu Val Ile Val Ser Ser
        115                 120

<210> SEQ ID NO 104
<211> LENGTH: 103
<212> TYPE: PRT
<213> ORGANISM: Artificial Sequence
<220> FEATURE:
<223> OTHER INFORMATION: Recombinant antibody fragment

<400> SEQUENCE: 104

Ala Leu Thr Gln Pro Ser Ser Val Ser Ala Asn Pro Gly Glu Thr Val
1               5                   10                  15

Lys Ile Thr Cys Ser Gly Gly Gly Ser Tyr Tyr Gly Trp Phe Gln Gln
            20                  25                  30

Lys Ser Pro Gly Ser Ala Pro Val Thr Val Ile Tyr Tyr Asn Asp Lys
        35                  40                  45
```

```
Arg Pro Ser Asn Ile Pro Ser Arg Phe Ser Gly Ser Lys Ser Gly Ser
    50                  55                  60

Thr Ala Thr Leu Thr Ile Thr Gly Val Gln Ala Glu Asp Glu Ala Val
65                  70                  75                  80

Tyr Tyr Cys Gly Ser Trp Asp Ser Ser Thr Asn Thr Ala Phe Gly Ala
                85                  90                  95

Gly Thr Thr Leu Thr Val Leu
                100

<210> SEQ ID NO 105
<211> LENGTH: 122
<212> TYPE: PRT
<213> ORGANISM: Artificial Sequence
<220> FEATURE:
<223> OTHER INFORMATION: Recombinant antibody fragment

<400> SEQUENCE: 105

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser His
                20                  25                  30

Gly Met Gly Trp Val Arg Gln Ala Pro Gly Lys Gly Leu Glu Trp Val
            35                  40                  45

Ala Ser Ile Ser Thr Gly Arg Tyr Thr Phe Tyr Ala Pro Ala Val Lys
        50                  55                  60

Gly Arg Ala Thr Ile Ser Arg Asp Asn Gly Gln Ser Thr Val Arg Leu
65                  70                  75                  80

Gln Leu Asn Asn Leu Arg Ala Glu Asp Thr Ala Thr Tyr Tyr Cys Thr
                85                  90                  95

Lys Cys Ala Gly Leu Asn Gly Cys Gly Gly Glu Ile Asp Ala Trp
            100                 105                 110

Gly His Gly Thr Glu Val Ile Val Ser Ser
        115                 120

<210> SEQ ID NO 106
<211> LENGTH: 105
<212> TYPE: PRT
<213> ORGANISM: Artificial Sequence
<220> FEATURE:
<223> OTHER INFORMATION: Recombinant antibody fragment

<400> SEQUENCE: 106

Ala Leu Thr Gln Pro Ser Ser Val Ser Ala Asn Leu Gly Glu Thr Val
1               5                   10                  15

Lys Ile Thr Cys Ser Gly Gly Gly Ser Tyr Gly Trp Tyr Gln Gln Lys
                20                  25                  30

Ser Pro Gly Ser Ala Pro Val Thr Leu Ile Tyr Gly Asn Asp Lys Arg
            35                  40                  45

Pro Ser Asn Ile Pro Ser Arg Phe Ser Gly Ser Lys Ser Gly Ser Thr
        50                  55                  60

His Thr Leu Thr Ile Thr Gly Val Gln Ala Asp Asp Glu Ala Val Tyr
65                  70                  75                  80

Phe Cys Gly Ser Tyr Glu Asp Ser Ser Ala Gly Tyr Val Gly Ile Phe
                85                  90                  95

Gly Ala Gly Thr Thr Leu Thr Val Leu
            100                 105

<210> SEQ ID NO 107
```

<211> LENGTH: 122
<212> TYPE: PRT
<213> ORGANISM: Artificial Sequence
<220> FEATURE:
<223> OTHER INFORMATION: Recombinant antibody fragment

<400> SEQUENCE: 107

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser His
            20                  25                  30

Gly Met Gly Trp Val Arg Gln Ala Pro Gly Lys Gly Leu Glu Trp Val
        35                  40                  45

Ala Ser Ile Ser Thr Gly Arg Tyr Thr Phe Tyr Ala Pro Ala Val Lys
    50                  55                  60

Gly Arg Ala Thr Ile Ser Arg Asp Asn Gly Gln Ser Thr Val Arg Leu
65                  70                  75                  80

Gln Leu Asn Asn Leu Arg Ala Glu Asp Thr Ala Thr Tyr Tyr Cys Thr
                85                  90                  95

Lys Cys Ala Gly Leu Asn Gly Cys Gly Gly Glu Ile Asp Ala Trp
            100                 105                 110

Gly His Gly Thr Glu Val Ile Val Ser Ser
        115                 120

<210> SEQ ID NO 108
<211> LENGTH: 109
<212> TYPE: PRT
<213> ORGANISM: Artificial Sequence
<220> FEATURE:
<223> OTHER INFORMATION: Recombinant antibody fragment

<400> SEQUENCE: 108

Ala Leu Thr Gln Pro Ser Ser Val Ser Ala Asn Pro Gly Glu Thr Val
1               5                   10                  15

Glu Ile Thr Cys Ser Gly Gly Tyr Ser Gly Cys Gly Tyr Gly Trp Tyr
            20                  25                  30

Gln Gln Lys Ser Pro Gly Ser Ala Pro Val Thr Val Ile Tyr Asp Asn
        35                  40                  45

Thr Asn Arg Pro Ser Asn Ile Pro Ser Arg Phe Ser Gly Ser Thr Ser
    50                  55                  60

Gly Ser Thr Ala Thr Leu Thr Ile Thr Gly Val Gln Ala Glu Asp Glu
65                  70                  75                  80

Ala Val Tyr Tyr Cys Gly Ser Ala Asp Ser Ile Ser Tyr Asn Asp Tyr
                85                  90                  95

Val Gly Ile Phe Gly Ala Gly Thr Thr Leu Thr Val Leu
            100                 105

<210> SEQ ID NO 109
<211> LENGTH: 123
<212> TYPE: PRT
<213> ORGANISM: Artificial Sequence
<220> FEATURE:
<223> OTHER INFORMATION: Recombinant antibody fragment

<400> SEQUENCE: 109

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Ser Phe Ser Gly Tyr
            20                  25                  30

```
Gly Met Gly Trp Val Arg Gln Ala Pro Gly Lys Gly Leu Glu Trp Val
        35                  40                  45

Ala Gly Ile Asp Tyr Ser Gly Gly Thr Glu Tyr Gly Pro Ala Val
 50                  55                  60

Gln Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Ala Ile Tyr Phe Cys
                 85                  90                  95

Thr Lys Cys Ala Tyr Ser Ser Gly Trp Cys Gly Asp Ser Ile Asp Ala
             100                 105                 110

Trp Gly His Gly Thr Glu Val Ile Val Ser Ser
         115                 120
```

<210> SEQ ID NO 110
<211> LENGTH: 104
<212> TYPE: PRT
<213> ORGANISM: Artificial Sequence
<220> FEATURE:
<223> OTHER INFORMATION: Recombinant antibody fragment

<400> SEQUENCE: 110

```
Ala Leu Thr Gln Pro Ser Ser Val Ser Ala Asn Pro Gly Glu Thr Val
 1               5                  10                  15

Lys Ile Thr Cys Ser Gly Gly Gly Ser Trp Tyr Gly Trp Phe Gln Gln
                 20                  25                  30

Lys Ser Pro Gly Ser Ala Pro Val Thr Leu Ile Tyr Ser Asn Asn Lys
             35                  40                  45

Arg Pro Ser Asn Ile Pro Ser Arg Phe Ser Gly Ser Thr Ser Gly Ser
 50                  55                  60

Thr Ser Thr Leu Thr Ile Thr Gly Val Gln Ala Asp Asp Glu Ala Val
 65                  70                  75                  80

Tyr Phe Cys Gly Ser Arg Asp Ser Ser Thr Tyr Val Gly Ile Phe Gly
                 85                  90                  95

Ala Gly Thr Thr Leu Thr Val Leu
             100
```

<210> SEQ ID NO 111
<211> LENGTH: 118
<212> TYPE: PRT
<213> ORGANISM: Artificial Sequence
<220> FEATURE:
<223> OTHER INFORMATION: Recombinant antibody fragment

<400> SEQUENCE: 111

```
Ala Val Thr Leu Asp Glu Ser Gly Gly Gly Leu Gln Thr Pro Gly Gly
 1               5                  10                  15

Ala Leu Ser Leu Val Cys Lys Ala Ser Gly Phe Thr Phe Ser Ser Tyr
                 20                  25                  30

Thr Met Gln Trp Val Arg Gln Ala Pro Gly Lys Gly Leu Glu Phe Val
             35                  40                  45

Ala Ala Ile Thr Ser Ser Gly Arg Tyr Thr Gly Tyr Gly Ser Ala Val
 50                  55                  60

Lys Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Ala Ile Tyr Tyr Cys
                 85                  90                  95

Ala Arg Gly Gly Ser Val Asp Lys Ile Asp Ala Trp Gly His Gly Thr
             100                 105                 110
```

Glu Val Ile Val Ser Ser
        115

<210> SEQ ID NO 112
<211> LENGTH: 106
<212> TYPE: PRT
<213> ORGANISM: Artificial Sequence
<220> FEATURE:
<223> OTHER INFORMATION: Recombinant antibody fragment

<400> SEQUENCE: 112

Ala Leu Thr Gln Pro Ser Ser Val Ser Ala Asn Leu Gly Gly Thr Val
1               5                   10                  15

Lys Ile Thr Cys Ser Gly Ser Ser Gly Ser Tyr Gly Trp Tyr Gln
            20                  25                  30

Gln Lys Ser Pro Gly Ser Ala Pro Val Thr Val Ile Tyr Tyr Asn Asp
        35                  40                  45

Lys Arg Pro Ser Asp Ile Pro Ser Arg Phe Ser Gly Ser Lys Ser Gly
    50                  55                  60

Ser Thr Gly Thr Leu Thr Ile Thr Gly Val Gln Val Glu Asp Glu Ala
65                  70                  75                  80

Val Tyr Tyr Cys Gly Ser Tyr Asp Ser Ser Ala Gly Tyr Val Gly Ile
                85                  90                  95

Phe Gly Ala Gly Thr Thr Leu Thr Val Leu
            100                 105

<210> SEQ ID NO 113
<211> LENGTH: 125
<212> TYPE: PRT
<213> ORGANISM: Artificial Sequence
<220> FEATURE:
<223> OTHER INFORMATION: Recombinant antibody fragment

<400> SEQUENCE: 113

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Thr Met Gln Trp Val Arg Gln Ala Pro Gly Lys Gly Leu Glu Trp Val
        35                  40                  45

Ala Gly Ile Gly Ser Ser Ser Tyr Thr Tyr Phe Gly Pro Ala Val Lys
    50                  55                  60

Gly Arg Ala Thr Ile Ser Arg Asp Asn Gly Gln Ser Thr Val Arg Leu
65                  70                  75                  80

Gln Leu Asn Asn Leu Arg Ala Glu Asp Thr Gly Thr Tyr Phe Cys Ala
                85                  90                  95

Lys Gly Ala Ser Ala Thr Trp Ser Tyr Ala Tyr Ile Ala Ser Arg Ile
            100                 105                 110

Gly Ala Trp Gly His Gly Thr Glu Val Ile Val Ser Ser
        115                 120                 125

<210> SEQ ID NO 114
<211> LENGTH: 104
<212> TYPE: PRT
<213> ORGANISM: Artificial Sequence
<220> FEATURE:
<223> OTHER INFORMATION: Recombinant antibody fragment

<400> SEQUENCE: 114

Ala Leu Thr Gln Pro Ser Ser Val Ser Ala Asn Leu Gly Gly Thr Val
1               5                   10                  15

Glu Ile Thr Cys Ser Gly Gly Ser Asn Asn Tyr Gly Trp Tyr Gln Gln
                20                  25                  30

Lys Ser Pro Gly Ser Ala Pro Val Thr Leu Ile Tyr Arg Asn Asp Lys
            35                  40                  45

Arg Pro Ser Asp Ile Pro Ser Arg Phe Ala Gly Ser Thr Ser Gly Ser
50                  55                  60

Ala Asn Thr Leu Thr Ile Thr Gly Val Gln Gly Glu Asp Glu Ala Val
65                  70                  75                  80

Tyr Phe Cys Gly Gly Tyr Asp Ser Ser Asn Tyr Val Ala Val Phe Gly
                85                  90                  95

Ala Gly Thr Thr Leu Thr Val Leu
            100

<210> SEQ ID NO 115
<211> LENGTH: 122
<212> TYPE: PRT
<213> ORGANISM: Artificial Sequence
<220> FEATURE:
<223> OTHER INFORMATION: Recombinant antibody fragment

<400> SEQUENCE: 115

Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Ser His
                20                  25                  30

Gly Met Gly Trp Val Arg Gln Ala Pro Gly Lys Gly Leu Glu Trp Val
            35                  40                  45

Ala Ser Ile Ser Thr Gly Arg Tyr Thr Phe Tyr Ala Pro Ala Val Lys
50                  55                  60

Gly Arg Ala Thr Ile Ser Arg Asp Asn Gly Gln Ser Thr Val Arg Leu
65                  70                  75                  80

Gln Leu Asn Asn Leu Arg Ala Glu Asp Thr Ala Thr Tyr Tyr Cys Thr
                85                  90                  95

Lys Cys Ala Gly Leu Asn Gly Cys Gly Gly Glu Ile Asp Ala Trp
            100                 105                 110

Gly His Gly Thr Glu Val Ile Val Ser Ser
            115                 120

<210> SEQ ID NO 116
<211> LENGTH: 103
<212> TYPE: PRT
<213> ORGANISM: Artificial Sequence
<220> FEATURE:
<223> OTHER INFORMATION: Recombinant antibody fragment

<400> SEQUENCE: 116

Ala Leu Thr Gln Pro Ser Ser Val Ser Ala Asn Pro Gly Glu Thr Val
1               5                   10                  15

Glu Ile Thr Cys Ser Gly Ser Ser Gly Ser Tyr Gly Trp Tyr Gln
                20                  25                  30

Gln Lys Ser Pro Gly Ser Ala Pro Val Thr Val Ile Tyr Arg Asn Thr
            35                  40                  45

Gln Arg Pro Ser Asp Ile Pro Ser Arg Phe Ser Gly Ser Lys Ser Gly
50                  55                  60

Ser Thr Gly Thr Leu Thr Ile Thr Gly Val Gln Val Glu Asp Glu Ala
65                  70                  75                  80

```
Val Tyr Tyr Cys Gly Ala Val Asp Ser Thr Gly Gly Ala Phe Gly Ala
                85                  90                  95

Gly Thr Thr Leu Thr Val Leu
            100
```

<210> SEQ ID NO 117
<211> LENGTH: 122
<212> TYPE: PRT
<213> ORGANISM: Artificial Sequence
<220> FEATURE:
<223> OTHER INFORMATION: Recombinant antibody fragment

<400> SEQUENCE: 117

```
Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Asn Asp Tyr
            20                  25                  30

Gly Met Ala Trp Val Arg Gln Ala Pro Gly Lys Gly Leu Glu Trp Val
        35                  40                  45

Ala Ser Ile Ser Thr Gly Arg Tyr Thr Phe Tyr Ala Pro Ala Val Lys
    50                  55                  60

Gly Arg Ala Thr Ile Ser Arg Asp Asn Gly Gln Ser Thr Val Arg Leu
65                  70                  75                  80

Gln Leu Asn Asn Leu Arg Ala Glu Asp Thr Ala Thr Tyr Tyr Cys Thr
                85                  90                  95

Lys Cys Ala Gly Leu Asn Gly Cys Gly Gly Glu Ile Asp Ala Trp
            100                 105                 110

Gly His Gly Thr Glu Val Ile Val Ser Ser
        115                 120
```

<210> SEQ ID NO 118
<211> LENGTH: 102
<212> TYPE: PRT
<213> ORGANISM: Artificial Sequence
<220> FEATURE:
<223> OTHER INFORMATION: Recombinant antibody fragment

<400> SEQUENCE: 118

```
Ala Leu Thr Gln Pro Ser Ser Val Ser Ala Asn Leu Gly Gly Thr Val
1               5                   10                  15

Glu Ile Thr Cys Ser Gly Gly Ser Asn Asn Tyr Gly Trp Tyr Gln Gln
            20                  25                  30

Lys Ser Pro Gly Ser Ala Pro Val Thr Leu Ile Tyr Ala Asn Thr Lys
        35                  40                  45

Arg Pro Ser Asp Ile Pro Ser Arg Phe Ser Gly Ser Lys Ser Gly Ser
    50                  55                  60

Thr Gly Thr Leu Thr Ile Thr Gly Val Gln Ala Glu Asp Glu Ala Val
65                  70                  75                  80

Tyr Phe Cys Gly Ser Ala Asp Ser Arg Ala Gly Ile Phe Gly Ala Gly
                85                  90                  95

Thr Thr Leu Thr Val Leu
            100
```

<210> SEQ ID NO 119
<211> LENGTH: 122
<212> TYPE: PRT
<213> ORGANISM: Artificial Sequence
<220> FEATURE:
<223> OTHER INFORMATION: Recombinant antibody fragment

<400> SEQUENCE: 119

Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Ser His
            20                  25                  30

Gly Met Gly Trp Val Arg Gln Ala Pro Gly Lys Gly Leu Glu Trp Val
        35                  40                  45

Ala Ser Ile Ser Thr Gly Arg Tyr Thr Phe Tyr Ala Pro Ala Val Lys
    50                  55                  60

Gly Arg Ala Thr Ile Ser Arg Asp Asn Gly Gln Thr Thr Val Arg Leu
65                  70                  75                  80

Gln Leu Asn Asn Leu Arg Ala Glu Asp Thr Gly Ile Tyr Tyr Cys Thr
                85                  90                  95

Lys Cys Ala Gly Leu Asn Gly Cys Gly Gly Glu Ile Asp Val Trp
            100                 105                 110

Gly His Gly Thr Glu Val Ile Val Ser Ser
        115                 120

<210> SEQ ID NO 120
<211> LENGTH: 18
<212> TYPE: PRT
<213> ORGANISM: Artificial Sequence
<220> FEATURE:
<223> OTHER INFORMATION: Recombinant antibody fragment

<400> SEQUENCE: 120

Gly Gln Ser Ser Arg Ser Ser Gly Gly Gly Ser Ser Gly Gly Gly
1               5                   10                  15

Gly Ser

<210> SEQ ID NO 121
<211> LENGTH: 5
<212> TYPE: PRT
<213> ORGANISM: Artificial Sequence
<220> FEATURE:
<223> OTHER INFORMATION: Recombinant antibody fragment
<220> FEATURE:
<221> NAME/KEY: REPEAT
<222> LOCATION: (1)..(5)
<223> OTHER INFORMATION: Repeat from 1 to 5 times.

<400> SEQUENCE: 121

Gly Gly Gly Gly Ser
1               5

<210> SEQ ID NO 122
<211> LENGTH: 5
<212> TYPE: PRT
<213> ORGANISM: Artificial Sequence
<220> FEATURE:
<223> OTHER INFORMATION: Recombinant antibody fragment
<220> FEATURE:
<221> NAME/KEY: REPEAT
<222> LOCATION: (1)..(5)
<223> OTHER INFORMATION: Repeat from 1 to 5 times.

<400> SEQUENCE: 122

Gly Gly Gly Gly Ala
1               5